US009475874B2

(12) United States Patent
Sawada et al.

(10) Patent No.: US 9,475,874 B2
(45) Date of Patent: Oct. 25, 2016

(54) NUCLEIC ACIDS ENCODING HUMAN ANTIBODIES TO SIALYL-LEWIS$^a$

(71) Applicant: MabVax Therapeutics, Inc., San Diego, CA (US)

(72) Inventors: Ritsuko Sawada, San Diego, CA (US); Shu-Man Sun, San Diego, CA (US); Wolfgang Scholz, San Diego, CA (US)

(73) Assignee: MABVAX THERAPEUTICS, INC., San Diego, CA (US)

(*) Notice: Subject to any disclaimer, the term of this patent is extended or adjusted under 35 U.S.C. 154(b) by 122 days.

(21) Appl. No.: 14/468,827

(22) Filed: Aug. 26, 2014

(65) Prior Publication Data
US 2015/0056134 A1 Feb. 26, 2015

Related U.S. Application Data

(60) Provisional application No. 61/870,137, filed on Aug. 26, 2013.

(51) Int. Cl.
| | | |
|---|---|---|
| *A61K 39/395* | (2006.01) | |
| *G01N 33/53* | (2006.01) | |
| *C07K 16/00* | (2006.01) | |
| *C07K 16/28* | (2006.01) | |
| *C07H 21/04* | (2006.01) | |
| *A61K 45/06* | (2006.01) | |
| *A61K 51/10* | (2006.01) | |
| *C07K 16/30* | (2006.01) | |
| *A61K 39/00* | (2006.01) | |

(52) U.S. Cl.
CPC ......... *C07K 16/28* (2013.01); *A61K 39/0011* (2013.01); *A61K 39/39533* (2013.01); *A61K 45/06* (2013.01); *A61K 51/1045* (2013.01); *A61K 51/1057* (2013.01); *C07K 16/3076* (2013.01); *A61K 2039/505* (2013.01); *A61K 2039/6081* (2013.01); *C07K 2317/21* (2013.01); *C07K 2317/33* (2013.01); *C07K 2317/56* (2013.01); *C07K 2317/732* (2013.01); *C07K 2317/734* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,057,313 A | 10/1991 | Shih et al. |
| 5,112,946 A | 5/1992 | Maione et al. |
| 5,223,409 A | 6/1993 | Ladner et al. |
| 5,336,603 A | 8/1994 | Capon et al. |
| 5,349,053 A | 9/1994 | Landolfi et al. |
| 5,359,046 A | 10/1994 | Capon et al. |
| 5,403,484 A | 4/1995 | Ladner et al. |
| 5,427,908 A | 6/1995 | Dower et al. |
| 5,443,953 A | 8/1995 | Hansen et al. |
| 5,447,851 A | 9/1995 | Beutler et al. |
| 5,516,637 A | 5/1996 | Huang et al. |
| 5,571,698 A | 11/1996 | Ladner et al. |
| 5,580,717 A | 12/1996 | Dower et al. |
| 5,587,459 A | 12/1996 | Uckun et al. |
| 5,622,929 A | 4/1997 | Willner et al. |
| 5,648,239 A | 7/1997 | Hawkins et al. |
| 5,658,727 A | 8/1997 | Barbas et al. |
| 5,698,426 A | 12/1997 | Huse et al. |
| 5,723,125 A | 3/1998 | Chang et al. |
| 5,728,868 A | 3/1998 | Springer et al. |
| 5,733,743 A | 3/1998 | Johnson et al. |
| 5,750,753 A | 5/1998 | Kimae et al. |
| 5,780,225 A | 7/1998 | Wigler et al. |
| 5,783,181 A | 7/1998 | Browne et al. |
| 5,795,737 A | 8/1998 | Seed et al. |
| 5,821,047 A | 10/1998 | Garrard et al. |

(Continued)

FOREIGN PATENT DOCUMENTS

| | | |
|---|---|---|
| EP | 307434 | 3/1989 |
| EP | 367166 | 5/1990 |

(Continued)

OTHER PUBLICATIONS

Lewis, Jason., New methods of PET imaging pancreas cancer. Cancer Research (Jul. 1, 2015), vol. 75, No. 13, Suppl Abstract No. 1A116. Abstract meeting.*
Al-Lazikani et al., "Standard conformations for the canonical structures of immunoglobulins," J. Mol. Biol. 273:927-948 (1997).
Ames et al., "Conversion of murine Fabs isolated from a combinatorial phage display library to full length immunoglobulins," J. Immunol. Methods 184:177-186 (1995).
Ashkenazi et al., "Protection against endotoxic shock by a tumor necrosis factor receptor immunoadhesin," Proc. Natl. Acad. Sci. USA, 88: 10535-10539 (1991).
Bebbington et al., "High-level expression of a recombinant antibody from myeloma cells using a glutamine synthetase gene as an amplifiable selectable marker," Biotechnology 10:169 (1992).

(Continued)

*Primary Examiner* — Maher Haddad
(74) *Attorney, Agent, or Firm* — Jones Day

(57) ABSTRACT

The present invention provides compositions for the production of an antibody or functional fragment thereof directed against Sialyl-Lewis$^a$ (sLe$^a$). The compositions of the invention include polynucleotides encoding a heavy chain and/or a light chain variable domain that binds to sLe$^a$. The invention also provides an isolated antibody or functional fragment thereof and methods of treating or preventing a disease, such as cancer or tumor formation, wherein the antibody or functional fragment includes a variable heavy chain domain and a variable light chain domain that has an amino acid sequence provided herein. The invention further provides a conjugate of an antibody or functional fragment thereof conjugated or recombinantly fused to a diagnostic agent, detectable agent or therapeutic agent, and methods of treating, preventing or diagnosing a disease in a subject in need thereof.

20 Claims, 27 Drawing Sheets

(56) References Cited

U.S. PATENT DOCUMENTS

| | | | |
|---|---|---|---|
| 5,844,095 A | 12/1998 | Linsley et al. |
| 5,863,904 A | 1/1999 | Nabel et al. |
| 5,872,223 A | 2/1999 | Uckun et al. |
| 5,908,626 A | 6/1999 | Chang et al. |
| 5,911,995 A | 6/1999 | Uckun et al. |
| 5,922,844 A | 7/1999 | Hawkins et al. |
| 5,925,376 A | 7/1999 | Heng et al. |
| 5,958,769 A | 9/1999 | Roberts et al. |
| 5,969,108 A | 10/1999 | McCafferty et al. |
| 5,985,877 A | 11/1999 | Dionne et al. |
| 6,034,053 A | 3/2000 | Uckun et al. |
| 6,040,305 A | 3/2000 | Taveras et al. |
| 6,051,574 A | 4/2000 | Anthony et al. |
| 6,051,582 A | 4/2000 | Taveras et al. |
| 6,054,466 A | 4/2000 | Ciccarone et al. |
| 6,057,300 A | 5/2000 | Nabel et al. |
| 6,063,930 A | 5/2000 | Dinsmore et al. |
| 6,066,738 A | 5/2000 | Dinsmore et al. |
| 6,071,935 A | 6/2000 | Lyssikatos et al. |
| 6,077,853 A | 6/2000 | Graham et al. |
| 6,080,870 A | 6/2000 | Anthony et al. |
| 6,090,948 A | 7/2000 | Dinsmore et al. |
| 6,093,737 A | 7/2000 | Anthony et al. |
| 6,103,723 A | 8/2000 | Bergman et al. |
| 6,124,295 A | 9/2000 | Taveras et al. |
| 6,124,465 A | 9/2000 | Bourzat et al. |
| 6,127,366 A | 10/2000 | Kim et al. |
| 6,133,303 A | 10/2000 | Bikker et al. |
| 6,143,766 A | 11/2000 | Kaltenbronn et al. |
| 6,159,984 A | 12/2000 | Guzi et al. |
| 6,169,096 B1 | 1/2001 | Venet et al. |
| 6,187,786 B1 | 2/2001 | Venet et al. |
| 6,218,372 B1 | 4/2001 | Nabel et al. |
| 6,218,406 B1 | 4/2001 | Bourzat et al. |
| 6,218,410 B1 | 4/2001 | Uehata et al. |
| 6,225,322 B1 | 5/2001 | Cooper et al. |
| 6,228,856 B1 | 5/2001 | Njoroge et al. |
| 6,228,865 B1 | 5/2001 | Doll et al. |
| 6,232,338 B1 | 5/2001 | Davies et al. |
| 6,239,140 B1 | 5/2001 | Cooper et al. |
| 6,242,196 B1 | 6/2001 | Spiegelman et al. |
| 6,245,759 B1 | 6/2001 | Bilodeau et al. |
| 6,248,756 B1 | 6/2001 | Anthony et al. |
| 6,254,868 B1 | 7/2001 | Leung et al. |
| 6,265,422 B1 | 7/2001 | Bikker et al. |
| 6,268,363 B1 | 7/2001 | Lee et al. |
| 6,271,242 B1 | 8/2001 | Barbacid et al. |
| 6,300,501 B1 | 10/2001 | Dobrusin et al. |
| 6,335,156 B1 | 1/2002 | Hermeking et al. |
| 6,342,487 B1 | 1/2002 | Riou et al. |
| 6,342,765 B1 | 1/2002 | Arnould et al. |
| 6,362,188 B1 | 3/2002 | Guzi et al. |
| 6,369,034 B1 | 4/2002 | Doherty et al. |
| 6,372,747 B1 | 4/2002 | Taveras et al. |
| 6,383,790 B1 | 5/2002 | Shokat et al. |
| 6,387,905 B2 | 5/2002 | Njoroge et al. |
| 6,399,615 B1 | 6/2002 | Guzi et al. |
| 6,399,633 B1 | 6/2002 | Dumont et al. |
| 6,403,581 B1 | 6/2002 | Ayral-Kaloustian et al. |
| 6,410,539 B1 | 6/2002 | Arnould et al. |
| 6,410,541 B2 | 6/2002 | Remiszewski et al. |
| 6,414,145 B1 | 7/2002 | Boyle et al. |
| 6,420,387 B1 | 7/2002 | Venet et al. |
| 6,432,959 B1 | 8/2002 | Cooper et al. |
| 6,436,960 B1 | 8/2002 | Shin et al. |
| 6,440,974 B2 | 8/2002 | Doll et al. |
| 6,451,812 B1 | 9/2002 | End et al. |
| 6,458,935 B1 | 10/2002 | Burns et al. |
| 7,981,695 B2 | 7/2011 | Schultz et al. |
| 8,039,273 B2 | 10/2011 | Jeffrey et al. |
| 8,142,784 B2 | 3/2012 | Ebens et al. |
| 2005/0003469 A1 | 1/2005 | Watkins et al. |
| 2008/0076161 A1 | 3/2008 | Angov et al. |
| 2009/0202536 A1 | 8/2009 | Ebens et al. |
| 2009/0203538 A1 | 8/2009 | Sugioka et al. |
| 2010/0034837 A1 | 2/2010 | Beria et al. |
| 2011/0137017 A1 | 6/2011 | Eigenbrot et al. |
| 2011/0280891 A1 | 11/2011 | Liu et al. |
| 2011/0311517 A1 | 12/2011 | Li et al. |
| 2012/0003247 A1 | 1/2012 | Doronina et al. |
| 2012/0195905 A1 | 8/2012 | Bedian et al. |
| 2013/0209481 A1 | 8/2013 | Zhou et al. |

FOREIGN PATENT DOCUMENTS

| | | |
|---|---|---|
| EP | 394827 | 10/1990 |
| WO | WO 90/02809 | 3/1990 |
| WO | WO 91/06570 | 5/1991 |
| WO | WO 91/10737 | 7/1991 |
| WO | WO 92/01047 | 1/1992 |
| WO | WO 92/18619 | 10/1992 |
| WO | WO 92/22324 | 12/1992 |
| WO | WO 93/11236 | 6/1993 |
| WO | WO 95/15982 | 6/1995 |
| WO | WO 95/20401 | 8/1995 |
| WO | WO 96/04388 | 2/1996 |
| WO | WO 96/22024 | 7/1996 |
| WO | WO97/13844 | 4/1997 |
| WO | WO 97/34631 | 9/1997 |
| WO | WO 98/39027 | 9/1998 |
| WO | WO 99/04813 | 2/1999 |
| WO | WO 2008/000632 | 1/2008 |
| WO | WO 2009/033011 | 3/2009 |

OTHER PUBLICATIONS

Ben-David et al., "The involvement of the sLe-a selectin ligand in the extravasation of human colorectal carcinoma cells," Immunol Lett, 116:218-224 (2008).

Better et al., "*Escherichia coli* secretion of an active chimeric antibody fragment," Science 240:1041-1043 (1988).

Bird et al., "Single-chain antigen-binding proteins," Science 242:423-26 (1988).

Bittner et al., "Expression and Secretion Vectors for Yeast," Methods in Enzymol., 153:516-544 (1987).

Brinkman et al., "Phage display of disulfide-stabilized Fv fragments," J. Immunol. Methods 182:41-50 (1995).

Brochet et al., "IMGT/V-QUEST: the highly customized and integrated system for IG and TR standardized V-J and V-D-J sequence analysis," Nucleic Acids Res, 36:W503-8. (2008).

Burton et al., "Human antibodies from combinatorial libraries," Advances in Immunology 57:191-280 (1994).

Chothia and Lesk, "Canonical structures for the hypervariable regions of immunoglobulins," J. Mol. Biol. 196:901-917 (1987).

Cockett et al., "High level expression of tissue inhibitor of metalloproteinases in Chinese hamster ovary cells using glutamine synthetase gene amplification," 8: 662-667 (1990).

Crouse et al., "Expression and amplification of engineered mouse dihydrofolate reductase minigenes," Mol. Cell. Biol. 3:257 (1983).

DeNardo et al., "Comparison of 1,4,7,10-tetraazacyclododecane-N,N',N",N'''-tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts," Clin Cancer Res. 4(10):2483-2490 (1998).

Dickler et al. "Immunogenicity of a fucosyl-GM1-keyhole limpet hemocyanin conjugate vaccine in patients with small cell lung cancer," Cancer Res 1999, 5:2773.

Feizi T., "Demonstration by monoclonal antibodies that carbohydrate structures of glycoproteins and glycolipids are onco-developmental antigens," Nature, 314:53-7 (1985).

Foecking et al., "Powerful and versatile enhancer—promoter unit for mammalian expression vectors," Gene 45:101-105 (1986).

Gilewski et al., "Immunization of metastatic breast cancer patients with a fully synthetic globo H conjugate: a phase I trial," Proc. Natl. Acad. Sci. U.S.A., 98:3270-5 (2001).

Gilewski et al., "Vaccination of high-risk breast cancer patients with mucin-1 (MUC1) keyhole limpet hemocyanin conjugate plus QS-21," Clin Cancer Res, 6:1693-1701 (2000).

(56) References Cited

OTHER PUBLICATIONS

Gottfried and Weinhold, "Sequence-specific covalent labelling of DNA," Biochem. Soc. Trans., 39(2):523-528 (2011).

Hellstrom et al., "Highly tumor-reactive, internalizing, mouse monoclonal antibodies to Le(y)-related cell surface antigens," Cancer Res 50:2183-2190 (1990).

Holland et al., Journal of Nuclear Medicine official publication, Society of Nuclear Medicine 51:1293-300 (2010).

Holland et al., "Standardized methods for the production of high specific-activity zirconium-89," Nuclear Medicine and Biology 36:729-739 (2009).

Holliger et al., ""Diabodies": small bivalent and bispecific antibody fragments," Proc. Natl. Acad. Sci. USA 90:6444-48 (1993).

Huston et al., "Antigen recognition and targeted delivery by the single-chain Fv," Cell Biophysics, 22:189-224 (1993).

Huston et al., "Protein engineering of antibody binding sites: recovery of specific activity in an anti-digoxin single-chain Fv analogue produced in *Escherichia coli*," Proc. Natl. Acad. Sci. USA 85:5879-5883 (1988).

Inouye & Inouye, "Up-promoter mutations in the lpp gene of *Escherichia coli*," Nucleic Acids Res. 13:3101-3109 (1985).

Jalkanen et al., "Cell surface proteoglycan of mouse mammary epithelial cells is shed by cleavage of its matrix-binding ectodomain from its membrane-associated domain," J. Cell . Biol. 105:3087-3096 (1987).

Jalkanen et al., "Heparan sulfate proteoglycans from mouse mammary epithelial cells: localization on the cell surface with a monoclonal antibody," J. Cell. Biol. 101:976-985 (1985).

Kabat et al., "Unusual distributions of amino acids in complementarity-determining (hypervariable) segments of heavy and light chains of immunoglobulins and their possible roles in specificity of antibody-combining sites," J. Biol. Chem. 252:6609-6616 (1977).

Kabat, "The structural basis of antibody complementarity," Adv. Prot. Chem. 32:1-75 (1978).

Kanaya et al., "Studies of codon usage and tRNA genes of 18 unicellular organisms and quantification of Bacillus subtilis tRNAs: gene expression level and species-specific diversity of codon usage based on multivariate analysis," Gene, 238:143-155 (1999).

Kannagi R., "Carbohydrate antigen sialyl Lewis a—its pathophysiological significance and induction mechanism in cancer progression," Chang Gung Med J, 30:189-209 (2007).

Kawamura et al., "Introduction of Sd(a) carbohydrate antigen in gastrointestinal cancer cells eliminates selectin ligands and inhibits metastasis," Cancer Res, 65:6220-6227 (2005).

Kettleborough et al., "Isolation of tumor cell-specific single-chain Fv from immunized mice using phage-antibody libraries and the re-construction of whole antibodies from these antibody fragments," Eur. J. Immunol. 24:952-958 (1994).

Kohler, "Immunoglobulin chain loss in hybridoma lines," Proc. Natl. Acad. Sci. USA 77:2197-2199 (1980).

Kutmeier et al., "Assembly of humanized antibody genes from synthetic oligonucleotides using a single-round PCR," BioTechniques 17:242 (1994).

Leung et al., "Engineering a unique glycosylation site for site-specific conjugation of haptens to antibody fragments," J. Immunol., 154: 5919-5926 (1995).

Lewis, Jason S., "New Directions in PET Imaging," Memorial-Sloan Kettering Cancer Center, pp. 1-37 (2012).

Lloyd KO, "Molecular characteristic of tumor antigens," Immunol Allergy Clin N America, 10:765-79 (1990).

Kishimoto et al., "Phenotypes correlating to metastatic properties of pancreas adenocarcinoma in vivo: the importance of surface sialyl Lewis(a) antigen," Int J Cancer, 69:290-294 (1996).

Kohls et al., "Mab-ZAP: a tool for evaluating antibody efficacy for use in an immunotoxin," Biotechniques 28:162-165 (2000).

Lindmo et al., "Determination of the immunoreactive fraction of radiolabeled monoclonal antibodies by linear extrapolation to binding at infinite antigen excess," Journal of Immunological Methods 72:77-89 (1984).

Logan & Shenk, "Adenovirus tripartite leader sequence enhances translation of mRNAs late after infection," Proc. Natl. Acad. Sci. USA 8 1:355-359 (1984).

Lowy et al., "Isolation of transforming DNA: cloning the hamster aprt gene", Cell 22:8-17 (1980).

Matsui et al., "Sialyl Lewis$^a$ expression as a predictor of the prognosis of colon carcinoma patients in a prospective randomized clinical trial," Jpn J Clin Oncol, 34:588-593 (2004).

Morea et al., "Antibody modeling: implications for engineering and design," Methods 20:267-279 (2000).

Morgan and Anderson, "Human gene therapy," Ann. Rev. Biochem. 62:191-217 (1993).

Mulligan & Berg, "Selection for animal cells that express the *Escherichia coli* gene coding for xanthine-guanine phosphoribosyltransferase," Proc. Natl. Acad. Sci. USA 78:2072 (1981).

Mulligan, "The basic science of gene therapy," Science 260:926-932 (1993).

Mullinax et al., "Expression of a heterodimeric Fab antibody protein in one cloning step," BioTechniques 12(6):864-869 (1992).

Nakayama et al., "Expression of sialyl Lewis(a) as a new prognostic factor for patients with advanced colorectal carcinoma," Cancer, 75:2051-2056 (1995).

Natsume et al., "Fucose removal from complex-type oligosaccharide enhances the antibody-dependent cellular cytotoxicity of single-gene-encoded antibody comprising a single-chain antibody linked the antibody constant region," J. Immunol. Methods., 306:93-103 (2005).

O'Hare et al., "Transformation of mouse fibroblasts to methotrexate resistance by a recombinant plasmid expressing a prokaryotic dihydrofolate reductase," Proc. Natl. Acad. Sci. USA 78:1527 (1981).

Okazaki et al., "Fucose depletion from human IgG1 oligosaccharide enhances binding enthalpy and association rate between IgG1 and FcgammaRIIIa," J Mol Biol., 336:1239-1249 (2004).

Paredes et al., "RNA labeling, conjugation and ligation," Methods, 54(2):251-259 (2011).

Peipp et al., "Antibody fucosylation differentially impacts cytotoxicity mediated by NK and PMN effector cells," Blood, 112(6):2390-2399 (2008).

Persic et al., "An integrated vector system for the eukaryotic expression of antibodies or their fragments after selection from phage display libraries," Gene 187:9-18 (1997).

Peterson et al., "Enzymatic cleavage of peptide-linked radiolabels from immunoconjugates," Bioconjug. Chem. 10(4):553-557 (1999).

Pettengill et al., "Isolation and growth characteristics of continuous cell lines from small-cell carcinoma of the lung," Cancer, 45:906-918 (1980).

Plückthun and Skerra, "Expression of functional antibody Fv and Fab fragments in *Escherichia coli*," Meth. Enzymol., 178:497-515 (1989).

Poljak et al., "Production and structure of diabodies.," Structure 2:1121-23 (1994).

Pritsch et al., "V Gene Usage by Seven Hybrids Derived From CD5+ B-Cell Chronic Lymphocytic Leukemia and Displaying Autoantibody Activity," Blood, 82(10):3103-3112 (1993).

Proudfoot, "Transcriptional interference and termination between duplicated alpha-globin gene constructs suggests a novel mechanism for gene regulation." Nature 322:(6079): 562-565(1986).

Ragupathi et al., "Consistent antibody response against ganglioside GD2 induced in patients with melanoma by a GD2 lactone-keyhole limpet hemocyanin conjugate vaccine plus immunological adjuvant QS-21," Clin Cancer Res 2003, 9:5214.

Ragupathi et al., "Induction of antibodies against GD3 ganglioside in melanoma patients by vaccination with GD3-lactone-KLH conjugate plus immunological adjuvant QS-21," Int J Cancer 2000, 85:659.

Ragupathi et al., "Synthesis of sialyl Lewis(a) (sLe (a), CA19-9) and construction of an immunogenic sLe(a) vaccine," Cancer Immunol Immunother, 58:1397-1405 (2009).

Santerre et al., "Expression of prokaryotic genes for hygromycin B and G418 resistance as dominant-selection markers in mouse L cells," Gene 30:147 (1984).

(56) References Cited

OTHER PUBLICATIONS

Sato et al., "The association of sialyl Lewis(a) antigen with the metastatic potential of human colon cancer cells," Anticancer Res, 17:3505-3511 (1997).
Sawada-Hirai al., "Human anti-anthrax protective antigen neutralizing monoclonal antibodies derived from donors vaccinated with anthrax vaccine adsorbed," J Immune Based Ther Vaccines, 2:5 (2004).
Sawada et al., "Human Monoclonal Antibodies to Sialyl-Lewisa (CA19.9) with Potent CDC, ADCC Activity," MabVax Therapeutics Poster (2009).
Sawada et al., "Human Monoclonal Antibodies to Sialyl-Lewisa (CA19.9) with Potent CDC, ADCC, and Antitumor Activity," Clinical Cancer Research, 17:1024-1032 (2011).
Sawai et al., "Direct production of the Fab fragment derived from the sperm immobilizing antibody using polymerase chain reaction and cDNA expression vectors," AJRI 34:26-34 (1995).
Senter, "Potent antibody drug conjugates for cancer therapy," Current Opinion in Chemical Biology, 13:235-244 (2009).
Shields et al., "Lack of fucose on human IgG1 N-linked oligosaccharide improves binding to human Fcgamma RIII and antibody-dependent cellular toxicity," J. Biol. Chem., 277(30):26733-40 (2002).
Shih et al., "A fluorouridine-anti-CEA immunoconjugate is therapeutically effective in a human colonic cancer xenograft model," Int. J. Cancer. 46:1101-1106 (1990).
Shih et al., "Site-specific linkage of methotrexate to monoclonal antibodies using an intermediate carrier," Int. J. Cancer. 41:832-839 (1988).
Souza et al., "Peripheral B Cells Latently Infected with Epstein-Barr Virus Display Molecular Hallmarks of Classical Antigen-Selected Memory B Cells," Proc. Natl. Acad. Sci, 102:18093-18098 (2005).
Steplewska-Mazur et al., "Breast cancer progression and expression of blood group-related tumor-associated antigens," Hybridoma, 19:129-133 (2000).
Szybalska & Szybalski, "Genetics of human cell lines, IV. DNA-mediated heritable transformation of a biochemical trait." Proc. Natl. Acad. Sci. USA 48(12): 2026-2034 (1962).
Thorpe et al., "The preparation and cytotoxic properties of antibody-toxin conjugates," Immunol. Rev. 62:119-158 (1982).

Tolstoshev, "Gene therapy, concepts, current trials and future directions," Ann. Rev. Pharmacol. Toxicol. 32:573-596 (1993).
Trail et al., "Cure of xenografted human carcinomas by BR96-doxorubicin immunoconjugates," Science 261:212-5 (1993).
Traunecker et al., "Soluble CD4 molecules neutralize human immunodeficiency virus type 1," Nature, 331:84-86 (1988).
Ugorski et al., "Sialyl Lewis(a): a tumor-associated carbohydrate antigen involved in adhesion and metastatic potential of cancer cells," Acta Biochim Pol, 49:303-311 (2002).
Van Heeke & Schuster, "Expression of human asparagine synthetase in *Escherichia coli*," J. Biol. Chem. 24:5503-5509 (1989).
Vie et al., "Human fusion proteins between interleukin 2 and IgM heavy chain are cytotoxic for cells expressing the interleukin 2 receptor," Proc. Natl. Acad. Sci. USA, 89:11337-11341 (1992).
Wang et al., "Analysis of codon usage patterns of bacterial genomes using the self-organizing map," Mol. Biol. Evol., 18(5):792-800 (2001).
Ward et al., "Binding activities of a repertoire of single immunoglobulin variable domains secreted from *Escherichia coli*," Nature 341:544-546 (1989).
Wigler et al., "Transfer of purified herpes virus thymidine kinase gene to cultured mouse cells," Cell 11:223 (1977).
Wigler et al., "Transformation of mammalian cells with an amplifiable dominant-acting gene," Proc. Natl. Acad. Sci. U S A. 77(6):3567-3570 (1980).
Wu and Wu, "Delivery systems for gene therapy," Biotherapy 3:87-95 (1991).
Wu et al., "Potent CDC, ADCC and Anti-Tumor Activity of Human Monoclonal Antibodies to Sialyl-Lewis A," MabVax Therapeutics Poster (2011).
Yu et al., "Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells," Int. J. Cancer 56: 244 (1994).
Zheng et al., "Administration of noncytolytic IL-10/Fc in murine models of lipopolysaccharide-induced septic shock and allogeneic islet transplantation," J. Immunol., 154:5590-5600, 1995.
Zimmerman et al., "A triglycine linker improves tumor uptake and biodistributions of 67-Cu-labeled anti-neuroblastoma MAb chCE7 F(ab')2 fragments," Nucl. Med. Biol. 26(8):943-950 (1999).

* cited by examiner

```
                Leader
    M  E  F  G  L  S  W  L  F  L  V  A  I  L  K  G  V  Q  C  Q
  1 ATGGAGTTTG GGCTGAGCTG GCTTTTTCTT GTGGCTATTT TAAAAGGCGT ACAGTGCCAG
    V  Q  L  V  E  S  G  G  S  V  Q  P  G  R  S  L  R  L  S
 61 GTGCAGCTGG TGGAGTCTGG GGGAGGCTCG GTGCAGCCTG GCAGGTCCCT GAGACTCTCC
                                 CDR1
    C  E  A  S  G  F  T  F  E  A  Y  A  M  H  W  V  R  Q  P  P
121 TGTGAAGCCT CTGGATTCAC CTTTGAGGCC TATGCCATGC ACTGGGTCCG GCAACCTCCA
                                 CDR2
    G  K  G  L  E  W  V  S  S  I  N  W  N  S  G  R  I  A  Y  A
181 GGGAAGGGCC TGGAGTGGGT CTCAAGTATT AATTGGAATA GTGGTCGCAT AGCCTATGCG
    D  S  V  K  G  R  F  T  I  S  R  D  N  A  R  N  S  L  Y  L
241 GACTCTGTGA AGGGCCGATT CACCATCTCC AGAGACAACG CCAGGAATTC CCTGTATCTG
    Q  M  N  S  L  R  L  E  D  T  A  F  Y  Y  C  A  K  D  I  R
301 CAAATGAACA GTCTGAGACT TGAGGACACG GCCTTCTATT ACTGTGCAAA AGATATACGG
    CDR3
    R  F  S  T  G  G  A  E  F  E  Y  W  G  Q  G  T  L  V  T  V
361 AGGTTTAGTA CCGGGGGGGC GGAGTTTGAG TACTGGGGCC AGGGAACCCT GGTCACCGTC
    S  S
421 TCCTCA
```

SEQ ID NO: 1 (5B1 VH)

```
  1 ATGGAGTTTG GGCTGAGCTG GCTTTTTCTT GTGGCTATTT TAAAAGGCGT ACAGTGCCAG
 61 GTGCAGCTGG TGGAGTCTGG GGGAGGCTCG GTGCAGCCTG GCAGGTCCCT GAGACTCTCC
121 TGTGAAGCCT CTGGATTCAC CTTTGAGGCC TATGCCATGC ACTGGGTCCG GCAACCTCCA
181 GGGAAGGGCC TGGAGTGGGT CTCAAGTATT AATTGGAATA GTGGTCGCAT AGCCTATGCG
241 GACTCTGTGA AGGGCCGATT CACCATCTCC AGAGACAACG CCAGGAATTC CCTGTATCTG
301 CAAATGAACA GTCTGAGACT TGAGGACACG GCCTTCTATT ACTGTGCAAA AGATATACGG
361 AGGTTTAGTA CCGGGGGGGC GGAGTTTGAG TACTGGGGCC AGGGAACCCT GGTCACCGTC
421 TCCTCA
```

SEQ ID NO: 2 (5B1 VH)

```
  1 MEFGLSWLFL VAILKGVQCQ VQLVESGGGS VQPGRSLRLS CEASGFTFEA YAMHWVRQPP
 61 GKGLEWVSSI NWNSGRIAYA DSVKGRFTIS RDNARNSLYL QMNSLRLEDT AFYYCAKDIR
121 RFSTGGAEFE YWGQGTLVTV SS
```

FIG. 1

```
                          Leader
       M   A   G   F   P   L   L   L   T   L   L   T   H   C   A   G   S   W   A   Q
  1  ATGGCCGGCT TCCCTCTCCT CCTCACCCTC CTCACTCACT GTGCAGGGTC TTGGGCCCAG
       S   V   L   T   Q   P   P   S   A   S   G   T   P   G   Q   R   V   T   I   S
 61  TCTGTGCTGA CTCAGCCGCC CTCAGCGTCT GGGACCCCCG GGCAGAGGGT CACCATCTCT
                          CDR1
       C   S   G   S   S   S   N   I   G   S   N   F   V   Y   W   Y   Q   Q   L   P
121  TGTTCTGGAA GCAGCTCCAA CATCGGAAGT AATTTTGTAT ACTGGTACCA GCAGCTCCCA
                                         CDR2
       G   T   A   P   K   L   L   I   Y   R   N   N   Q   R   P   S   G   V   P   D
181  GGAACGGCCC CCAAACTCCT CATATATAGG AATAATCAGC GGCCCTCAGG GGTCCCTGAC
       R   F   S   G   S   R   S   G   T   S   A   S   L   A   I   S   G   L   R   S
241  CGATTCTCTG GCTCCAGGTC TGGCACCTCA GCCTCCCTGG CCATCAGTGG ACTCCGGTCC
                                      CDR3
       E   D   E   A   D   Y   Y   C   A   A   W   D   D   S   L   G   G   H   Y   V
301  GAGGATGAGG CTGATTATTA CTGTGCAGCA TGGGATGACA GCCTGGGAGG CCATTATGTC
       F   G   T   G   T   K   V   T   V   L
361  TTCGGAACTG GGACCAAGGT CACCGTCCTT
```

SEQ ID NO: 3 (5B1 VL)

```
  1  ATGGCCGGCT TCCCTCTCCT CCTCACCCTC CTCACTCACT GTGCAGGGTC TTGGGCCCAG
 61  TCTGTGCTGA CTCAGCCGCC CTCAGCGTCT GGGACCCCCG GGCAGAGGGT CACCATCTCT
121  TGTTCTGGAA GCAGCTCCAA CATCGGAAGT AATTTTGTAT ACTGGTACCA GCAGCTCCCA
181  GGAACGGCCC CCAAACTCCT CATATATAGG AATAATCAGC GGCCCTCAGG GGTCCCTGAC
241  CGATTCTCTG GCTCCAGGTC TGGCACCTCA GCCTCCCTGG CCATCAGTGG ACTCCGGTCC
301  GAGGATGAGG CTGATTATTA CTGTGCAGCA TGGGATGACA GCCTGGGAGG CCATTATGTC
361  TTCGGAACTG GGACCAAGGT CACCGTCCTT
```

SEQ ID NO: 4 (5B1 VL)

```
  1  MAGFPLLLTL LTHCAGSWAQ SVLTQPPSAS GTPGQRVTIS CSGSSSNIGS NFVYWYQQLP
 61  GTAPKLLIYR NNQRPSGVPD RFSGSRSGTS ASLAISGLRS EDEADYYCAA WDDSLGGHYV
121  FGTGTKVTVL
```

FIG. 2

```
                    Leader
      M  E  F  G  L  S  W  L  F  L  V  A  I  L  K  G  V  Q  C  E
    1 ATGGAGTTTG GGCTGAGCTG GCTTTTTCTT GTGGCTATTT TAAAAGGCGT ACAGTGCGAA
      V  Q  L  L  E  S  G  G  G  L  V  Q  P  G  R  S  L  R  L  S
   61 GTGCAGCTGT GGAGTCTGG GGGAGGCTTG GTACAGCCTG GCAGGTCCCT GAGACTCTCC
                                 CDR1
      C  A  A  S  G  F  T  F  D  D  Y  V  M  H  W  V  R  Q  A  P
  121 TGTGCGGCCT CTGGATTTAC CTTTGATGAT TATGTCATGC ACTGGGTCCG GCAAGCTCCA
                                             CDR2
      G  K  G  L  E  W  V  S  S  I  S  W  N  S  G  S  I  G  Y  A
  181 GGGAAGGGCC TGGAGTGGGT CTCAAGTATT AGTTGGAATA GTGGTAGCAT AGGCTATGCG
      D  S  V  K  G  R  F  I  I  S  R  D  N  A  K  N  S  L  Y  L
  241 GACTCTGTGA AGGGCCGATT CATCATCTCC AGAGACAACG CCAAGAACTC CCTGTATCTG
      Q  M  N  S  L  R  A  E  D  T  A  L  Y  Y  C  A  K  D  R  R
  301 CAAATGAACA GTCTGAGAGC TGAGGACACG GCCTTGTATT ACTGTGCAAA AGATCGTCGT
          CDR3
      I  R  G  D  S  G  F  E  G  D  Y  W  G  Q  G  T  L  V  T  V
  361 ATTAGGGGTG ACTCGGGGTT CGAGGGTGAC TACTGGGGCC AGGGAACCCT GGTCACCGTC
      S  S
  421 TCCTCA
```

SEQ ID NO: 5 (9H3 VH)

```
    1 ATGGAGTTTG GGCTGAGCTG GCTTTTTCTT GTGGCTATTT TAAAAGGCGT ACAGTGCGAA
   61 GTGCAGCTGT GGAGTCTGG GGGAGGCTTG GTACAGCCTG GCAGGTCCCT GAGACTCTCC
  121 TGTGCGGCCT CTGGATTTAC CTTTGATGAT TATGTCATGC ACTGGGTCCG GCAAGCTCCA
  181 GGGAAGGGCC TGGAGTGGGT CTCAAGTATT AGTTGGAATA GTGGTAGCAT AGGCTATGCG
  241 GACTCTGTGA AGGGCCGATT CATCATCTCC AGAGACAACG CCAAGAACTC CCTGTATCTG
  301 CAAATGAACA GTCTGAGAGC TGAGGACACG GCCTTGTATT ACTGTGCAAA AGATCGTCGT
  361 ATTAGGGGTG ACTCGGGGTT CGAGGGTGAC TACTGGGGCC AGGGAACCCT GGTCACCGTC
  421 TCCTCA
```

SEQ ID NO: 6 (9H3 VH)

```
    1 MEFGLSWLFL VAILKGVQCE VQLLESGGGL VQPGRSLRLS CAASGFTFDD YVMHWVRQAP
   61 GKGLEWVSSI SWNSGSIGYA DSVKGRFIIS RDNAKNSLYL QMNSLRAEDT ALYYCAKDRR
  121 IRGDSGFEGD YWGQGTLVTV SS
```

FIG. 3

```
                                           Leader
      M   A   G   F   P   L   L   L   T   L   L   T   H   C   A   G   S   W   A   Q
   1 ATGGCCGGCT TCCCTCTCCT CCTCACCCTC CTCACTCACT GTGCAGGGTC TTGGGCCCAG
      S   V   L   T   Q   P   P   S   A   S   G   T   P   G   Q   R   V   T   I   S
  61 TCTGTGTTGA CGCAGCCGCC CTCAGCGTCT GGGACCCCCG GCAGAGGGT  CACCATCTCT
                                    CDR1
      C   S   G   S   S   S   N   I   G   S   N   Y   V   Y   W   Y   Q   Q   L   P
 121 TGTTCTGGAA GCAGCTCCAA CATCGGAAGT AATTATGTAT ACTGGTACCA GCAGCTCCCA
                                    CDR2
      G   T   A   P   K   L   L   I   Y   R   N   N   Q   R   P   S   G   V   P   D
 181 GGAACGGCCC CCAAACTCCT CATCTATAGG AATAATCAGC GGCCCTCAGG GGTCCCTGAC
      R   F   S   G   S   K   S   G   T   S   A   S   L   A   I   S   G   L   R   S
 241 CGATTCTCTG GCTCCAAGTC TGGCACCTCA GCCTCCCTGG CCATCAGTGG GCTCCGGTCC
                                             CDR3
      E   D   E   A   D   Y   Y   C   A   A   W   D   A   S   L   S   G   V   V   F
 301 GAGGATGAGG CTGATTATTA CTGTGCAGCA TGGGATGCCA GCCTGAGTGG TGTGGTATTC
      G   G   T   K   L   T   V   L
 361 GGCGGAGGGA CCAAGCTGAC CGTCCTA
```

SEQ ID NO: 7 (9H3 VL)

```
   1 ATGGCCGGCT TCCCTCTCCT CCTCACCCTC CTCACTCACT GTGCAGGGTC TTGGGCCCAG
  61 TCTGTGTTGA CGCAGCCGCC CTCAGCGTCT GGGACCCCCG GCAGAGGGT  CACCATCTCT
 121 TGTTCTGGAA GCAGCTCCAA CATCGGAAGT AATTATGTAT ACTGGTACCA GCAGCTCCCA
 181 GGAACGGCCC CCAAACTCCT CATCTATAGG AATAATCAGC GGCCCTCAGG GGTCCCTGAC
 241 CGATTCTCTG GCTCCAAGTC TGGCACCTCA GCCTCCCTGG CCATCAGTGG GCTCCGGTCC
 301 GAGGATGAGG CTGATTATTA CTGTGCAGCA TGGGATGCCA GCCTGAGTGG TGTGGTATTC
 361 GGCGGAGGGA CCAAGCTGAC CGTCCTA
```

SEQ ID NO: 8 (9H3 VL)

```
   1 MAGFPLLLTL LTHCAGSWAQ SVLTQPPSAS GTPGQRVTIS CSGSSSNIGS NYVYWYQQLP
  61 GTAPKLLIYR NNQRPSGVPD RFSGSKSGTS ASLAISGLRS EDEADYYCAA WDASLSGVVF
 121 GGGTKLTVL
```

FIG. 4

```
                        Leader
       M   E   F   G   L   S   W   L   F   L   V   A   I   L   K   G   V   Q   C   Q
   1 ATGGAGTTTG GGCTGAGCTG GCTTTTTCTT GTGGCTATTT TAAAAGGCGT ACAGTGCCAG
       V   Q   L   L   E   S   G   G   G   L   V   Q   P   G   R   S   L   R   L   S
  61 GTGCAGCTGT TGGAGTCTGG GGGAGGCTTG GTACAGCCTG GCAGGTCCCT GAGACTCTCC
                                              CDR1
       C   A   A   S   G   F   T   F   D   E   Y   A   M   H   W   V   R   Q   A   P
 121 TGTGCAGCCT CTGGATTCAC CTTTGATGAA TATGCCATGC ACTGGGTCCG GCAAGCTCCA
                                              CDR2
       G   K   G   L   E   W   V   S   S   V   S   W   N   S   G   S   I   G   Y   A
 181 GGGAAGGGCC TGGAGTGGGT CTCAAGTGTT AGTTGGAATA GTGGTAGCAT AGGCTATGCG
       D   S   V   K   G   R   F   T   I   S   R   D   N   A   K   N   S   L   Y   L
 241 GACTCTGTGA AGGGCCGATT CACCATCTCC AGAGACAACG CCAAGAACTC CCTGTATCTA
       Q   M   N   S   L   R   A   E   D   T   A   L   Y   Y   C   A   K   D   I   R
 301 CAAATGAACA GTCTGAGAGC TGAGGACACG GCCTTGTATT ACTGTGCAAA AGATATACGG
           CDR3
       T   Y   S   T   G   G   A   E   F   A   S   W   G   Q   G   T   L   V   T   A
 361 ACCTATAGCA CCGGGGGGGC GGAGTTTGCC TCCTGGGGCC AGGGAACCCT GGTCACCGCC
       S   S
 421 TCCTCA
```

SEQ ID NO: 9 (5H11 VH)

```
   1 ATGGAGTTTG GGCTGAGCTG GCTTTTTCTT GTGGCTATTT TAAAAGGCGT ACAGTGCCAG
  61 GTGCAGCTGT TGGAGTCTGG GGGAGGCTTG GTACAGCCTG GCAGGTCCCT GAGACTCTCC
 121 TGTGCAGCCT CTGGATTCAC CTTTGATGAA TATGCCATGC ACTGGGTCCG GCAAGCTCCA
 181 GGGAAGGGCC TGGAGTGGGT CTCAAGTGTT AGTTGGAATA GTGGTAGCAT AGGCTATGCG
 241 GACTCTGTGA AGGGCCGATT CACCATCTCC AGAGACAACG CCAAGAACTC CCTGTATCTA
 301 CAAATGAACA GTCTGAGAGC TGAGGACACG GCCTTGTATT ACTGTGCAAA AGATATACGG
 361 ACCTATAGCA CCGGGGGGGC GGAGTTTGCC TCCTGGGGCC AGGGAACCCT GGTCACCGCC
 421 TCCTCA
```

SEQ ID NO: 10 (5H11 VH)

```
   1 MEFGLSWLFL VAILKGVQCQ VQLLESGGGL VQPGRSLRLS CAASGFTFDE YAMHWVRQAP
  61 GKGLEWVSSV SWNSGSIGYA DSVKGRFTIS RDNAKNSLYL QMNSLRAEDT ALYYCAKDIR
 121 TYSTGGAEFA SWGQGTLVTA SS
```

FIG. 5

```
                             Leader
     M   A   G   F   P   L   L   L   T   L   L   T   H   C   A   G   S   W   A   Q
   1 ATGGCCGGCT TCCCTCTCCT CCTCACCCTC CTCACTCACT GTGCAGGGTC TTGGGCCCAG
     S   V   L   T   Q   P   P   S   A   S   G   T   P   G   Q   R   V   T   I   S
  61 TCTGTGTTGA CGCAGCCGCC CTCAGCGTCT GGGACCCCCG GCAGAGGGT CACCATCTCT
                             CDR1
     C   S   G   S   S   S   N   I   G   S   N   Y   V   Y   W   Y   Q   Q   V   P
 121 TGTTCTGGAA GCAGCTCCAA CATCGGAAGT AATTATGTAT ACTGGTACCA GCAGGTCCCA
                                     CDR2
     G   T   A   P   K   L   L   I   Y   R   N   N   Q   R   P   S   G   V   P   D
 181 GGAACGGCCC CCAAACTCCT CATCTATAGG AATAATCAGC GGCCCTCAGG GGTCCCTGAC
     R   F   S   G   S   K   S   G   T   S   A   S   L   A   I   S   G   L   R   S
 241 CGATTCTCTG GCTCCAAGTC TGGCACCTCA GCCTCCCTGG CCATCAGTGG GCTCCGGTCC
                                                             CDR3
     E   D   E   A   D   Y   Y   C   A   A   W   D   D   S   L   S   G   H   Y   V
 301 GAGGATGAGG CTGATTATTA CTGTGCAGCA TGGGATGACA GCCTGAGTGG CCATTATGTC
     F   G   T   G   T   K   V   T   V   L
 361 TTCGGAACTG GGACCAAGGT CACCGTCCTA
```

SEQ ID NO: 11 (5H11 VL)

```
   1 ATGGCCGGCT TCCCTCTCCT CCTCACCCTC CTCACTCACT GTGCAGGGTC TTGGGCCCAG
  61 TCTGTGTTGA CGCAGCCGCC CTCAGCGTCT GGGACCCCCG GCAGAGGGT CACCATCTCT
 121 TGTTCTGGAA GCAGCTCCAA CATCGGAAGT AATTATGTAT ACTGGTACCA GCAGGTCCCA
 181 GGAACGGCCC CCAAACTCCT CATCTATAGG AATAATCAGC GGCCCTCAGG GGTCCCTGAC
 241 CGATTCTCTG GCTCCAAGTC TGGCACCTCA GCCTCCCTGG CCATCAGTGG GCTCCGGTCC
 301 GAGGATGAGG CTGATTATTA CTGTGCAGCA TGGGATGACA GCCTGAGTGG CCATTATGTC
 361 TTCGGAACTG GGACCAAGGT CACCGTCCTA
```

SEQ ID NO: 12 (5H11 VL)

```
   1 MAGFPLLLTL LTHCAGSWAQ SVLTQPPSAS GTPGQRVTIS CSGSSSNIGS NYVYWYQQVP
  61 GTAPKLLIYR NNQRPSGVPD RFSGSKSGTS ASLAISGLRS EDEADYYCAA WDDSLSGHYV
 121 FGTGTKVTVL
```

FIG. 6

```
                                      Leader
       M  E  F  G    L  S  W  L  F    L  V  A  I  L    K  G  V  Q  C    Q
  1 ATGGAGTTTG GGCTGAGCTG GCTTTTTCTT GTGGCTATTT TAAAAGGCGT ACAGTGCCAA
       V  Q  L  L    E  S  G    G  G  V    V  Q  P  G  R    S  L  R  L  S
 61 GTGCAGCTGT TGGAGTCTGG GGGAGGCGTG GTCCAGCCTG GAGGTCCCT GAGACTCTCC
                                 CDR1
       C  A  A  S    G  F  T    F  S  F    Y  G  M  H  W    V  R  Q  A  P
121 TGTGCAGCCT CTGGATTCAC CTTCAGTTTC TATGGCATGC ACTGGGTCCG CCAGGCTCCA
                                              CDR2
       G  K  G  L    E  W  V    A  A  I    S  Y  D  G  S  N    Y  Y  A
181 GGCAAGGGGC TGGAGTGGGT GGCAGCTATA TCATATGATG GAAGTAATAA ATACTATGCA
       D  S  V  K    G  R  F    T  I  S    R  D  N  S  K  N    T  L  Y  L
241 GACTCCGTGA AGGGCCGATT CACCATCTCC AGAGACAATT CCAAGAACAC GCTGTATCTG
       Q  M  N  S    L  R  A    E  D  T    A  V  Y  Y  C    A  K  R  P  N
301 CAAATGAACA GCCTGAGAGC TGAGGACACG GCTGTGTATT ACTGTGCGAA AAGGCCCAAC
       CDR3
       Q  F  Y  C    S  D  G    R  C  Y    S  I  D  Y  W    G  Q  G  T  L
361 CAATTTTATT GTAGTGATGG TAGATGCTAC TCCATTGACT ACTGGGGCCA GGGAACCCTG
       V  T  V  S    S
421 GTCACCGTCT CCTCA
```

SEQ ID NO: 13 (7E3 VH)

```
  1 ATGGAGTTTG GCTGAGCTG GCTTTTTCTT GTGGCTATTT TAAAAGGCGT ACAGTGCCAA
 61 GTGCAGCTGT TGGAGTCTGG GGGAGGCGTG GTCCAGCCTG GAGGTCCCT GAGACTCTCC
121 TGTGCAGCCT CTGGATTCAC CTTCAGTTTC TATGGCATGC ACTGGGTCCG CCAGGCTCCA
181 GGCAAGGGGC TGGAGTGGGT GGCAGCTATA TCATATGATG GAAGTAATAA ATACTATGCA
241 GACTCCGTGA AGGGCCGATT CACCATCTCC AGAGACAATT CCAAGAACAC GCTGTATCTG
301 CAAATGAACA GCCTGAGAGC TGAGGACACG GCTGTGTATT ACTGTGCGAA AAGGCCCAAC
361 CAATTTTATT GTAGTGATGG TAGATGCTAC TCCATTGACT ACTGGGGCCA GGGAACCCTG
421 GTCACCGTCT CCTCA
```

SEQ ID NO: 14 (7E3 VH)

```
  1 MEFGLSWLFL VAILKGVQCQ VQLLESGGGV VQPGRSLRLS CAASGFTFSF YGMHWVRQAP
 61 GKGLEWVAAI SYDGSNKYYA DSVKGRFTIS RDNSKNTLYL QMNSLRAEDT AVYYCAKRPN
121 QFYCSDGRCY SIDYWGQGTL VTVSS
```

FIG. 7

```
                     Leader
          M  D  M  R  V  P  A  Q  L  L  G  L  L  L  W  L  R  G  A
  1 ATGGACATGA GGGTCCCCGC TCAGCTCCTG GGGCTCCTGC TACTCTGGCT CCGAGGTGCC
          R  C  E  I  V  M  T  Q  S  P  A  T  L  S  V  S  P  G  E  R
 61 CGGTGTGAAA TTGTAATGAC GCAGTCTCCA GCCACCCTGT CTGTGTCTCC AGGGGAGAGA
                                                    CDR1
          A  T  L  S  C  R  A  S  Q  S  V  S  S  N  L  A  W  Y  Q  Q
121 GCCACCCTCT CCTGCAGGGC CAGTCAGAGT GTTAGCAGCA ACTTAGCCTG GTACCAGCAG
                                          CDR2
          K  P  G  Q  A  P  R  L  L  I  Y  G  A  S  T  R  A  T  G  I
181 AAACCTGGCC AGGCTCCCAG GCTCCTCATC TATGGTGCAT CCACCAGGGC CACTGGTATC
          P  A  R  F  S  G  S  G  S  G  T  D  F  T  L  T  I  S  S  L
241 CCAGCCAGGT TCAGTGGCAG TGGGTCTGGG ACAGACTTCA CTCTCACCAT CAGCAGCCTG
                                                 CDR3
          Q  S  V  D  S  A  V  Y  Y  C  Q  Q  Y  N  N  W  P  P  Y  T
301 CAGTCTGTAG ATTCTGCAGT TTATTACTGT CAGCAGTATA ATAACTGGCC TCCGTACACT
          F  G  Q  G  T  K  L  E  I  K
361 TTTGGCCAGG GGACCAAGCT GGAGATCAAA
```

SEQ ID NO: 15 (7E3 VK)

```
  1 ATGGACATGA GGGTCCCCGC TCAGCTCCTG GGGCTCCTGC TACTCTGGCT CCGAGGTGCC
 61 CGGTGTGAAA TTGTAATGAC GCAGTCTCCA GCCACCCTGT CTGTGTCTCC AGGGGAGAGA
121 GCCACCCTCT CCTGCAGGGC CAGTCAGAGT GTTAGCAGCA ACTTAGCCTG GTACCAGCAG
181 AAACCTGGCC AGGCTCCCAG GCTCCTCATC TATGGTGCAT CCACCAGGGC CACTGGTATC
241 CCAGCCAGGT TCAGTGGCAG TGGGTCTGGG ACAGACTTCA CTCTCACCAT CAGCAGCCTG
301 CAGTCTGTAG ATTCTGCAGT TTATTACTGT CAGCAGTATA ATAACTGGCC TCCGTACACT
361 TTTGGCCAGG GGACCAAGCT GGAGATCAAA
```

SEQ ID NO: 16 (7E3 VK)

```
  1 MDMRVPAQLL GLLLLWLRGA RCEIVMTQSP ATLSVSPGER ATLSCRASQS VSSNLAWYQQ
 61 KPGQAPRLLI YGASTRATGI PARFSGSGSG TDFTLTISSL QSVDSAVYYC QQYNNWPPYT
121 FGQGTKLEIK
```

FIG. 8

```
        Q   S   V   L   T   Q   P   P   S   A   S   G   T   P   G   Q   R   V   T   I
  1   CAGTCTGTGC TGACGCAGCC GCCCTCAGCG TCTGGGACCC CCGGGCAGAG GGTCACCATC
                                           VL CDR1
        S   C   S   G   S   S   N   I   G   S   N   F   V   Y   W   Y   Q   Q   L
 61   TCTTGTTCTG GAAGCAGCTC CAACATCGGA AGTAATTTTG TATACTGGTA CCAGCAGCTC
                                           VL CDR2
        P   G   T   A   P   K   L   L   I   Y   R   N   N   Q   R   P   S   G   V   P
121   CCAGGAACGG CCCCCAAACT CCTCATATAT AGGAATAATC AGCGGCCCTC AGGGGTCCCT
        D   R   F   S   G   S   R   S   G   T   S   A   S   L   A   I   S   G   L   R
181   GACCGATTCT CTGGCTCCAG GTCTGGCACC TCAGCCTCCC TGGCCATCAG TGGACTCCGG
                                                                VL CDR3
        S   E   D   E   A   D   Y   Y   C   A   A   W   D   D   S   L   G   G   H   Y
241   TCCGAGGATG AGGCTGATTA TTACTGTGCA GCATGGGATG ACAGCCTGGG AGGCCATTAT
                                             Linker
        V   F   G   T   G   T   K   V   T   V   L   S   G   G   G   G   Q   V   Q   L
301   GTCTTCGGAA CTGGGACCAA GGTCACCGTC CTTTCTGGTG GTGGTGGTCA GGTGCAGCTG
        V   E   S   G   G   S   V   Q   P   G   R   S   L   R   L   S   C   E   A
361   GTGGAGTCTG GGGGAGGCTC GGTGCAGCCT GGCAGGTCCC TGAGACTCTC CTGTGAAGCC
                         VH CDR1
        S   G   F   T   F   E   A   Y   A   M   H   W   V   R   Q   P   P   G   K   G
421   TCTGGATTCA CCTTTGAGGC CTATGCCATG CACTGGGTCC GGCAACCTCC AGGGAAGGGC
                                        VH CDR2
        L   E   W   V   S   S   I   N   W   N   S   G   R   I   A   Y   A   D   S   V
481   CTGGAGTGGG TCTCAAGTAT TAATTGGAAT AGTGGTCGCA TAGCCTATGC GGACTCTGTG
        K   G   R   F   T   I   S   R   D   N   A   R   N   S   L   Y   L   Q   M   N
541   AAGGGCCGAT TCACCATCTC CAGAGACAAC GCCAGGAATT CCCTGTATCT GCAAATGAAC
                                                                 VH CDR3
        S   L   R   L   E   D   T   A   F   Y   Y   C   A   K   D   I   R   R   F   S
601   AGTCTGAGAC TTGAGGACAC GGCCTTCTAT TACTGTGCAA AGATATACG GAGGTTTAGT
        T   G   G   A   E   F   E   Y   W   G   Q   G   T   L   V   T   V   S   S   G
661   ACCGGGGGGG CGGAGTTTGA GTACTGGGGC CAGGGAACCC TGGTCACCGT CTCCTCAGGT
                 Poly His-Tag
        S   H   H   H   H   H   H   G   G   C
721   TCTCACCATC ACCATCACCA TGGCGGTTGC SEQ ID NO: 17
  1   CAGTCTGTGC TGACGCAGCC GCCCTCAGCG TCTGGGACCC CCGGGCAGAG GGTCACCATC
 61   TCTTGTTCTG GAAGCAGCTC CAACATCGGA AGTAATTTTG TATACTGGTA CCAGCAGCTC
121   CCAGGAACGG CCCCCAAACT CCTCATATAT AGGAATAATC AGCGGCCCTC AGGGGTCCCT
181   GACCGATTCT CTGGCTCCAG GTCTGGCACC TCAGCCTCCC TGGCCATCAG TGGACTCCGG
241   TCCGAGGATG AGGCTGATTA TTACTGTGCA GCATGGGATG ACAGCCTGGG AGGCCATTAT
301   GTCTTCGGAA CTGGGACCAA GGTCACCGTC CTTTCTGGTG GTGGTGGTCA GGTGCAGCTG
361   GTGGAGTCTG GGGGAGGCTC GGTGCAGCCT GGCAGGTCCC TGAGACTCTC CTGTGAAGCC
421   TCTGGATTCA CCTTTGAGGC CTATGCCATG CACTGGGTCC GGCAACCTCC AGGGAAGGGC
481   CTGGAGTGGG TCTCAAGTAT TAATTGGAAT AGTGGTCGCA TAGCCTATGC GGACTCTGTG
541   AAGGGCCGAT TCACCATCTC CAGAGACAAC GCCAGGAATT CCCTGTATCT GCAAATGAAC
601   AGTCTGAGAC TTGAGGACAC GGCCTTCTAT TACTGTGCAA AGATATACG GAGGTTTAGT
661   ACCGGGGGGG CGGAGTTTGA GTACTGGGGC CAGGGAACCC TGGTCACCGT CTCCTCAGGT
721   TCTCACCATC ACCATCACCA TGGCGGTTGC SEQ ID NO: 18
  1   QSVLTQPPSA SGTPGQRVTI SCSGSSSNIG SNFVYWYQQL PGTAPKLLIY RNNQRPSGVP
 61   DRFSGSRSGT SASLAISGLR SEDEADYYCA AWDDSLGGHY VFGTGTKVTV LSGGGGQVQL
121   VESGGSVQP GRSLRLSCEA SGFTFEAYAM HWVRQPPGKG LEWVSSINWN SGRIAYADSV
181   KGRFTISRDN ARNSLYLQMN SLRLEDTAFY YCAKDIRRFS TGGAEFEYWG QGTLVTVSSG
241   SHHHHHHGGC
```

FIG. 9

```
        D   V   V   L   T   Q   S   P   A   T   L   S   V   S   P   G   E   R   A   T
  1   GATGTTGTGC TGACGCAGTC TCCAGCCACC CTGTCTGTGT CTCCAGGGGA GAGAGCCACC
                                            VL CDR1
        L   S   C   R   A   S   Q   S   V   S   S   N   L   A   W   Y   Q   Q   K   P
 61   CTCTCCTGCA GGGCCAGTCA GAGTGTTAGC AGCAACTTAG CCTGGTACCA GCAGAAACCT
                                            VL CDR2
        G   Q   A   P   R   L   L   I   Y   G   A   S   T   R   A   T   G   I   P   A
121   GGCCAGGCTC CCAGGCTCCT CATCTATGGT GCATCCACCA GGGCCACTGG TATCCCAGCC
        R   F   S   G   S   G   S   G   T   D   F   T   L   T   I   S   S   L   Q   S
181   AGGTTCAGTG GCAGTGGGTC TGGGACAGAC TTCACTCTCA CCATCAGCAG CCTGCAGTCT
                                                        VL CDR3
        E   D   S   A   V   Y   Y   C   Q   Q   Y   N   N   W   P   P   Y   T   F   G
241   GAAGATTCTG CAGTTTATTA CTGTCAGCAG TATAATAACT GGCCTCCGTA CACTTTTGGC
                                        Linker
        Q   G   T   K   V   D   I   K   S   G   G   G   E   V   Q   L   V   E   S
301   CAGGGGACCA AGGTGGATAT CAAATCTGGT GGTGGTGGTG AAGTGCAGCT GGTGGAGTCT
        G   G   G   V   Q   P   G   R   S   L   R   L   S   C   A   A   S   G   F
361   GGGGGAGGCG TGGTCCAGCC TGGGAGGTCC CTGAGACTCT CCTGTGCAGC CTCTGGATTC
        VH CDR1
        T   F   S   F   Y   G   M   H   W   V   R   Q   A   P   G   K   G   L   E   W
421   ACCTTCAGTT TCTATGGCAT GCACTGGGTC CGCCAGGCTC CAGGCAAGGG GCTGGAGTGG
                                    VH CDR2
        V   A   A   I   S   Y   D   G   S   N   K   Y   Y   A   D   S   V   K   G   R
481   GTGGCAGCTA TATCATATGA TGGAAGTAAT AAATACTATG CAGACTCCGT GAAGGGCCGA
        F   T   I   S   R   D   N   S   K   N   T   L   Y   L   Q   M   N   S   L   R
541   TTCACCATCT CCAGAGACAA TTCCAAGAAC ACGCTGTATC TGCAAATGAA CAGCCTGAGA
                                                        VH CDR3
        A   E   D   T   A   V   Y   Y   C   A   K   R   P   N   Q   F   Y   C   S   D
601   GCTGAGGACA CGGCTGTGTA TTACTGTGCG AAAAGGCCCA ACCAATTTTA TTGTAGTGAT
        G   R   C   Y   S   I   D   Y   W   G   Q   G   T   L   V   T   V   S   S   G
661   GGTAGATGCT ACTCCATTGA CTACTGGGGC CAGGGAACCC TGGTCACCGT CTCCTCAGGT
            Poly His-Tag
        S   H   H   H   H   H   H   G   G   C
721   TCTCACCATC ACCATCACCA TGGCGGTTGC SEQ ID NO: 19
  1   GATGTTGTGC TGACGCAGTC TCCAGCCACC CTGTCTGTGT CTCCAGGGGA GAGAGCCACC
 61   CTCTCCTGCA GGGCCAGTCA GAGTGTTAGC AGCAACTTAG CCTGGTACCA GCAGAAACCT
121   GGCCAGGCTC CCAGGCTCCT CATCTATGGT GCATCCACCA GGGCCACTGG TATCCCAGCC
181   AGGTTCAGTG GCAGTGGGTC TGGGACAGAC TTCACTCTCA CCATCAGCAG CCTGCAGTCT
241   GAAGATTCTG CAGTTTATTA CTGTCAGCAG TATAATAACT GGCCTCCGTA CACTTTTGGC
301   CAGGGGACCA AGGTGGATAT CAAATCTGGT GGTGGTGGTG AAGTGCAGCT GGTGGAGTCT
361   GGGGGAGGCG TGGTCCAGCC TGGGAGGTCC CTGAGACTCT CCTGTGCAGC CTCTGGATTC
421   ACCTTCAGTT TCTATGGCAT GCACTGGGTC CGCCAGGCTC CAGGCAAGGG GCTGGAGTGG
481   GTGGCAGCTA TATCATATGA TGGAAGTAAT AAATACTATG CAGACTCCGT GAAGGGCCGA
541   TTCACCATCT CCAGAGACAA TTCCAAGAAC ACGCTGTATC TGCAAATGAA CAGCCTGAGA
601   GCTGAGGACA CGGCTGTGTA TTACTGTGCG AAAAGGCCCA ACCAATTTTA TTGTAGTGAT
661   GGTAGATGCT ACTCCATTGA CTACTGGGGC CAGGGAACCC TGGTCACCGT CTCCTCAGGT
721   TCTCACCATC ACCATCACCA TGGCGGTTGC SEQ ID NO: 20
  1   DVVLTQSPAT LSVSPGERAT LSCRASQSVS SNLAWYQQKP QAPRLLIYGA STRATGIPAR
 61   FSGSGSGTDF TLTISSLQSE DSAVYYCQQY NNWPPYTFGQ GTKVDIKSGG GGEVQLVESG
121   GGVVQPGRSL RLSCAASGFT FSFYGMHWVR QAPGKGLEWV AAISYDGSNK YYADSVKGRF
181   TISRDNSKNT LYLQMNSLRA EDTAVYYCAK RPNQFYCSDG RCYSIDYWGQ GTLVTVSSGS
241   HHHHHHGGC
```

FIG. 10

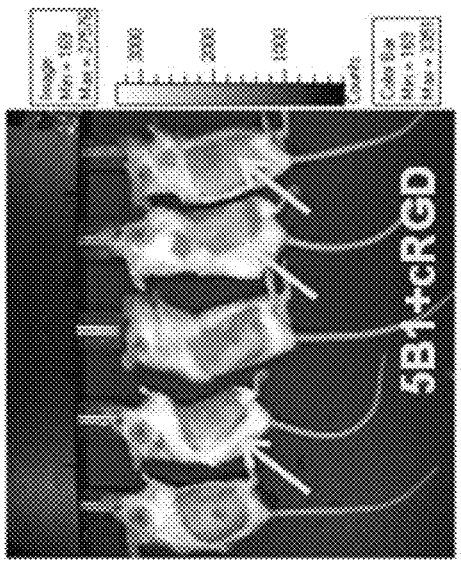
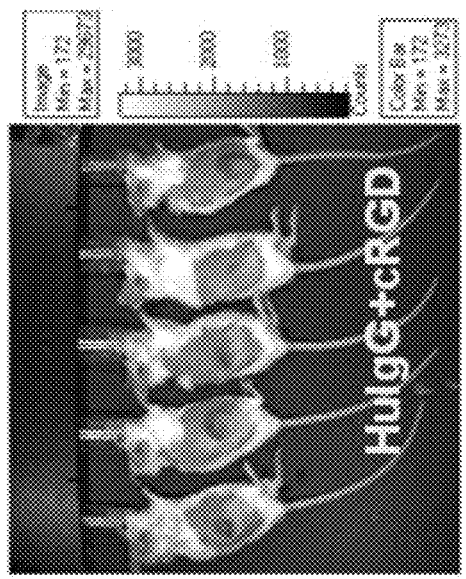
FIG. 18B

US 9,475,874 B2

NUCLEIC ACIDS ENCODING HUMAN ANTIBODIES TO SIALYL-LEWIS$^a$

This application claims the benefit of priority of U.S. Provisional Application Ser. No. 61/870,137, filed Aug. 26, 2013, the entire contents of which is incorporated herein by reference.

This invention was made with government support under grant number CA-128362 awarded by the National Cancer Institute, NIH. The government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 25, 2014, is named 12967-033-999_Sequence_Listing.txt and is 23,080 bytes in size.

BACKGROUND OF THE INVENTION

The present invention relates generally to antibodies directed against Sialyl-Lewis$^a$ (sLe$^a$), and more specifically to polynucleotides encoding anti-sLe$^a$ antibodies and the corresponding encoded antibodies or fragments thereof.

Passive administration of antibodies directed against tumor specific antigens may eliminate tumor cells and early metastases during cancer development. This treatment may also have a significant impact on cancer recurrence. Antibodies directed against tumor specific carbohydrates may be useful candidates in this cancer treatment. For example, many tumor-restricted monoclonal antibodies resulting from immunization of mice with human cancer cells have been shown to be directed against carbohydrate antigens expressed at the cell surface as glycolipids or glycoproteins. The carbohydrate sLe$^a$ has been shown to be expressed on tumors of the gastrointestinal tract. Expression of sLe$^a$ has also been shown to impact metastatic potential and correlates with increased metastatic potential in human colon cancer and pancreatic adenocarcinoma. However, carbohydrate chemistry has been rather challenging and the clinical development of antibodies that recognize such tumor specific carbohydrates has been slow.

Pancreatic carcinoma is one of the most aggressive adenocarcinomas and is often associated with a poor prognosis. Pancreatic carcinoma ranks as the fourth leading cause of cancer mortality. Despite advances in the screening for different carcinomas, the reliability of detecting malignant lesions stemming from the pancreas remains poor. Positron emission tomography utilizing fluorodeoxyglucase (FDG-PET) has been indicated for the detection and staging of pancreatic cancer. However, FDG-PET is insensitive to differentiating pancreatitis from malignancy and remains problematic in staging small primary lesions (<7 mm) and liver metastases (<1 cm). One diagnostic screening method used to monitor the state of pancreatic ductal adenocarcinoma (PDAC) patients includes detecting elevated levels of circulating sLe$^a$ antigen in sera. Patients with >37 U/ml of circulating sLe$^a$ antigen indicates cancer recurrence. However, development of alternative diagnostic tools that utilize such tumor specific carbohydrates has been slow.

Thus, there exists a need for identifying and generating antibodies that specifically recognize tumor specific carbohydrates, such as sLe$^a$, for the treatment of recurring cancers and for detecting malignant lesions and metastases. This invention satisfies this need and provides related advantages.

SUMMARY OF INVENTION

In accordance with the present invention, herein provided are compositions for producing antibodies or functional fragments thereof that bind sLe$^a$. The compositions include an isolated polynucleotide encoding an antibody or a functional fragment thereof, wherein the antibody includes a variable heavy chain (VH) domain that has an amino acid sequence provided herein. The isolated polynucleotide of the invention can also include a nucleic acid sequence provided herein, wherein the nucleic acid sequence encodes the VH domain of the antibody or functional fragment thereof.

In another embodiment of the invention, the isolated polynucleotide can encode an antibody or a functional fragment thereof, wherein the antibody includes a variable light chain (VL) domain that has an amino acid sequence provided herein. The isolated polynucleotide of the invention can also include a nucleic acid sequence provided herein, wherein the nucleic acid sequence encodes the VL domain of the antibody or functional fragment thereof.

The compositions of the invention also include an isolated antibody or functional fragment thereof, wherein the antibody binds to sLe$^a$. In some embodiments, the invention provides an isolated antibody or functional fragment thereof that binds to sLe$^a$, wherein the antibody or functional fragment thereof includes a VH domain having an amino acid sequence provided herein.

In some embodiments, the invention provides an isolated antibody or functional fragment thereof that binds to sLe$^a$, wherein the antibody or functional fragment thereof includes a VL domain having an amino acid sequence provided herein.

In some embodiments, the invention provides an isolated antibody or functional fragment thereof that binds to sLe$^a$, wherein the antibody or functional fragment thereof includes both a VH domain and a VL domain, where the VH domain and the VL domain respectively include an amino acid sequence for the respective VH and VL domains of the clonal isolates provided herein.

In some embodiments, the invention provides a conjugate having an antibody or functional fragment provided herein that is conjugated or recombinantly fused to a diagnostic agent, detectable agent or therapeutic agent. In some aspects of the invention, a conjugate of the invention that includes a detectable agent can be used in a method for detecting and/or diagnosing tumor formation is a subject. Such methods can include administering an effective amount of the conjugate to a subject in need thereof.

In some embodiments, the invention provides pharmaceutical compositions having one or more antibody or functional fragment of the invention and a pharmaceutically acceptable carrier. In some aspects, the invention also provides a method for treating or preventing a disease in a subject in need thereof, by administering a therapeutically effective amount of a pharmaceutical composition of the invention. In still another aspect, the invention provides administering a second therapeutic agent concurrently or successively with an antibody or functional fragment of the invention.

BRIEF DESCRIPTION OF THE DRAWINGS

FIG. 1 shows the nucleotide sequence and the encoded amino acid sequence of the variable heavy (VH) chain domain of clone 5B1 and a leader sequence that can be used for recombinant expression. The top portion of the figure shows an alignment between the nucleotide sequence of SEQ ID NO: 1 and amino acid sequence of SEQ ID NO: 2. The three complementarity determining regions (CDR1, CDR2 and CDR3) are also identified.

FIG. 2 shows the nucleotide sequence and the encoded amino acid sequence of the variable light (VL) chain domain of clone 5B1 and a leader sequence that can be used for recombinant expression. The top portion of the figure shows an alignment between the nucleotide sequence of SEQ ID NO: 3 and amino acid sequence of SEQ ID NO: 4. The three complementarity determining regions (CDR1, CDR2 and CDR3) are also identified.

FIG. 3 shows the nucleotide sequence and the encoded amino acid sequence of the variable heavy (VH) chain domain of clone 9H3 and a leader sequence that can be used for recombinant expression. The top portion of the figure shows an alignment between the nucleotide sequence of SEQ ID NO: 5 and amino acid sequence of SEQ ID NO: 6. The three complementarity determining regions (CDR1, CDR2 and CDR3) are also identified.

FIG. 4 shows the nucleotide sequence and the encoded amino acid sequence of the variable light (VL) chain domain of clone 9H3 and a leader sequence that can be used for recombinant expression. The top portion of the figure shows an alignment between the nucleotide sequence of SEQ ID NO: 7 and amino acid sequence of SEQ ID NO: 8. The three complementarity determining regions (CDR1, CDR2 and CDR3) are also identified.

FIG. 5 shows the nucleotide sequence and the encoded amino acid sequence of the variable heavy (VH) chain domain of clone 5H11 and a leader sequence that can be used for recombinant expression. The top portion of the figure shows an alignment between the nucleotide sequence of SEQ ID NO: 9 and amino acid sequence of SEQ ID NO: 10. The three complementarity determining regions (CDR1, CDR2 and CDR3) are also identified.

FIG. 6 shows the nucleotide sequence and the encoded amino acid sequence of the variable light (VL) chain domain of clone 5H11 and a leader sequence that can be used for recombinant expression. The top portion of the figure shows an alignment between the nucleotide sequence of SEQ ID NO: 11 and amino acid sequence of SEQ ID NO: 12. The three complementarity determining regions (CDR1, CDR2 and CDR3) are also identified.

FIG. 7 shows the nucleotide sequence and the encoded amino acid sequence of the variable heavy (VH) chain domain of clone 7E3 and a leader sequence that can be used for recombinant expression. The top portion of the figure shows an alignment between the nucleotide sequence of SEQ ID NO: 13 and amino acid sequence of SEQ ID NO: 14. The three complementarity determining regions (CDR1, CDR2 and CDR3) are also identified.

FIG. 8 shows the nucleotide sequence and the encoded amino acid sequence of the variable light (VL) chain domain of clone 7E3 and a leader sequence that can be used for recombinant expression. The top portion of the figure shows an alignment between the nucleotide sequence of SEQ ID NO: 15 and amino acid sequence of SEQ ID NO: 16. The three complementarity determining regions (CDR1, CDR2 and CDR3) are also identified.

FIG. 9 shows the nucleotide sequence and the encoded amino acid sequence of a diabody designated 5B1CysDb having CDR1, CDR2 and CDR2 of both the variable heavy (VH) and variable light (VL) chain domains of clone 5B1. The top portion of the figure shows an alignment between the nucleotide sequence of SEQ ID NO: 17 and amino acid sequence of SEQ ID NO: 18. The three complementarity determining regions (CDR1, CDR2 and CDR3) for both the VH and VL domains are identified in bold and underline text. The linker sequence and polyhistidine tag (Poly His-Tag) with added amino acids are also indicated by italic and underline text.

FIG. 10 shows the nucleotide sequence and the encoded amino acid sequence of a diabody designated 7E3CysDb having CDR1, CDR2 and CDR2 of both the variable heavy (VH) and variable light (VL) chain domains of clone 7E3. The top portion of the figure shows an alignment between the nucleotide sequence of SEQ ID NO: 19 and amino acid sequence of SEQ ID NO: 20. The three complementarity determining regions (CDR1, CDR2 and CDR3) for both the VH and VL domains are identified in bold and underline text. The linker sequence and polyhistidine tag (Poly His-Tag) with added amino acids are also indicated by italic and underline text.

FIGS. 11A to 11E show the binding of human anti-sLe$^a$ antibodies to tumor cells analyzed by flow cytometry. FIG. 11A shows DMS-79 cells stained with recombinant (r) 5B1, 9H3, 5H11, and 7E3 antibodies. FIGS. 11B-F respectively shows HT29, BxPC3, SW626, SK-MEL28, and Colo205-luc cells stained with 1-2 μg/mL of r5B1 or r7E3 plus IgG or IgM-specific secondary antibody as described in Example I.

Figure 16:
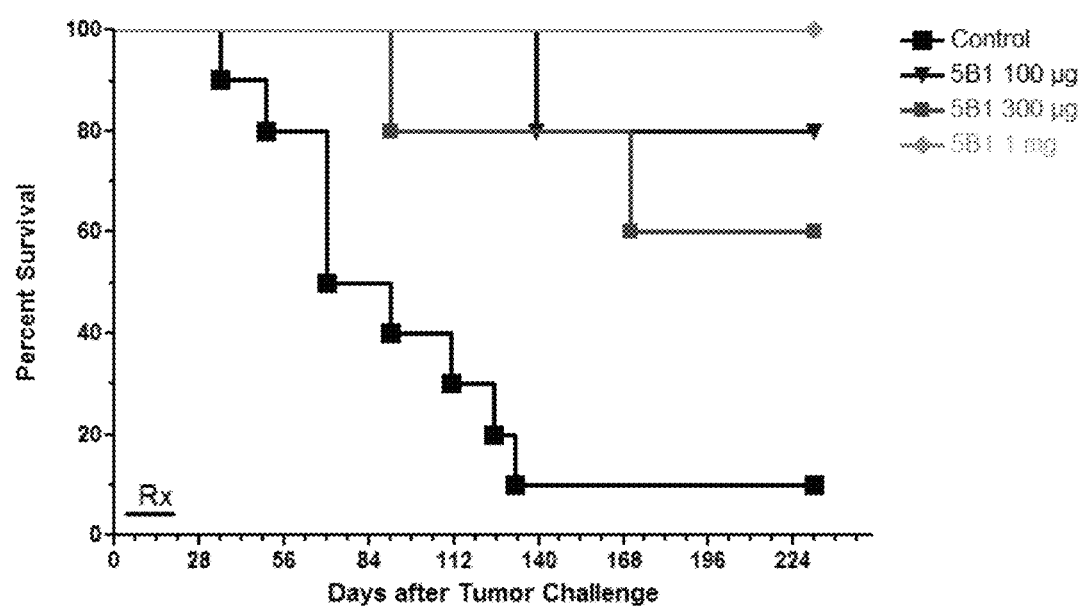
FIG. 16 shows the effect of r5B1 on Colo205-luc tumors in SCID mice. Mice received 100 μg (▼), 300 μg (■) or 1 mg (♦) r5B1 antibody per injection as described in Example I. Control (■) animals received PBS mock injections.
Figure 17:
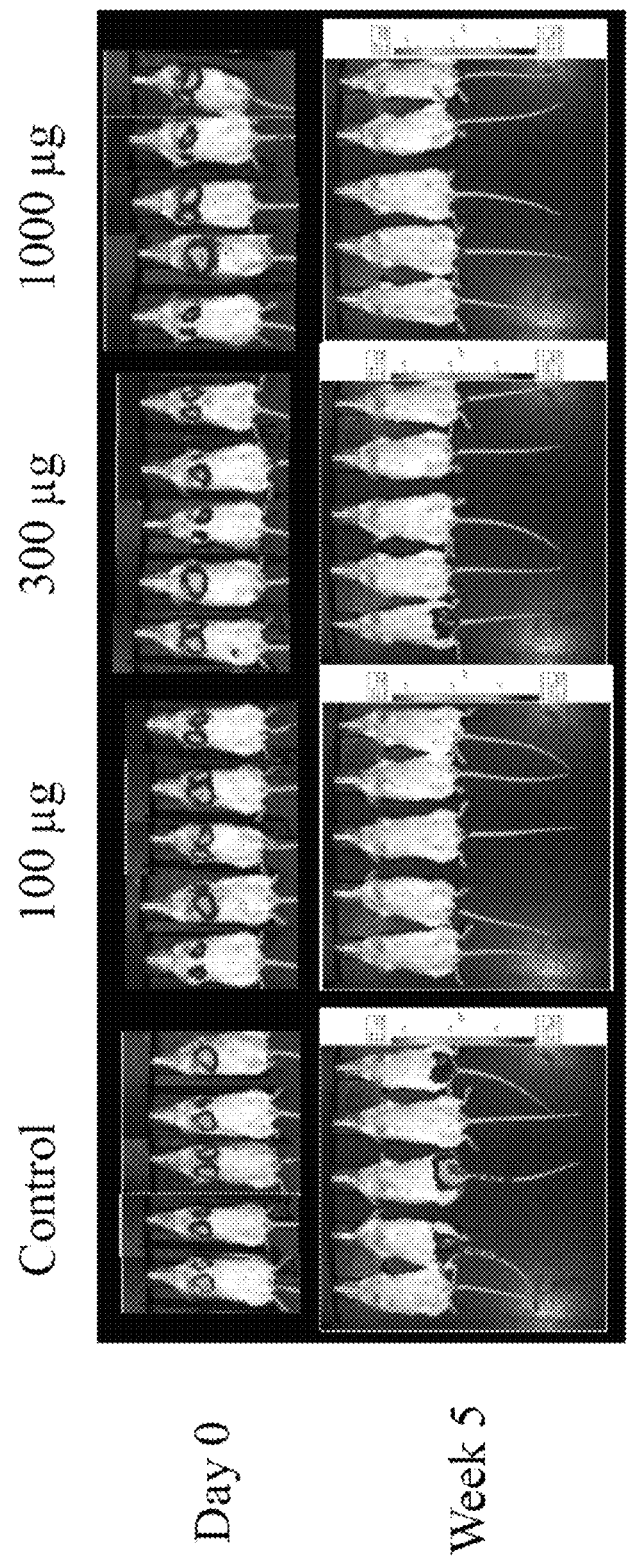

FIG. 17 shows the fluorescence imaging of five mice per group for r5B1 treated mice having Colo205-luc tumors at Day 0 and Week 5. The mice received the treatment regiment depicted in FIG. 16 and described in Example I.

Figure 18A:
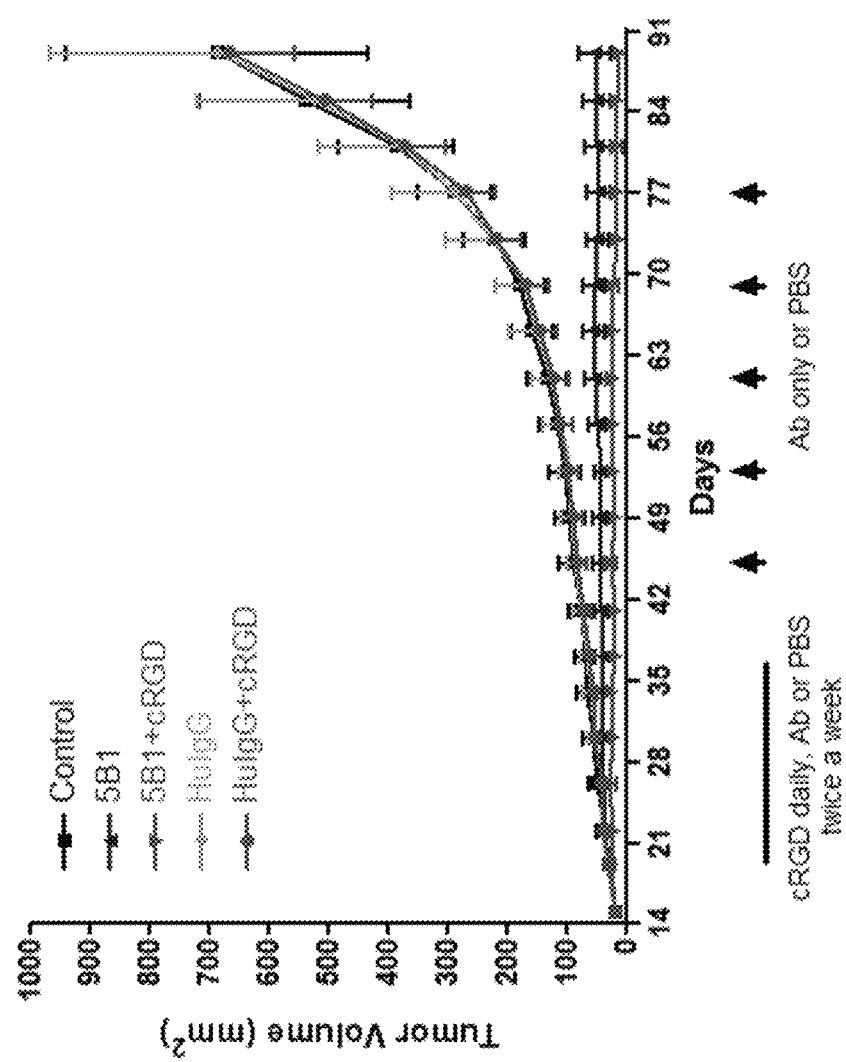

FIGS. 18A and 18B shows the anti-tumor activity in a therapeutic subcutaneous xenograft model using DMS-79 cells. FIG. 18A shows the suppression or regression of 5B1 treated mice (5B1 alone (▲) or 5B1+cRGD (▼)) in comparison to Human IgG (IgG alone (♦) or IgG+cRGD (●)) and PBS injected control (■). Arrows indicate days of antibody or PBS injections. FIG. 18B shows representative images of treated mice. Arrows indicate absence of any visual tumor.

Figure 19:
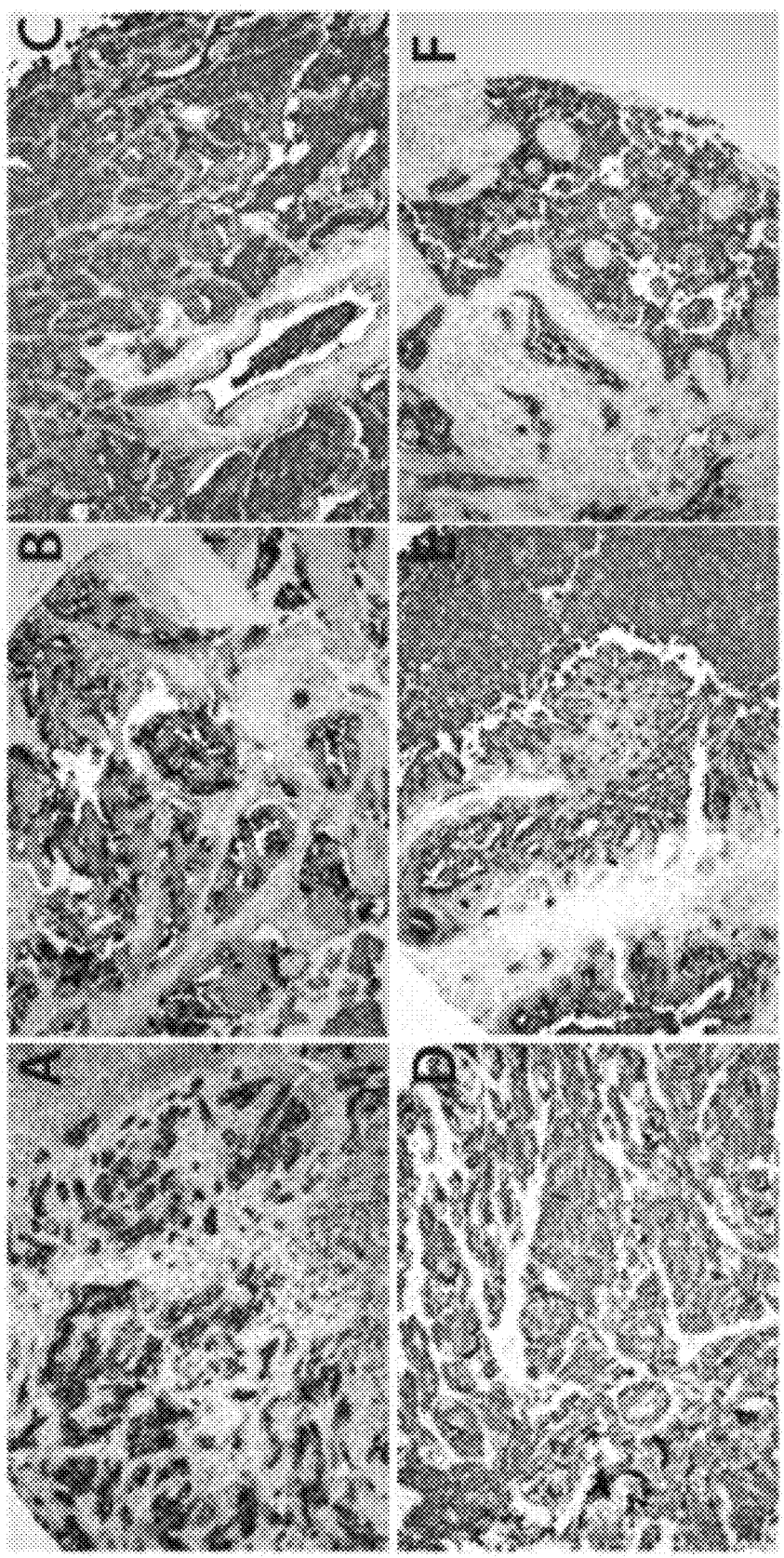

FIG. 19, panels A-F, show binding of 5B1 to various tumor types. Panel A is a pancreas, ductal adenocarcinoma, stage III tumor. Panel B is a sigmoid colon, carcinoma stage IIIB tumor. Panel C is a lung, adenocarcinoma, stage IB tumor. Panel D is a urinary bladder, mucinous adenocarcinoma, stage IV tumor. Panel E is a ovary, metastatic carcinoma from colon tumor. Panel F is a lymph node, metastatic carcinoma, stage IIIA tumor.

Figure 20:
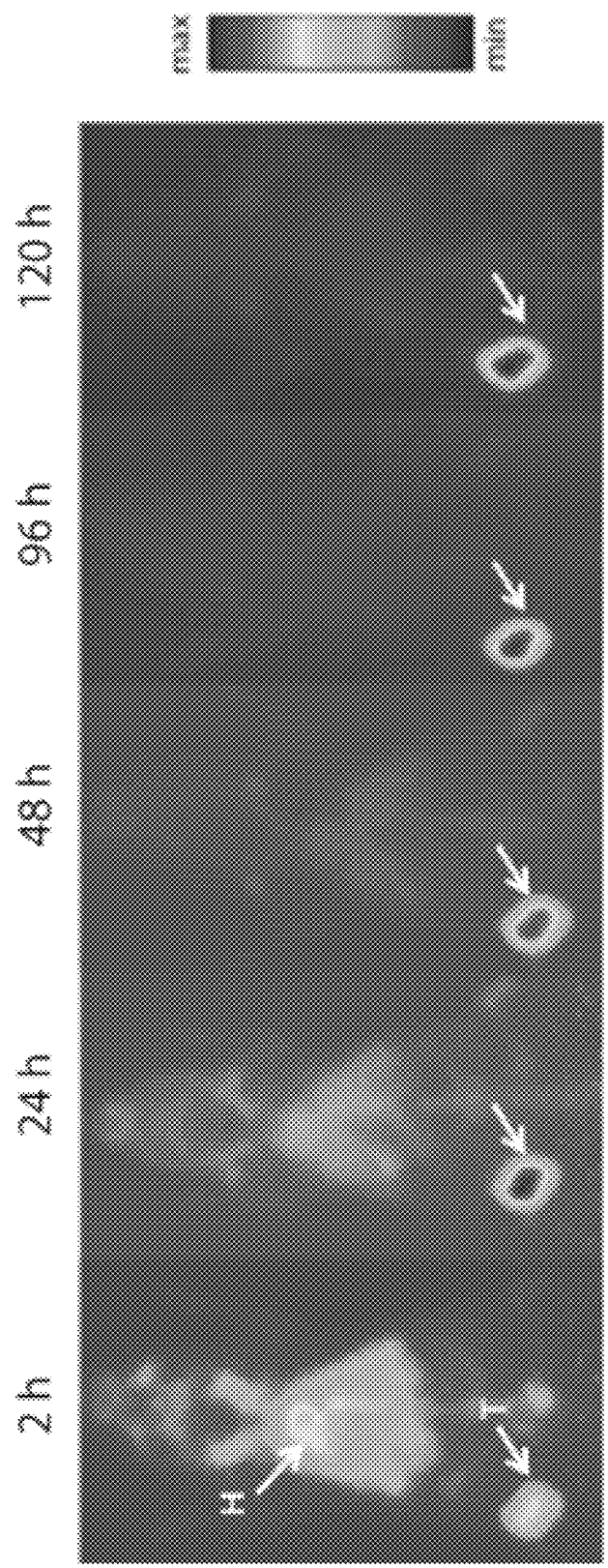

FIG. 20 shows serial PET maximum intensity projection (MIP) images acquired from 2-120 h with $^{89}$Zr radiolabed-5B1 antibody ($^{89}$Zr-5B1) intravenously administered to female SCID mice subcutaneously implanted with BxPC3 pancreatic tumors. PET-MIP imaging demonstrates high tumor uptake with clearance of non-specifically bound tracer as early as 24 hours post injection (h p.i.)

Figure 21:
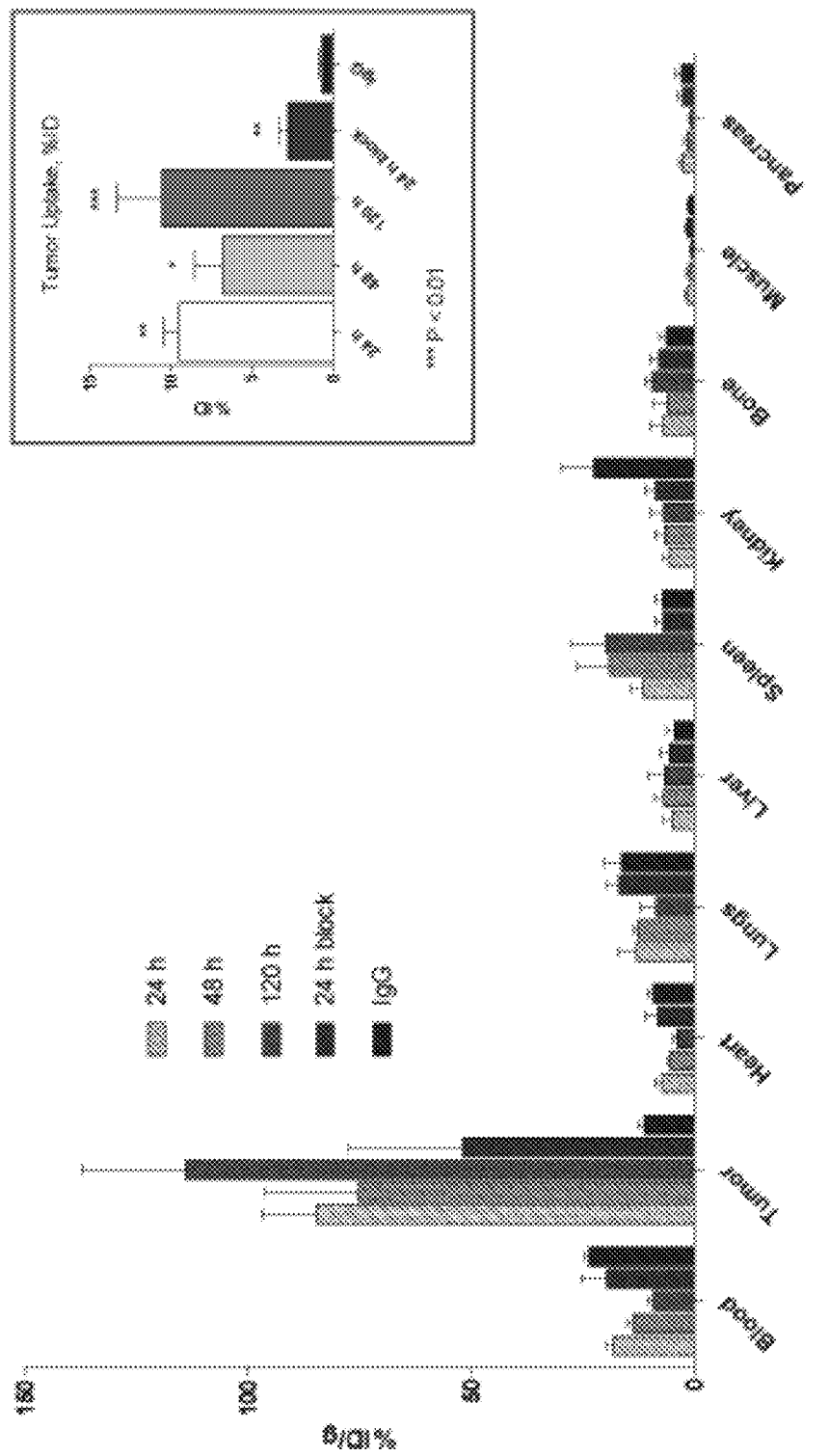

FIG. 21 shows biodistribution results that are in agreement with the PET data of FIG. 20, with an observed tumor uptake of 84.73±12.28% ID/g. Because of the small tumor weights, a plot of tumor uptake expressed as % ID versus time is displayed by the inset graph. The tumor % ID display significant tumor uptake by $^{89}$Zr-5B1 at all time points, and, is at least seven-fold greater than non-specific $^{89}$Zr-IgG. Competitive inhibition with cold 5B1 (200 μg) show a decrease in tumor accumulation.

Figure 22:
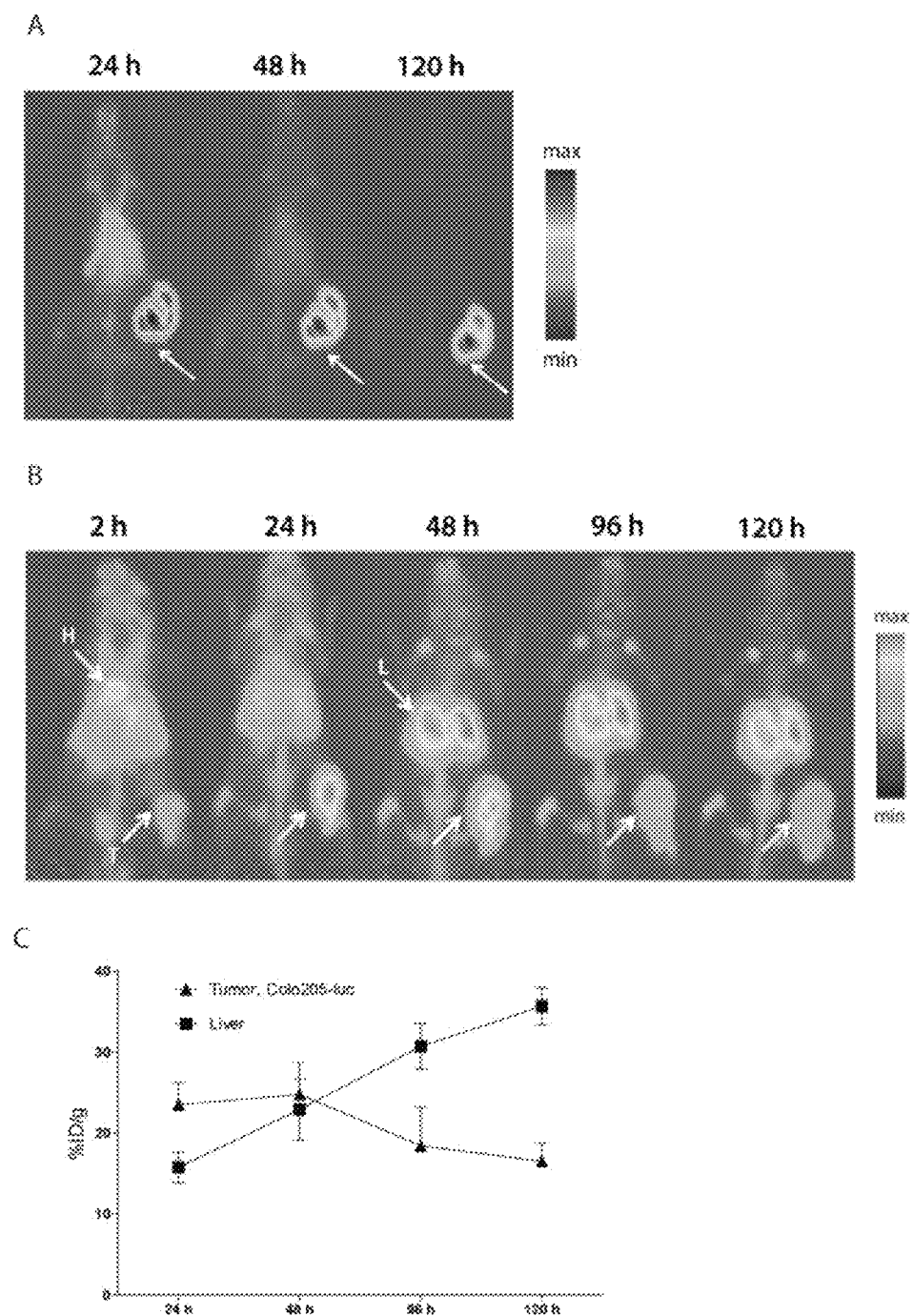

FIG. 22, panels A-C, show PET-MIP images of mice-bearing DMS79 (Panel A) and Colo205-luc xenografts (Panel B). PET-MIP imaging delineation of tumor (T), heart (H) and liver (L) by $^{89}$Zr-5B1 are indicated. The colorectal Colo205-luc xenografts model displays $^{89}$Zr-5B1 accumulation peaking at 24 h, which eventually decreases while an increase in non-specific binding to the liver was exhibited (Panel C).

Figure 23:
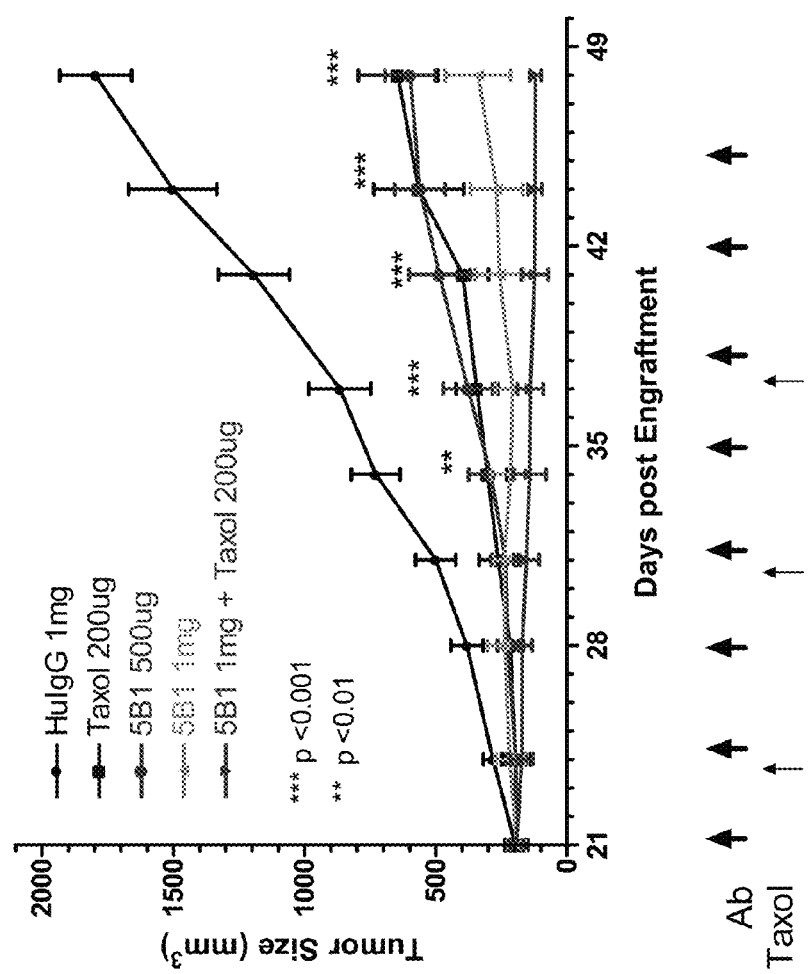

FIG. 23 shows a dose dependent inhibition and regression of tumor growth in a DMS-79 small lung cell carcinoma xenograft model treated with successive co-administration of 5B1 antibody and Taxol (Paclitaxel). Large arrows on the X axis indicate 5B1 treatment. Co-administration of 5B1 antibody and Taxol significantly limited tumor growth and resulted in tumor regression in comparison to control human IgG (HuIgG) or 5B1 antibody and Taxol administered individually. Significantly differences from control by 2-way ANOVA at p<0.01 () and p<0.001 (*) are indicated. N=5.

Figure 24:
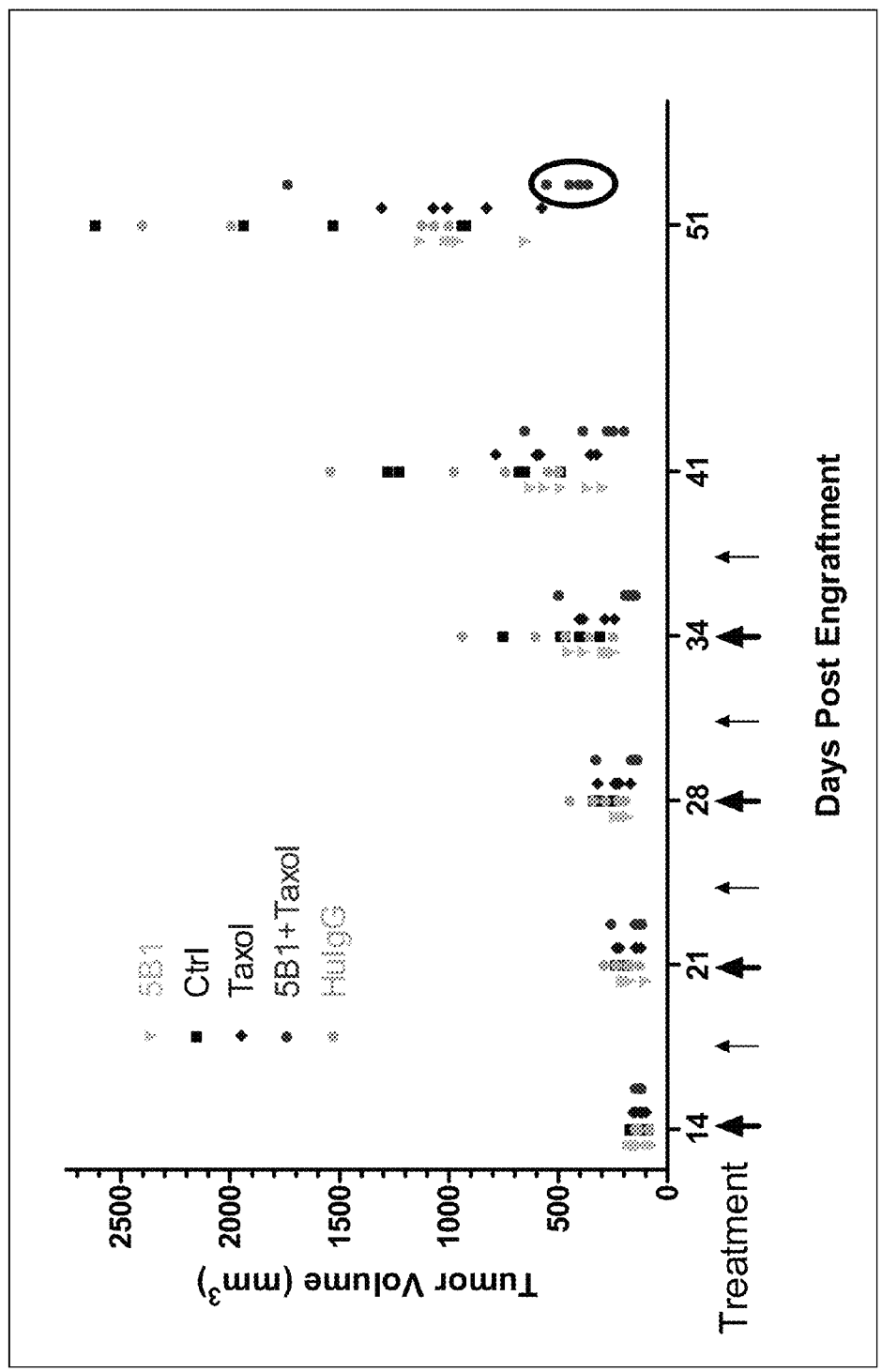

FIG. 24 shows the inhibition of tumor growth in a BxPc3 pancreatic carcinoma xenograft model treated with successive co-administration of 5B1 antibody and Taxol (Paclitaxel). Large arrows on the X axis indicate Taxol plus 5B1 treatment, whereas the small arrows indicate 5B1 alone treatment. Co-administration of 5B1 antibody and Taxol significantly limited tumor growth in comparison to controls (PBS-Ctrl; human IgG-HuIgG) or 5B1 antibody and Taxol administered individually.

Figure 25:
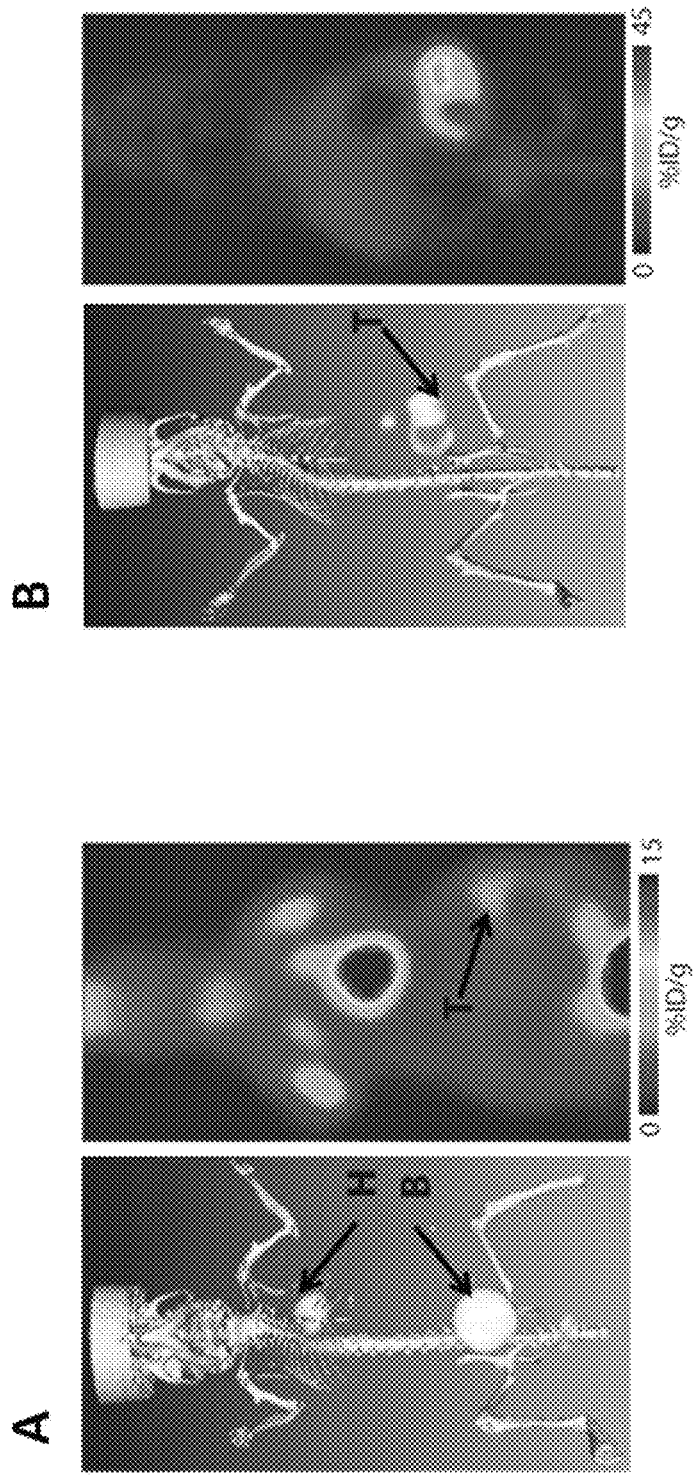

FIG. 25, panels A and B, show representative images of mice that were orthotopically transplanted with BxPC3-luc pancreatic tumor xenografts. Panel A: The co-registration of FDG-PET and computed tomography (CT) (left) and planar sections of FDG-PET only (right) displayed minimal tumor detection of the tracer with a high uptake in highly metabolic tissues (i.e. heart, H and bladder, B). Panel B: Acquired $^{89}$Zr radiolabed-5B1 antibody ($^{89}$Zr-5B1) PET image of the same mouse co-registered with CT exhibited exceptional tumor detection of the BxPC3-luc tumor xenografts.

DETAILED DESCRIPTION OF THE INVENTION

Carbohydrates expressed on the tumor cell surface can be targets for passive immunotherapy. The compositions provided herein are based, at least in part, on the identification and characterization of human antibodies that were generated from blood lymphocytes of individuals immunized with a Sialyl-Lewis$^a$-keyhole limpet hemocyanin (sLe$^a$-KLH) conjugate vaccine. At least four antibodies with high affinity for sLe$^a$ (5B1, 9H3, 5H11 and 7E3) were identified. Two of these antibodies were expressed as recombinant antibodies (r5B1 and r7E3) and further characterized in in vitro and in vivo models. Both antibodies were potent in complement-dependent cytotoxicity (CDC) assays, and the 5B1 antibody was also highly active in antibody-dependent cytotoxicity assays. The in vivo efficacy of the antibodies were tested in two xenograft models using either Colo205 tumor cells or DMS-79 tumor cells engrafted into severe combined immunodeficient (SCID) mice. The translational relevance of the invention provided herein is 2 fold: First, the approach provided herein demonstrates that the antibody response elicited by a sLe$^a$-KLH vaccine is useful as a vaccine itself Second, the most potent antibodies that were generated in a clinical trial can be preserved and ultimately used as therapeutics, or in the generation of therapeutics, for a target cancer population. The high affinity of the antibodies provided herein and their high effector functions support this translational potential.

As used herein, the term "antibody" is intended to mean a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See Borrebaeck (ed.) (1995) *Antibody Engineering*, Second Edition, Oxford University Press.; Kuby (1997) *Immunology*, Third Edition, W.H. Freeman and Company, New York). In the context of the present invention, the specific molecular antigen that can be bound by an antibody of the invention includes the target carbohydrate sLe$^a$.

The term "human" when used in reference to an antibody or a functional fragment thereof refers an antibody or functional fragment thereof that has a human variable region and/or a human constant region or a portion thereof corresponding to human germline immunoglobulin sequences. Such human germline immunoglobulin sequences are described by Kabat et al. (1991) *Sequences of Proteins of Immunological Interest*, Fifth Edition, U.S. Department of Health and Human Services, NIH Publication No. 91-3242. A human antibody, in the context of the present invention, can include an antibody that binds to sLe$^a$ and is encoded by a nucleic acid sequence that is a naturally occurring somatic variant of the human germline immunoglobulin nucleic acid sequence. Exemplary methods of producing human antibodies are provided in Example I, but any method well known to those skilled in the art can be used.

The term "monoclonal antibody" refers to an antibody that is the product of a single cell clone or hybridoma or a population of cells derived from a single cell. A monoclonal antibody also is intended to refer to an antibody produced by recombinant methods from heavy and light chain encoding immunoglobulin genes to produce a single molecular immunoglobulin species. Amino acid sequences for antibodies within a monoclonal antibody preparation are substantially homogeneous and the binding activity of antibodies within such a preparation exhibit substantially the same antigen binding activity. In contrast, polyclonal antibodies are obtained from different B cells within a population, which are a combination of immunoglobulin molecules that bind a specific antigen. Each immunoglobulin of the polyclonal antibodies can bind a different epitope of the same antigen. Methods for producing both monoclonal antibodies and polyclonal antibodies are well known in the art (Harlow and Lane., *Antibodies: A Laboratory Manual*, Cold Spring Harbor Laboratory Press (1989) and Borrebaeck (ed.), *Antibody Engineering: A Practical Guide*, W.H. Freeman and Co., Publishers, New York, pp. 103-120 (1991)).

As used herein, the term "functional fragment" when used in reference to an antibody is intended to refer to a portion of the antibody including heavy or light chain polypeptides that retains some or all of the binding activity as the antibody from which the fragment was derived. Such functional fragments can include, for example, an Fd, Fv, Fab, F(ab'), F(ab)$_2$, F(ab')$_2$, single chain Fv (scFv), diabody, triabody, tetrabody and minibody. Other functional fragments can include, for example, heavy or light chain polypeptides, variable region polypeptides or CDR polypeptides or portions thereof so long as such functional fragments retain binding activity. Such antibody binding fragments can be found described in, for example, Harlow and Lane, *Antibodies: A Laboratory Manual*, Cold Spring Harbor Laboratory, New York (1989); Myers (ed.), *Molec. Biology and Biotechnology: A Comprehensive Desk Reference*, New York: VCH Publisher, Inc.; Huston et al., *Cell Biophysics*, 22:189-224 (1993); Plückthun and Skerra, *Meth. Enzymol.*, 178:497-515 (1989) and in Day, E. D., *Advanced Immunochemistry*, Second Ed., Wiley-Liss, Inc., New York, N.Y. (1990).

The term "heavy chain" when used in reference to an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, referred to as alpha (α), delta (δ), epsilon (ε), gamma (γ) and mu (μ), based on the amino acid sequence of the heavy chain constant region. The distinct heavy chains differ in size: α, δ and γ contain approximately 450 amino acids, while μ and ε contain approximately 550 amino acids. When combined with a light chain, these distinct types of heavy chains give rise to five well known classes of antibodies, IgA, IgD, IgE, IgG and IgM, respectively, including four subclasses of IgG, namely IgG1, IgG2, IgG3 and IgG4. A heavy chain can be a human heavy chain.

The term "light chain" when used in reference to an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa (κ) of lambda (λ) based on the amino acid sequence of the constant domains. Light chain amino acid sequences are well known in the art. A light chain can be a human light chain.

The term "variable domain" or "variable region" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. Numbering of amino acid positions used herein is according to the EU Index, as in Kabat et al. (1991) *Sequences of proteins of immunological interest*. (U.S. Department of Health and Human Services, Washington, D.C.) 5$^{th}$ ed. A variable region can be a human variable region.

A CDR refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved β-sheet framework, and thus are able to adapt different conformations (Chothia and Lesk, *J. Mol. Biol.* 196:901-917 (1987)). Both terminologies are well recognized in the art. The positions of CDRs within a canonical antibody variable domain have been determined by comparison of numerous structures (Al-Lazikani et al., *J. Mol. Biol.* 273:927-948 (1997); Morea et al., *Methods* 20:267-279 (2000)). Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra (1997)). Such nomenclature is similarly well known to those skilled in the art.

For example, CDRs defined according to either the Kabat (hypervariable) or Chothia (structural) designations, are set forth in the Table 1 below.

TABLE 1

CDR Definitions

| Kabat[1] | Chothia[2] | Loop Location |
|---|---|---|
| V$_H$ CDR1 | 31-35 | 26-32 | linking B and C strands |
| V$_H$ CDR2 | 50-65 | 53-55 | linking C' and C" strands |
| V$_H$ CDR3 | 95-102 | 96-101 | linking F and G strands |
| V$_L$ CDR1 | 24-34 | 26-32 | linking B and C strands |

TABLE 1-continued

CDR Definitions

| Kabat[1] | Chothia[2] | Loop Location | |
|---|---|---|---|
| $V_L$ CDR2 | 50-56 | 50-52 | linking C' and C" strands |
| $V_L$ CDR3 | 89-97 | 91-96 | linking F and G strands |

[1]Residue numbering follows the nomenclature of Kabat et al., supra
[2]Residue numbering follows the nomenclature of Chothia et al., supra One or more CDRs also can be incorporated into a molecule either covalently or noncovalently to make it an immunoadhesin. An immunoadhesin can incorporate the CDR(s) as part of a larger polypeptide chain, can covalently link the CDR(s) to another polypeptide chain, or can incorporate the CDR(s) noncovalently. The CDRs permit the immunoadhesin to bind to a particular antigen of interest.

As used herein, the term "isolated" when used in reference to an antibody, antibody functional fragment or polynucleotide is intended to mean that the referenced molecule is free of at least one component as it is found in nature. The term includes an antibody, antibody functional fragment or polynucleotide that is removed from some or all other components as it is found in its natural environment. Components of an antibody's natural environment include, for example, erythrocytes, leukocytes, thrombocytes, plasma, proteins, nucleic acids, salts and nutrients. Components of an antibody functional fragment's or polynucleotide's natural environment include, for example, lipid membranes, cell organelles, proteins, nucleic acids, salts and nutrients. An antibody, antibody functional fragment or polynucleotide of the invention can also be free or all the way to substantially free from all of these components or any other component of the cells from which it is isolated or recombinantly produced.

As used herein, "isotype" refers to the antibody class that is encoded by heavy chain constant region genes. The heavy chains of a given antibody or functional fragment determine the class of that antibody or functional fragment: IgM, IgG, IgA, IgD or IgE. Each class can have either κ or λ light chains. The term "subclass" refers to the minor differences in amino acid sequences of the heavy chains that differentiate the subclasses. In humans there are two subclasses of IgA (subclasses IgA1 and IgA2) and there are four subclasses of IgG (subclasses IgG1, IgG2, IgG3 and IgG4). Such classes and subclasses are well known to those skilled in art.

The terms "binds" or "binding" as used herein refer to an interaction between molecules to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions or forces. Binding of an antibody or functional fragment thereof can be detected using, for example, an enzyme-linked immunosorbant assay, a method provided in Example I or any one of a number of methods that are well known to those skilled in the art.

The strength of the total non-covalent interactions between a single antigen-binding site on an antibody or functional fragment and a single epitope of a target molecule, such as sLe$^a$, is the affinity of the antibody or functional fragment for that epitope. The ratio of association ($k_1$) to dissociation ($k_{-1}$) of an antibody or functional fragment thereof to a monovalent antigen ($k_1/k_{-1}$) is the association constant K, which is a measure of affinity. The value of K varies for different complexes of antibody or functional fragment and antigen and depends on both $k_1$ and $k_{-1}$. The association constant K for an antibody or functional fragment of the invention can be determined using any method provided herein or any other method well known to those skilled in the art.

The affinity at one binding site does not always reflect the true strength of the interaction between an antibody or functional fragment and an antigen. When complex antigens containing multiple, repeating antigenic determinants, such as a polyvalent sLe$^a$, come in contact with antibodies containing multiple binding sites, the interaction of antibody or functional fragment with antigen at one site will increase the probability of a reaction at a second site. The strength of such multiple interactions between a multivalent antibody and antigen is called the avidity. The avidity of an antibody or functional fragment can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

The specificity of an antibody or functional fragment thereof refers to the ability of an individual antibody or functional fragment thereof to react with only one antigen. An antibody or functional fragment can be considered specific when it can distinguish differences in the primary, secondary or tertiary structure of an antigen or isomeric forms of an antigen.

The term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. Thus, the terms "nucleotide sequence" or "nucleic acid sequence" is the alphabetical representation of a polynucleotide. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. Polynucleotide also refers to both double- and single-stranded molecules. Unless otherwise specified or required, any embodiment of this invention that is a polynucleotide encompasses both the double-stranded form and each of two complementary single-stranded forms known or predicted to make up the double-stranded form. It is understood that the isolated polynucleotides and nucleic acids described herein are directed to non-naturally occurring polynucleotides and nucleic acids. Non-naturally occurring polynucleotides and nucleic acids can include, but are not limited to, cDNA and chemically synthesized molecules.

The term "encode" or grammatical equivalents thereof as it is used in reference to polynucleotides refers to a polynucleotide in its native state or when manipulated by methods well known to those skilled in the art that can be transcribed to produce mRNA, which is then translated into a polypeptide and/or a fragment thereof. The antisense strand is the complement of such a polynucleotide, and the encoding sequence can be deduced therefrom.

The phrase "therapeutic agent" refers to any agent that can be used in the treatment, management or amelioration of a disease associated with expression of sLe$^a$ and/or a symptom related thereto. In certain embodiments, a therapeutic agent refers to an antibody or functional fragment of the invention. In other embodiments, a therapeutic agent refers to an agent other than an antibody or functional fragment of the invention. A therapeutic agent can be an agent which is well known to be useful for, or has been or is currently being used for the treatment, management or amelioration of a disease associated with expression of sLe$^a$ and/or one or more symptoms related thereto.

The phrase "diagnostic agent" refers to a substance administered to a subject that aids in the diagnosis of a disease. Such substances can be used to reveal, pinpoint, and/or define the localization of a disease causing process. In certain embodiments, a diagnostic agent includes a substance that is conjugated to an antibody or functional fragment of the invention, that when administered to a subject or contacted to a sample from a subject aids in the diagnosis of cancer or tumor formation.

The phrase "detectable agent" refers to a substance that can be used to ascertain the existence or presence of a desired molecule, such as an antibody or functional fragment of the invention, in a sample or subject. A detectable agent can be a substance that is capable of being visualized or a substance that is otherwise able to be determined and/or measured (e.g., by quantitation).

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the agent, the route of administration, etc.

The phrase "therapeutically effective amount" as used herein refers to the amount of a therapeutic agent (e.g., an antibody or functional fragment provided herein or any other therapeutic agent provided herein) which is sufficient to reduce and/or ameliorate the severity and/or duration of a given disease and/or a symptom related thereto. A therapeutically effective amount of a therapeutic agent can be an amount necessary for the reduction or amelioration of the advancement or progression of a given disease, reduction or amelioration of the recurrence, development or onset of a given disease, and/or to improve or enhance the prophylactic or therapeutic effect of another therapy (e.g., a therapy other than the administration of an antibody or functional fragment provided herein).

The compound "Sialyl-Lewis$^a$" (sLe$^a$), also known as sialyl Le$^a$, Sialyl-Lewis A, Sialylated Lewis a and CA 19.9, is a tetrasaccharide with a molecular formula of $C_{31}H_{52}N_2O_{23}$ and a molar mass of 820.74 g/mol. The structure of sLe$^a$ can include Neu5Acα2-3Galβ1-3(Fucα1-4)GlcNAcβ and Neu5Gcα2-3Galβ1-3(Fucα1-4)GlcNAcβ. sLe$^a$ is widely expressed on tumors of the gastrointestinal tract and is used as a tumor marker in pancreatic and colon cancer. sLe$^a$ is also a known ligand for E-selection, also known as endothelial leukocyte adhesion molecule (ELAM).

In some embodiments, the present invention provides an isolated polynucleotide encoding an antibody heavy or light chain or a functional fragment thereof, wherein an antibody or functional fragment thereof generated using the antibody heavy or light chain binds to sLe$^a$. Accordingly, in some embodiments, the invention provides an isolated polynucleotide encoding an antibody or a functional fragment thereof, wherein the antibody includes a VH domain that has an amino acid sequence selected from the group consisting of residues 20-142 of SEQ ID NO: 2, residues 20-142 of SEQ ID NO: 6, residues 20-142 of SEQ ID NO: 10, and residues 20-145 of SEQ ID NO: 14. The isolated polynucleotide of the invention can also include a nucleic acid sequence of residues 58-426 of SEQ ID NO: 1, residues 58-426 of SEQ ID NO: 5, residues 58-426 of SEQ ID NO: 9 or residues 58-435 of SEQ ID NO: 13, wherein the nucleic acid sequence encodes the VH domain of the antibody or functional fragment thereof.

In another embodiment of the invention, the isolated polynucleotide can encode an antibody or a functional fragment thereof, wherein the antibody includes a VL domain that has an amino acid sequence selected from the group consisting of residues 20-130 of SEQ ID NO: 4, residues 20-129 of SEQ ID NO: 8, residues 20-130 of SEQ ID NO: 12, and residues 23-130 of SEQ ID NO: 16. The isolated polynucleotide of the invention can also include a nucleic acid sequence of residues 58-390 of SEQ ID NO: 3, residues 58-387 of SEQ ID NO: 7, residues 58-390 of SEQ ID NO: 11 or residues 67-390 of SEQ ID NO: 15, wherein the nucleic acid sequence encodes the VL domain of the antibody or functional fragment thereof.

In another embodiment, the invention provides an isolated polynucleotide encoding an antibody heavy or light chain or a functional fragment thereof, wherein the antibody heavy or light chain or functional fragment thereof encoded by the polynucleotide of the invention has one or more of the complementarity determining regions (CDRs) depicted in FIGS. 1-8 or listed in Table 2. An antibody or functional fragment thereof that includes one or more of the CDRs can specifically bind to sLe$^a$ as described herein. Specific binding to sLe$^a$ can include the specificity, affinity and/or avidity as provided in Example I for any of the antibodies provided herein. In another aspect, an antibody or functional fragment thereof encoded by the polynucleotides of the invention can include the complement dependent cytotoxicity (CDC) activity and/or antibody-dependent cell-mediated cytotoxicity (ADCC) activity of any one of the clonal isolates 5B1, 9H3, 5H11 or 7E3 described herein. Methods for assessing the specificity, affinity and/or avidity of an antibody or functional fragment thereof are well known in the art and exemplary methods are provided herein.

TABLE 2

CDRs of Clonal Isolates

| Variable Domain | Nucleic Acid Residues (SEQ ID NO:) | | | Amino Acid Residues (SEQ ID NO:) | | |
|---|---|---|---|---|---|---|
| | CDR1 | CDR2 | CDR3 | CDR1 | CDR2 | CDR3 |
| 5B1 VH | 133-156 (NO: 1) | 208-231 (NO: 1) | 346-393 (NO: 1) | 55-62 (NO: 2) | 70-77 (NO: 2) | 116-131 (NO: 2) |
| 5B1 VL | 133-156 (NO: 3) | 208-216 (NO: 3) | 325-360 (NO: 3) | 45-52 (NO: 4) | 70-72 (NO: 4) | 109-120 (NO: 4) |
| 9H3 VH | 133-156 (NO: 5) | 208-231 (NO: 5) | 346-393 (NO: 5) | 45-52 (NO: 6) | 70-77 (NO: 6) | 116-131 (NO: 6) |
| 9H3 VL | 133-156 (NO: 7) | 208-216 (NO: 7) | 325-357 (NO: 7) | 45-52 (NO: 8) | 70-72 (NO: 8) | 109-119 (NO: 8) |
| 5H11 VH | 133-156 (NO: 9) | 208-231 (NO: 9) | 346-393 (NO: 9) | 45-52 (NO: 10) | 70-77 (NO: 10) | 116-131 (NO: 10) |
| 5H11 VL | 134-156 (NO: 11) | 208-216 (NO: 11) | 325-360 (NO: 11) | 45-52 (NO: 12) | 70-72 (NO: 12) | 109-120 (NO: 12) |
| 7E3 VH | 133-156 (NO: 13) | 208-231 (NO: 13) | 346-402 (NO: 13) | 45-52 (NO: 13) | 70-77 (NO: 13) | 116-134 (NO: 14) |

TABLE 2-continued

CDRs of Clonal Isolates

| Variable Domain | Nucleic Acid Residues (SEQ ID NO:) | | | Amino Acid Residues (SEQ ID NO:) | | |
|---|---|---|---|---|---|---|
| | CDR1 | CDR2 | CDR3 | CDR1 | CDR2 | CDR3 |
| 7E3 VK | 145-162 (NO: 15) | 214-222 (NO: 15) | 331-360 (NO: 15) | 49-53 (NO: 16) | 72-74 (NO: 16) | 111-120 (NO: 16) |

In some embodiments, the antibody or functional fragment thereof of the invention includes less than six CDRs. In some embodiments, the antibody or functional fragment thereof includes one, two, three, four, or five CDRs selected from the group consisting of VH CDR1, VH CDR2, VH CDR3, VL CDR1, VL CDR2, and/or VL CDR3. In specific embodiments, the antibody or functional fragment thereof includes one, two, three, four, or five CDRs selected from the group consisting of VH CDR1, VH CDR2, VH CDR3, VL CDR1, VL CDR2, and/or VL CDR3 of clonal isolates 5B1, 9H3, 5H11 or 7E3 described herein.

In some embodiments, the invention provides an isolated polynucleotide that encodes an antibody or functional fragment thereof, wherein the antibody or functional fragment includes a variable heavy (VH) chain domain having the CDR1, CDR2 and CDR3 amino acid sequence of the clonal isolate 5B1, 9H3, 5H11 or 7E3. Such VH domains can include the amino acid residues 55-62, 70-77 and 116-131 of SEQ ID NO: 2, or alternatively the amino acid residues 45-52, 70-77 and 116-131 of SEQ ID NO: 6, or alternatively the amino acid residues 45-52, 70-77 and 116-131 of SEQ ID NO: 10, or alternatively the amino acid residues 45-52, 70-77 and 116-134 of SEQ ID NO: 14. In another aspect, the nucleotide sequence encoding the CDR1, CDR2 and CDR3 of the VH domain can respectively include the nucleotide sequence of residues 133-156, 208-231 and 346-393 of SEQ ID NO: 1, or alternatively the nucleotide sequence of residues 133-156, 208-231 and 346-393 of SEQ ID NO: 5, or alternatively the nucleotide sequence of residues 133-156, 208-231 and 346-393 of SEQ ID NO: 9, or alternatively the nucleotide sequence of residues 133-156, 208-231, 346-402 of SEQ ID NO: 13.

In another embodiment, the invention provides an isolated polynucleotide encoding an antibody or functional fragment thereof, wherein the antibody includes a variable light (VL) chain domain having the CDR1, CDR2 and CDR3 amino acid sequence of the clonal isolate 5B1, 9H3, 5H11 or 7E3. Such VL domain can include the amino acid residues 45-52, 70-72 and 109-120 of SEQ ID NO: 4, or alternatively the amino acid residues 45-52, 70-72 and 109-119 of SEQ ID NO: 8, or alternatively the amino acid residues 45-52, 70-72 and 109-120 of SEQ ID NO: 12, or alternatively the amino acid residues 49-53, 72-74 and 111-120 of SEQ ID NO: 16. In another aspect, the nucleotide sequence encoding the CDR1, CDR2 and CDR3 of the VH domain can respectively include the nucleotide sequence of residues 133-156, 208-216 and 325-360 of SEQ ID NO: 3, or alternatively the nucleotide sequence of residues 133-156, 208-216 and 325-357 of SEQ ID NO: 7, or alternatively the nucleotide sequence of residues 134-156, 208-216 and 325-360 of SEQ ID NO: 11, or alternatively the nucleotide sequence of residues 145-162, 214-222 and 331-360 of SEQ ID NO: 15

In another embodiment, the invention provides a variant of the polynucleotides provided herein. A variant when used in reference to a polynucleotide includes a polynucleotide having one or more modified nucleotides, such as, but not limited to, a methylated nucleotide or a nucleotide analog. Additionally, a variant polynucleotide can include a polynucleotide that is interrupted by non-nucleotide components. Modifications to a polynucleotide can be imparted before or after assembly of the polynucleotide using methods well known to those skilled in the art. For example, a polynucleotide can be modified after polymerization by conjugation with a labeling component using either enzymatic or chemical techniques (e.g., as described in Gottfried and Weinhold, 2011, Biochem. Soc. Trans., 39(2):523-628; Paredes et al., 2011, Methods, 54(2):251-259).

The polynucleotides can be obtained, and the nucleotide sequence of the polynucleotides determined, by any method well known in the art. Since the amino acid sequences of the variable heavy and light chain domains of 5B1, 9H3, 5H11 and 7E3 are known (see, e.g., SEQ ID NOS: 2, 4, 6, 8, 10, 12, 14 and 16), nucleotide sequences encoding antibodies and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, fragments, or variants thereof, annealing and ligating of those oligonucleotides, and then amplification of the ligated oligonucleotides by PCR.

A polynucleotide encoding an antibody or a functional fragment thereof of the invention can be generated using the nucleic acid sequence of the variable heavy and/or light chain domains of isolates 5B1, 9H3, 5H11 or 7E3 (e.g., SEQ ID NOS: 1, 3, 5, 7, 9, 11, 13 and 15). A nucleic acid encoding the antibody or functional fragment can be chemically synthesized or obtained from a suitable source (e.g., cDNA isolated from cells expressing the antibody or functional fragment thereof, such as hybridoma cells selected to express the antibody or functional fragment thereof) by PCR amplification using synthetic primers hybridizable to the 3' and 5' ends of the sequence or by cloning using an oligonucleotide probe specific for the particular nucleic acid sequence. Amplified nucleic acids generated by PCR can then be cloned into replicable cloning vectors using any method well known in the art.

In some embodiments, the present invention provides an isolated antibody or functional fragment thereof, wherein the antibody binds to sLe$^a$. Accordingly, in some aspects, the invention provides an isolated antibody or functional fragment thereof that binds to sLe$^a$, wherein the antibody or functional fragment thereof includes a VH domain having an amino acid sequence selected from the group consisting of residues 20-142 of SEQ ID NO: 2, residues 20-142 of SEQ ID NO: 6, residues 20-142 of SEQ ID NO: 10, and residues 20-145 of SEQ ID NO: 14.

In some embodiments, the invention provides an isolated antibody or functional fragment thereof that binds to sLe$^a$, wherein the antibody or functional fragment thereof includes a VL domain having an amino acid sequence selected from the group consisting of residues 20-130 of SEQ ID NO: 4, residues 20-129 of SEQ ID NO: 8, residues 20-130 of SEQ ID NO: 12, and residues 23-130 of SEQ ID NO: 16.

In some embodiments, the invention provides an isolated antibody or functional fragment thereof that binds to sLe$^a$, wherein the antibody or functional fragment thereof includes both a VH domain and a VL domain, where the VH domain and the VL domain respectively include an amino acid sequence selected from the group consisting of residues 20-142 of SEQ ID NO: 2 and residues 20-130 of SEQ ID NO: 4; residues 20-142 of SEQ ID NO: 6 and residues 20-129 of SEQ ID NO: 8; residues 20-142 of SEQ ID NO: 10 and residues 20-130 of SEQ ID NO: 12; and residues 20-145 of SEQ ID NO: 14 and residues 23-130 of SEQ ID NO: 16.

In some embodiments, in order to bind sLe$^a$, the antibody or functional fragment thereof of the invention has one or more of the CDRs depicted in FIGS. 1-8 or listed in Table 2. An antibody or functional fragment thereof that includes one or more of the CDRs, in particular CDR3, can specifically bind to sLe$^a$ as described herein. Specific binding to sLe$^a$ can include the specificity and affinity as provided in Example I for any of the antibodies provided herein. In some aspects, an antibody or functional fragment thereof of the invention can include the CDC activity and/or ADCC activity of any one of the clonal isolates 5B1, 9H3, 5H11 or 7E3 described herein.

In some embodiments, the invention provides an isolated antibody or functional fragment thereof, wherein the antibody includes a VH chain domain having the CDR1, CDR2 and CDR3 amino acid sequence of the clonal isolate 5B1, 9H3, 5H11 or 7E3. Such VH domains can include the amino acid residues 55-62, 70-77 and 116-131 of SEQ ID NO: 2, or alternatively the amino acid residues 45-52, 70-77 and 116-131 of SEQ ID NO: 6, or alternatively the amino acid residues 45-52, 70-77 and 116-131 of SEQ ID NO: 10, or alternatively the amino acid residues 45-52, 70-77 and 116-134 of SEQ ID NO: 14.

In some embodiments, the invention provides an isolated antibody or functional fragment thereof, wherein the antibody includes a VL chain domain having the CDR1, CDR2 and CDR3 amino acid sequence of the clonal isolate 5B1, 9H3, 5H11 or 7E3. Such VL domain can include the amino acid residues 45-52, 70-72 and 109-120 of SEQ ID NO: 4, or alternatively the amino acid residues 45-52, 70-72 and 109-119 of SEQ ID NO: 8, or alternatively the amino acid residues 45-52, 70-72 and 109-120 of SEQ ID NO: 12, or alternatively the amino acid residues 49-53, 72-74 and 111-120 of SEQ ID NO: 16.

In some aspects of the invention, the isolated antibody or functional fragment thereof is a monoclonal antibody. In some aspects of the invention, the isolated antibody or functional fragment thereof provided herein is an IgG or IgM isotype. In a further aspect of the invention, the antibody or function fragment thereof is an antibody of the IgG1 subclass.

In some embodiments, the antibody functional fragment of the invention can be, but is not limited to, a Fab, a Fab', a F(ab')$_2$, a Fabc, a scFV, a diabody, a triabody, minibody or a single-domain antibody (sdAB). In some aspects, the invention provides a diabody that includes the amino acid sequence of SEQ ID NO: 18 or 20. Such diabodies of the invention can be, in some aspects, encoded by a polynucleotide having the nucleic acid sequence of SEQ ID NO: 17 or 19. With respect to antibodies and functional fragments thereof, various forms, alterations and modifications are well known in the art. The sLe$^a$ specific antibody fragments of the invention can include any of such various antibody forms, alterations and modifications. Examples of such various forms and terms as they are known in the art are set forth below.

In some embodiments, the invention provides a method of producing an antibody or functional fragment thereof of the invention. The method of the invention can include introducing a polynucleotide of the invention into a host cell, culturing the host cell under conditions and for a sufficient period of time to produce the encoded heavy and/or light chain of an antibody or functional fragment of the invention, and purifying the heavy and/or light chain of an antibody or functional fragment.

Recombinant expression of an antibody or functional fragment thereof of the invention that binds to a sLe$^a$ antigen can include construction of an expression vector containing a polynucleotide that encodes the heavy and/or light chain of an antibody or functional fragment of the invention. Once a polynucleotide encoding an antibody or functional fragment thereof (preferably, but not necessarily, containing the heavy and/or light chain variable domain) of the invention has been obtained, the vector for the production of the antibody or functional fragment can be produced by recombinant DNA technology using techniques well known in the art. Methods for preparing a protein by expressing a polynucleotide containing an antibody or a functional fragment thereof encoding nucleotide sequence are described herein.

Methods which are well known to those skilled in the art can be used to construct expression vectors containing antibody or functional fragments thereof coding sequences and appropriate transcriptional and translational control signals. These methods include, for example, in vitro recombinant DNA techniques, synthetic techniques, and in vivo genetic recombination. The invention, thus, provides replicable vectors including a nucleotide sequence encoding an antibody or functional fragment thereof of the invention operably linked to a promoter. Such vectors can include the nucleotide sequence encoding the constant region of the antibody molecule (see, e.g., International Publication Nos. WO 86/05807 and WO 89/01036; and U.S. Pat. No. 5,122,464) and the variable domain of the antibody can be cloned into such a vector for expression of the entire heavy, the entire light chain, or both the entire heavy and light chains.

The expression vector can be transferred to a host cell by conventional techniques and the transfected cells are then cultured by conventional techniques to produce an antibody or functional fragment thereof of the invention. Thus, the invention includes host cells containing a polynucleotide encoding an antibody or functional fragment thereof of the invention operably linked to a heterologous promoter. In some embodiments for the expression of double-chained antibodies, vectors encoding both the heavy and light chains can be co-expressed in the host cell for expression of the entire immunoglobulin molecule, as detailed below.

A variety of host-expression vector systems can be utilized to express the antibody or functional fragments thereof of the invention (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In some aspects, bacterial cells such as *Escherichia coli*, or eukaryotic cells, especially for the expression of whole recombinant antibody, are used for the expression of a recombinant antibody or functional fragment. For example, mammalian cells such as Chinese hamster ovary cells (CHO), in conjunction with a vector such as the major intermediate early gene promoter element from human cytomegalovirus is an effective expression system for antibodies (Foecking et al., 1986, *Gene* 45:101; and Cockett et al., 1990, *Bio/Technology* 8:2). In some embodiments, antibodies or fragments thereof of the invention are produced in CHO cells. In one embodiment, the expression of nucleotide sequences encoding antibodies or functional fragments thereof of the invention which bind to sLe$^a$ is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruther et al., 1983, *EMBO* 12:1791), in which the antibody coding sequence can be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody or functional fragment coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, *Proc. Natl. Acad. Sci. USA* 8 1:355-359). Specific initiation signals can also be used for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, *Methods in Enzymol.* 153:51-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the antibody or functional fragment. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

For long-term, high-yield production of recombinant proteins, stable expression is preferred. For example, cell lines which stably express the antibody or functional fragment of the invention can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the antibody molecule.

A number of selection systems can be used, including but not limited to, the herpes simplex virus thymidine kinase (Wigler et al., 1977, *Cell* 11:223), hypoxanthineguanine phosphoribosyltransferase (Szybalska & Szybalski, 1992, *Proc. Natl. Acad. Sci. USA* 48:202), and adenine phosphoribosyltransferase (Lowy et al., 1980, *Cell* 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, *Proc. Natl. Acad. Sci. USA* 77(6):3567-70; O'Hare et al., 1981, *Proc. Natl. Acad. Sci. USA* 78:1527); glutamine synthetase (GS), which is an enzyme responsible for the biosynthesis of glutamine using glutamate and ammonia (Bebbington et al., 1992, *Biuotechnology* 10:169); gpt, which confers resistance to mycophenolic acid (Mulligan & Berg, 1981, *Proc. Natl. Acad. Sci. USA* 78:2072); neo, which confers resistance to the aminoglycoside G-418 (Wu and Wu, 1991, *Biotherapy*

3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, TIB TECH 11(5):155-215); and hygro, which confers resistance to hygromycin (Santerre et al., 1984, *Gene* 30:147). Methods well known in the art of recombinant DNA technology can be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds.), *Current Protocols in Human Genetics*, John Wiley & Sons, NY (1994); Colberre-Garapin et al., 1981, *J. Mol. Biol.* 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing an antibody or functional fragment thereof is amplifiable, increase in the level of inhibitor present in culture of host cell will increase the number of copies of the marker gene. Since the amplified region is associated with the antibody gene, production of the antibody will also increase (Crouse et al., 1983, *Mol. Cell. Biol.* 3:257).

The host cell can be co-transfected with two expression vectors of the invention, the first vector encoding a heavy chain derived polypeptide and the second vector encoding a light chain derived polypeptide. The two vectors can contain identical selectable markers which enable equal expression of heavy and light chain polypeptides. Alternatively, a single vector can be used which encodes, and is capable of expressing, both heavy and light chain polypeptides. In such situations, the light chain can be placed before the heavy chain to avoid an excess of toxic free heavy chain (Proudfoot, 1986, *Nature* 322:52; and Kohler, 1980, *Proc. Natl. Acad. Sci. USA* 77:2197-2199). The coding sequences for the heavy and light chains can include cDNA or genomic DNA.

Additionally, polynucleotides encoding the heavy and/or light chains of the antibody or functional fragment of the invention can be subjected to codon optimization using techniques well known in the art to achieve optimized expression of an antibody or functional fragment of the invention in a desired host cell. For example, in one method of codon optimization, a native codon is substituted by the most frequent codon from a reference set of genes, wherein the rate of codon translation for each amino acid is designed to be high. Additional exemplary methods for generating codon optimized polynucleotides for expression of a desired protein, which can be applied to the heavy and/or light chains of the antibody or functional fragment of the invention, are described in Kanaya et al., *Gene*, 238:143-155 (1999), Wang et al., *Mol. Biol. Evol.*, 18(5):792-800 (2001), U.S. Pat. No. 5,795,737, U.S. Publication 2008/0076161 and WO 2008/000632.

Once an antibody molecule of the invention has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or functional fragments of the present invention can be fused to heterologous polypeptide sequences provided herein or otherwise known in the art to facilitate purification. For example, an antibody or functional fragment of the invention can be purified through recombinantly adding a poly-histidine tag (His-tag), FLAG-tag, hemagglutinin tag (HA-tag) or myc-tag among others that are commercially available and utilizing purification methods well known to those skilled in the art.

A Fab fragment refers to a monovalent fragment consisting of the VL, VH, CL and CH1 domains; a F(ab')$_2$ fragment is a bivalent fragment including two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., *Nature* 341:544-546, (1989)) consists of a VH domain.

An antibody can have one or more binding sites. If there is more than one binding site, the binding sites can be identical to one another or can be different. For example, a naturally occurring immunoglobulin has two identical binding sites, a single-chain antibody or Fab fragment has one binding site, while a "bispecific" or "bifunctional" antibody has two different binding sites.

A single-chain antibody (scFv) refers to an antibody in which a VL and a VH region are joined via a linker (e.g., a synthetic sequence of amino acid residues) to form a continuous polypeptide chain wherein the linker is long enough to allow the protein chain to fold back on itself and form a monovalent antigen binding site (see, e.g., Bird et al., *Science* 242:423-26 (1988) and Huston et al., *Proc. Natl. Acad. Sci. USA* 85:5879-83 (1988)). Diabodies refer to bivalent antibodies including two polypeptide chains, wherein each polypeptide chain includes VH and VL domains joined by a linker that is too short to allow for pairing between two domains on the same chain, thus allowing each domain to pair with a complementary domain on another polypeptide chain (see, e.g., Holliger et al., *Proc. Natl. Acad. Sci. USA* 90:6444-48 (1993), and Poljak et al., *Structure* 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies including three and four polypeptide chains, respectively, and forming three and four antigen binding sites, respectively, which can be the same or different.

The present invention also provides an antibody or functional fragment thereof derivative of 5B1, 9H3, 5H11 and/or 7E3, wherein the antibody or functional fragment binds to sLe$^a$. Standard techniques well known to those of skill in the art can be used to introduce mutations in the nucleotide sequence encoding an antibody or functional fragment thereof of the invention, including, for example, site-directed mutagenesis and PCR-mediated mutagenesis which results in amino acid substitutions. In some aspects, the derivative includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule.

In some embodiments, the invention provides an antibody or functional fragment thereof having modified forms of naturally occurring amino acids, conservative substitutions, non-naturally occurring amino acids, amino acid analogues and mimetics so long as such the antibody or functional fragment retains functional activity as defined herein. In one embodiment, the derivative has conservative amino acid substitutions that are made at one or more predicted non-essential amino acid residues. A conservative amino acid substitution is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded antibody or functional fragment thereof can be expressed and the activity of the antibody or functional fragment can be determined.

In some embodiments, the invention provides an antibody or functional fragment thereof having modified fucosylation, galactosylation and/or sialylation of an Fc fragment contained within an antibody or functional fragment of the invention. Such modifications of an Fc fragment can effect Fc receptor-mediated activity as discussed in Peipp et al., *Blood*, 112(6):2390-2399 (2008). For example, glycoengineered therapeutic antibodies lacking core fucose residues from the Fc N-glycans exhibit strong ADCC at lower concentrations with much higher efficacy compared to fucosylated counterparts. Shields et al., *J. Biol. Chem.*, 277(30): 26733-40 (2002); Okazaki et al., *J Mol Biol.*, 336:1239-1249 (2004); Natsume et al., *J. Immunol. Methods.*, 306:93-103 (2005). Methods for modifying the fucosylation, galactosylation and/or sialylation of an antibody for functional fragment thereof are well known in the art. For example, defucosylation approaches can be grouped into three methodologies (1) conversion of the N-glycosylation pathway of nonmammalian cells to the 'humanized' non-fucosylation pathway; (2) inactivation of the N-glycan fucosylation pathway of mammalian cells and (3) in vitro chemical synthesis of non-fucosylated N-glycoprotein or enzymatic modification of N-glycans to non-fucosylated forms, as described in Yamane-Ohnuki et al., MAbs., 1(3):230-236 (2009). It is understood that any one of these methods or any other method that is well known in the art can be used to produce an antibody or functional fragment thereof having modified fucosylation, galactosylation and/or sialylation.

Antibodies or functional fragments thereof of the invention that bind to sLe$^a$ can be produced by any method known in the art for the synthesis of antibodies, in particular, by chemical synthesis or by recombinant expression techniques. The practice of the invention employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press; Borrebaeck (ed.) (1995) *Antibody Engineering*, Second Edition, Oxford University Press; Lo (ed.) (2006) *Antibody Engineering: Methods and Protocols* (Methods in Molecular Biology); Vol. 248, Humana Press, Inc; each of which is incorporated herein by reference in its entirety.

Monoclonal antibodies can be prepared using a wide variety of techniques known in the art including the use of hybridoma and recombinant technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981), each of which is incorporated herein by reference in its entirety. A monoclonal antibody is not limited to antibodies produced through hybridoma technology. Other exemplary methods of producing monoclonal antibodies are known in the art. Additional exemplary methods of producing monoclonal antibodies are provided in Example I herein.

Antibody functional fragments which bind sLe$^a$ can be generated by any technique well known to those of skill in the art. For example, Fab and F(ab')$_2$ fragments of the invention can be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain.

The antibody functional fragments of the invention can also be generated using various phage display methods known in the art. For example, in phage display methods, functional antibody domains, such as the heavy and/or light chain variable regions having one, two, three, four, five or six CDRs provided herein, are displayed on the surface of phage particles which carry the polynucleotide sequences encoding them. The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen, such as sLe$^a$, can be selected or identified with antigen, e.g., using labeled antigen or antigen bound or captured to a solid surface or bead. Examples of phage display methods that can be used to make the antibody functional fragments of the present invention include those disclosed in Brinkman et al., 1995, *J. Immunol. Methods* 182:41-50; Ames et al., 1995, *J. Immunol. Methods* 184:177-186; Kettleborough et al., 1994, *Eur. J. Immunol.* 24:952-958; Persic et al., 1997, *Gene* 187:9-18; Burton et al., 1994, *Advances in Immunology* 57:191-280; PCT Application No. PCT/GB91/01134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described herein.

Techniques to recombinantly produce Fab, Fab' and F(ab')$_2$ fragments can also be employed using methods known in the art such as those disclosed in PCT publication No. WO 92/22324; Mullinax et al., 1992, *BioTechniques* 12(6):864-869; Sawai et al., 1995, *AJRI* 34:26-34; and Better et al., 1988, *Science* 240:1041-1043, each of which is incorporated by reference in its entirety.

To generate whole antibodies, PCR primers including VH or VL nucleotide sequences, a restriction site, and a flanking sequence to protect the restriction site can be used to amplify the VH or VL sequences in scFv clones. Utilizing cloning techniques well known to those of skill in the art, the PCR amplified VH domains can be cloned into vectors expressing a VH constant region, e.g., the human gamma 1 constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques well known to those of skill in the art.

In some embodiments, an antibody or functional fragment of the invention is conjugated (covalent or non-covalent conjugations) or recombinantly fused to one or more diagnostic agent, detectable agent or therapeutic agent or any other desired molecule. The conjugated or recombinantly fused antibody or functional fragment can be useful for monitoring or diagnosing the onset, development, progression and/or severity of a disease associated with the expression of sLe$^a$, such as cancer or tumor formation, as part of a clinical testing procedure, such as determining the efficacy of a particular therapy.

Detection and diagnosis can be accomplished, for example, by coupling the antibody or functional fragment of the invention to detectable substances including, but not limited to, radioactive materials, such as, but not limited to, zirconium ($^{89}$Zr), iodine ($^{131}$I, $^{125}$I, $^{124}$I, $^{121}$I, and $^{121}$I,), carbon ($^{14}$C, $^{11}$C), sulfur ($^{35}$S), tritium ($^{3}$H), indium ($^{115}$In, $^{113}$In, $^{112}$In, and $^{111}$In,), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{15}$O, $^{13}$N, $^{64}$Cu, $^{94m}$Tc, $^{153}$Sm, $^{177}$Lu, $^{159}$Gd, $^{149}$Pm, $^{140}$La, $^{175}$Yb, $^{166}$Ho, $^{86}$Y, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin, and non-radioactive paramagnetic metal ions.

The present invention further encompasses therapeutic uses of an antibody or functional fragment of the invention conjugated (covalent or non-covalent conjugations) or recombinantly fused to one or more therapeutic agent. In this context, for example, the antibody may be conjugated or recombinantly fused to a therapeutic agent, such as a cytotoxin, e.g., a cytostatic or cytocidal agent, or a radioactive metal ion, e.g., alpha-emitters. A cytotoxin or cytotoxic agent includes any agent that is detrimental to cells. A therapeutic agent can be a chemotherapeutic such as, but is not limited to, an anthracycline (e.g., doxorubicin and daunorubicin (formerly daunomycin)); a taxan (e.g., paclitaxel (Taxol) and docetaxel (Taxotere); an antimetabolite (e.g., methotrexate, 6-mercaptopurine, 6-thioguanine, cytarabine, 5-fluorouracil and decarbazine); or an alkylating agent (e.g., mechlorethamine, thioepa chlorambucil, melphalan, carmustine (BCNU), lomustine (CCNU), cyclothosphamide, busulfan, dibromomannitol, streptozotocin, mitomycin C, cisdichlorodiamine platinum (II) (DDP) and cisplatin); an antibiotic (e.g., actinomycin D, bleomycin, mithramycin, and anthramycin (AMC)); an Auristatin molecule (e.g., auristatin PHE, bryostatin 1, solastatin 10, monomethyl auristatin E (MMAE) and monomethylauristatin F (MMAF)); a hormone (e.g., glucocorticoids, progestins, androgens, and estrogens); a nucleoside analoge (e.g. Gemcitabine), a DNA-repair enzyme inhibitor (e.g., etoposide and topotecan), a kinase inhibitor (e.g., compound ST1571, also known as Gleevec or imatinib mesylate); a cytotoxic agent (e.g., maytansine, paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, 1-dehydrotestosterone, glucorticoids, procaine, tetracaine, lidocaine, propranolol, puromycin and analogs or homologs thereof, and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); a farnesyl transferase inhibitor (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); a topoisomerase inhibitor (e.g., camptothecin, irinotecan, SN-38, topotecan, 9-aminocamptothecin, GG-211 (GI 147211), DX-8951f, IST-622, rubitecan, pyrazoloacridine, XR-5000, saintopin, UCE6, UCE1022, TAN-1518A, TAN 1518B, KT6006, KT6528, ED-110, NB-506, ED-110, NB-506, fagaronine, coralyne, beta-lapachone and rebeccamycin); a DNA minor groove binder (e.g., Hoescht dye 33342 and Hoechst dye 33258); adenosine deaminase inhibitors (e.g., Fludarabine phosphate and 2-Chlorodeoxyadenosine); or pharmaceutically acceptable salts, solvates, clathrates, or prodrugs thereof. A therapeutic agent can be a immunotherapeutic such as, but is not limited to, cetuximab, bevacizumab, heceptin, rituximab).

In addition, an antibody or functional fragment of the invention can be conjugated to a therapeutic agent such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm; or a macrocyclic chelator, such as 1,4,7,10-tetraazacyclododecane-N,N',N'',N'''-tetraacetic acid (DOTA) which can be attached to the antibody or functional fragment via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50.

Further, an antibody or functional fragment of the invention may be conjugated (covalent or non-covalent conjugations) or recombinantly fused to a therapeutic agent that modifies a given biological response. Thus, therapeutic agents are not to be construed as limited to classical chemical therapeutic agents. For example, the therapeutic agent can be a protein, peptide, or polypeptide possessing a desired biological activity. Such proteins can include, for example, a toxin (e.g., abrin, ricin A, pseudomonas exotoxin, cholera toxin and diphtheria toxin); a protein such as tumor necrosis factor, γ-interferon, α-interferon, nerve growth factor, platelet derived growth factor, tissue plasminogen activator, an apoptotic agent (e.g., TNF-γ, AIM I, AIM II, Fas Ligand and VEGF), an anti-angiogenic agent (e.g., angiostatin, endostatin and a component of the coagulation pathway such as tissue factor); a biological response modifier (e.g., a cytokine such as interferon gamma, interleukin-1, interleukin-2, interleukin-5, interleukin-6, interleukin-7, interleukin-9, interleukin-10, interleukin-12, interleukin-15, interleukin-23, granulocyte macrophage colony stimulating factor, and granulocyte colony stimulating factor); a growth factor (e.g., growth hormone), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

The present invention encompasses antibodies or functional fragments of the invention recombinantly fused or chemically conjugated (covalent or non-covalent conjugations) to a heterologous protein or polypeptide to generate fusion proteins. In some aspects, such a polypeptide can be about 10, about 20, about 30, about 40, about 50, about 60, about 70, about 80, about 90 or about 100 amino acids in length. In some aspects, the invention provides fusion proteins having a functional fragment of an antibody of the invention (e.g., a Fab fragment, Fd fragment, Fv fragment, F(ab)$_2$ fragment, a VH domain, a VH CDR, a VL domain or a VL CDR) and a heterologous protein or polypeptide. In one embodiment, the heterologous protein or polypeptide that the antibody or functional fragment is fused to is useful for targeting the antibody or functional fragment to a particular cell type, such as a cell that expresses sLe$^a$.

A conjugated or fusion protein of the invention includes any antibody or functional fragment of the invention provided herein conjugated (covalent or non-covalent conjugations) or recombinantly fused to a diagnostic agent, detectable agent or therapeutic agent. In one embodiment, a conjugated or fusion protein of the invention includes a 5B1, 9H3, 5H11 or 7E3 antibody, and a diagnostic agent, detectable agent or therapeutic agent. In another embodiment, a conjugated or fusion protein of the invention includes a functional fragment of 5B1, 9H3, 5H11 or 7E3 antibodies, and a diagnostic agent, detectable agent or therapeutic agent. In another embodiment, a conjugated or fusion protein of the invention includes a VH domain having the amino acid sequence of any one of the VH domains depicted in residues 20-142 of SEQ ID NO: 2, residues 20-142 of SEQ ID NO: 6, residues 20-142 of SEQ ID NO: 10, or residues 20-145 of SEQ ID NO: 14, and/or a VL domain having the amino acid sequence of any one of the VL domains depicted in residues 20-130 of SEQ ID NO: 4, residues 20-129 of SEQ ID NO: 8, residues 20-130 of SEQ ID NO: 12, or residues 23-130 of SEQ ID NO: 16, and a diagnostic agent, detectable agent or therapeutic agent. In another embodiment, a conjugated or fusion protein of the present invention includes one or more VH CDRs having the amino acid sequence of any one of the VH CDRs depicted in SEQ ID NOS: 2, 6, 10 or 14, and a diagnostic agent, detectable agent or therapeutic agent. In another embodiment, a conjugated or fusion protein includes one or more VL CDRs having the amino acid sequence of any one of the VL CDRs depicted in SEQ ID NOS: 4, 8, 12 or 16, and a diagnostic agent, detectable agent or therapeutic agent. In another embodiment, a conjugated or fusion protein of the invention includes at least one VH domain and at least one VL domain depicted in residues 20-142 of SEQ ID NO: 2 and residues 20-130 of SEQ ID NO: 4; residues 20-142 of SEQ ID NO: 6 and residues 20-129 of SEQ ID NO: 8; residues 20-142 of SEQ ID NO: 10 and residues 20-130 of SEQ ID NO: 12; or residues 20-145 of SEQ ID NO: 14 and residues 23-130 of SEQ ID NO: 16, respectively, and a diagnostic agent, detectable agent or therapeutic agent.

Methods for fusing or conjugating diagnostic agents, detectable agents or therapeutic agents (including polypeptides) to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, 5,112,946, 7,981,695, 8,039,273, 8,142,784; U.S. Publications 2009/0202536, 2010/0034837, 2011/0137017, 2011/0280891, 2012/0003247; EP 307,434; EP 367,166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992; and Senter, Current Opinion in Chemical Biology, 13:235-244 (2009), which are incorporated herein by reference in their entireties.

In another aspect, a diagnostic agent, detectable agent or therapeutic agent can be attached at the hinge region of a reduced antibody component via disulfide bond formation. Alternatively, such agents can be attached to the antibody component using a heterobifunctional cross-linker, such as N-succinyl 3-(2-pyridyldithio)proprionate (SPDP). Yu et al., Int. J. Cancer 56: 244 (1994). General techniques for such conjugation are well known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995).

Alternatively, a diagnostic agent, detectable agent or therapeutic agent can be conjugated via a carbohydrate moiety in the Fc region of the antibody. Methods for conjugating peptides to antibody components via an antibody carbohydrate moiety are well known to those of skill in the art. See, for example, Shih et al., *Int. J. Cancer.* 41:832-839 (1988); Shih et al., *Int. J. Cancer.* 46:1101-1106 (1990); and Shih et al., U.S. Pat. No. 5,057,313, all of which are incorporated in their entirety by reference. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

However, if the Fc region is absent, for example, if an antibody functional fragment as provided herein is desirable, it is still possible to attach a diagnostic agent, a detectable agent or a therapeutic agent. A carbohydrate moiety can be introduced into the light chain variable region of a full-length antibody or antibody fragment. See, for example, Leung et al., *J. Immunol.*, 154: 5919 (1995); U.S. Pat. Nos. 5,443,953 and 6,254,868, all of which are incorporated in their entirety by reference. The engineered carbohydrate moiety is used to attach the diagnostic agent, detectable agent or therapeutic agent.

The therapeutic agent conjugated or recombinantly fused to an antibody functional fragment of the invention that binds to $sLe^a$ can be chosen to achieve the desired prophylactic or therapeutic effect(s). It is understood that it is within the skill level of a clinician or other medical personnel to consider the following when deciding which therapeutic agent to conjugate or recombinantly fuse to an antibody or functional fragment of the invention: the nature of the disease, the severity of the disease, and the condition of the subject.

A conjugate or fusion antibody or functional fragment of the invention that is detectably labeled as provided herein and binds to $sLe^a$ can be used for diagnostic purposes to detect, diagnose, or monitor a disease, wherein the cells that cause or are associated with the disease express $sLe^a$. For example, as provided herein, cancer cells and tumors have been shown to express $sLe^a$, such as, but not limited to, tumors of the gastrointestinal tract, breast cancer, ovarian cancer, colon cancer, colorectal adenocarcinoma, pancreatic cancer, pancreatic adenocarcinoma, small cell carcinoma of the lung, bladder adenocarcinoma, metastatic colon cancer, colorectal cancer, signet ring ovarian cancer and metastatic carcinoma. Accordingly, the invention provides methods for detecting cancer or a tumor formation in a subject by administering an effective amount of a conjugate or fusion antibody or functional fragment of the invention to a subject in need thereof. In some aspects, the detection method can further include assaying the expression of a $sLe^a$ on the cells or a tissue sample of a subject using one or more conjugates or fusion antibodies or functional fragments of the invention that bind to $sLe^a$; and comparing the level of the $sLe^a$ with a control level, e.g., levels in normal tissue samples (e.g., from a subject not having a disease, or from the same subject before disease onset), whereby an increase in the assayed level of $sLe^a$ compared to the control level of the $sLe^a$ is indicative of the disease. Such diagnostic methods can allow health professionals to employ preventative measures or aggressive treatment earlier than otherwise possible thereby preventing the development or further progression of the disease.

An antibody or functional fragment of the invention can also be used to assay $sLe^a$ antigen levels in a biological sample using classical immunohistological methods as provided herein or as well known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting $sLe^a$ include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In) and technetium ($^{99}$Tc); luminescent labels, such as luminol; and fluorescent labels, such as fluorescein and rhodamine, and biotin.

In one aspect, the invention provides for the detection and diagnosis of disease in a human. In one embodiment, diagnosis includes: a) administering (for example, parenterally, subcutaneously, or intraperitoneally) to a subject an effective amount of a conjugate or fusion protein of the invention that binds to $sLe^a$; b) waiting for a time interval following the administering for permitting the conjugate or fusion protein to preferentially concentrate at sites in the subject where $sLe^a$ is expressed (and, in some aspects, for unbound conjugate or fusion protein to be cleared to background level); c) determining background level; and d) detecting the conjugate or fusion protein in the subject, such that detection of conjugate or fusion protein above the background level indicates that the subject has a disease. Background level can be determined by various methods including, comparing the amount of conjugate or fusion protein detected to a standard value previously determined for a particular system.

It is understood that the size of the subject and the imaging system used will determine the quantity of imaging moiety needed to produce diagnostic images and can be readily determined by one of skill in the art. For example, in the case of a radioisotope conjugated to an antibody or functional fragment of the invention, for a human subject, the quantity of radioactivity injected will normally range from about 5 to 20 millicuries of $^{99}$Tc. The conjugate will then preferentially accumulate at the location of cells which express $sLe^a$. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of detectable agent used and the mode of administration, the time interval following the administration for permitting the conjugate to preferentially concentrate at sites in the subject and for unbound conjugate to be cleared to background level is 6 to 48 hours or 6 to 24 hours or 6 to 12 hours. In another embodiment, the time interval following administration is 5 to 20 days or 5 to 10 days. In one embodiment, monitoring of a disease is carried out by repeating the method for diagnosing as provided herein, for example, one month after initial diagnosis, six months after initial diagnosis, one year after initial diagnosis, or longer.

The presence of the conjugate or fusion protein can be detected in the subject using methods known in the art for in vivo scanning. These methods depend upon the type of detectable agent used. A skilled artisan will be able to determine the appropriate method for detecting a particular detectable agent. Methods and devices that may be used in the diagnostic methods of the invention include, but are not limited to, computed tomography (CT), whole body scan such as position emission tomography (PET), magnetic resonance imaging (MRI), and sonography. In one embodiment, an antibody or function fragment of the invention is conjugated to a radioisotope and is detected in the subject using a radiation responsive surgical instrument. In another embodiment, an antibody or function fragment of the invention is conjugated to a fluorescent compound and is detected in the subject using a fluorescence responsive scanning instrument. In another embodiment, an antibody or function fragment of the invention is conjugated to a positron emitting metal, such as zirconium ($^{89}Zr$) or any other positron emitting metal provided herein or that is well known in the art to be detectable by positron emission-tomography, and is detected in the subject using positron emission-tomography. In yet another embodiment, an antibody or function fragment of the invention is conjugated to a paramagnetic label and is detected in a subject using magnetic resonance imaging (MRI).

In one embodiment, the invention provides a pharmaceutical composition having an antibody or a functional fragment of the invention and a pharmaceutically acceptable carrier. A pharmaceutically acceptable carrier that can be used in the pharmaceutical compositions of the invention include any of the standard pharmaceutical carriers known in the art, such as phosphate buffered saline solution, water and emulsions such as an oil and water emulsion, and various types of wetting agents. These pharmaceutical compositions can be prepared in liquid unit dose forms or any other dosing form that is sufficient for delivery of the antibody or functional fragment of the invention to the target area of the subject in need of treatment. For example, the pharmaceutical compositions can be prepared in any manner appropriate for the chosen mode of administration, e.g., intravascular, intramuscular, subcutaneous, intraperitoneal, etc. Other optional components, e.g., pharmaceutical grade stabilizers, buffers, preservatives, excipients and the like can be readily selected by one of skill in the art. The preparation of a pharmaceutically composition, having due regard to pH, isotonicity, stability and the like, is within the level of skill in the art.

Pharmaceutical formulations containing one or more antibodies or functional fragments of the invention provided herein can be prepared for storage by mixing the antibody having the desired degree of purity with optional physiologically acceptable carriers, excipients or stabilizers (*Remington's Pharmaceutical Sciences* (1990) Mack Publishing Co., Easton, Pa.), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Thus, in some embodiments, the invention provides a method for treating or preventing a disease in a subject in need thereof. The methods of the invention can include administering a therapeutically effective amount of a pharmaceutical composition provided herein to the subject. For example, the pharmaceutical composition can include one or more antibody or functional fragment provided herein. Diseases that can be treated or prevented using the methods of the invention include cancer, tumor formation and/or metastasis. In particular, the methods of the invention are useful for treating cancers or tumor formation wherein the cancer cells or tumor expresses the carbohydrate sLe$^a$. Non-limiting examples of cancers or tumors that can be treated or prevented using the methods of the invention include tumors of the gastrointestinal tract, for example, colon cancer, colorectal adenocarcinoma, metastatic colon cancer, colorectal cancer, pancreatic cancer, or pancreatic adenocarcinoma; small cell carcinoma of the lung; bladder adenocarcinoma; signet ring ovarian cancer; ovarian cancer, metastatic carcinoma; and adenocarcinoma of the stomach, esophagus, throat, urogenital tract, or breast.

Accordingly, in some aspects, the invention provides a method for treating cancer or preventing tumor metastasis in a subject in need thereof by administering a therapeutically effective amount of a pharmaceutical composition having an antibody or functional fragment thereof, wherein the antibody or functional fragment binds to sLe$^a$ and includes a VH domain having an amino acid sequence selected from the group consisting of residues 20-142 of SEQ ID NO: 2, residues 20-142 of SEQ ID NO: 6, residues 20-142 of SEQ ID NO: 10, and residues 20-145 of SEQ ID NO: 14. In another aspect, the invention provides a method for treating cancer or preventing tumor metastasis in a subject in need thereof by administering a therapeutically effective amount of a pharmaceutical composition having an antibody or functional fragment thereof, wherein the antibody or functional fragment binds to sLe$^a$ and includes a VL domain having an amino acid sequence selected from the group consisting of residues 20-130 of SEQ ID NO: 4, residues 20-129 of SEQ ID NO: 8, residues 20-130 of SEQ ID NO: 12, and residues 23-130 of SEQ ID NO: 16. In yet another aspect, the invention provides a method for treating cancer or preventing tumor metastasis in a subject in need thereof by administering a therapeutically effective amount of a pharmaceutical composition having an antibody or functional fragment thereof, wherein the antibody or functional fragment binds to sLe$^a$ and includes both a VH domain and a VL domain, where the VH domain and the VL domain respectively include an amino acid sequence selected from the group consisting of residues 20-142 of SEQ ID NO: 2 and residues 20-130 of SEQ ID NO: 4; residues 20-142 of SEQ ID NO: 6 and residues 20-129 of SEQ ID NO: 8; residues 20-142 of SEQ ID NO: 10 and residues 20-130 of SEQ ID NO: 12; and residues 20-145 of SEQ ID NO: 14 and residues 23-130 of SEQ ID NO: 16.

Formulations, such as those described herein, can also contain more than one active compound as necessary for the particular disease being treated. In certain embodiments, formulations include an antibody or functional fragment of the invention and one or more active compounds with complementary activities that do not adversely affect each other. Such molecules are suitably present in combination in amounts that are effective for the purpose intended. For example, an antibody or functional fragment of the invention can be combined with one or more other therapeutic agents. Such combined therapy can be administered to the subject concurrently or successively.

Thus, in some aspects, invention provides a method for treating or preventing a disease by administering a therapeutically effective amount of a pharmaceutical composition provided herein to a subject in need thereof, wherein the pharmaceutical composition includes an antibody or functional fragment of the invention and a second therapeutic agent. The appropriate second therapeutic agent can be readily determined by one of ordinary skill in the art as discussed herein. As provided herein in Example IV, in some aspects of the invention, the second therapeutic agent can be Taxol.

The pharmaceutical compositions provided herein contain therapeutically effective amounts of one or more of the antibodies of the invention provided herein, and optionally one or more additional therapeutic agents, in a pharmaceutically acceptable carrier. Such pharmaceutical compositions are useful in the prevention, treatment, management or amelioration of a disease, such cancer or tumor formation, or one or more of the symptoms thereof.

The pharmaceutical compositions can contain one or more antibodies or functional fragments of the invention. In one embodiment, the antibodies or functional fragments are formulated into suitable pharmaceutical preparations, such as sterile solutions or suspensions for parenteral administration. In one embodiment, the antibodies or functional fragments provided herein are formulated into pharmaceutical compositions using techniques and procedures well known in the art (see, e.g., Ansel (1985) Introduction to Pharmaceutical Dosage Forms, $4^{th}$ Ed., p. 126).

An antibody or functional fragment of the invention can be included in the pharmaceutical composition in a therapeutically effective amount sufficient to exert a therapeutically useful effect in the absence of undesirable side effects on the subject treated. The therapeutically effective concentration can be determined empirically by testing the compounds in in vitro and in vivo systems using routine methods and then extrapolated therefrom for dosages for humans. The concentration of an antibody or functional fragment in the pharmaceutical composition will depend on, e.g., the physicochemical characteristics of the antibody or functional fragment, the dosage schedule, and amount administered as well as other factors well known to those of skill in the art.

In one embodiment, a therapeutically effective dosage produces a serum concentration of an antibody or functional fragment of from about 0.1 ng/ml to about 50-100 µg/ml. The pharmaceutical compositions, in another embodiment, provide a dosage of from about 0.001 mg to about 500 mg of antibody per kilogram of body weight per day. Pharmaceutical dosage unit forms can be prepared to provide from about 0.01 mg, 0.1 mg or 1 mg to about 30 mg, 100 mg or 500 mg, and in one embodiment from about 10 mg to about 500 mg of the antibody or functional fragment and/or a combination of other optional essential ingredients per dosage unit form.

The antibody or functional fragment of the invention can be administered at once, or may be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of the antibody or functional fragment of the invention, the resulting mixture can be a solution, suspension or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as sterile parenteral solutions or suspensions containing suitable quantities of the compounds or pharmaceutically acceptable derivatives thereof. The antibody or functional fragment can be, in one embodiment, formulated and administered in unit-dosage forms or multiple-dosage forms. Unit-dose forms refers to physically discrete units suitable for human and animal subjects and packaged individually as is known in the art. Each unit-dose contains a predetermined quantity of the antibody or functional fragment of the invention sufficient to produce the desired therapeutic effect, in association with the required pharmaceutical carrier, vehicle or diluent. Examples of unit-dose forms include ampoules and syringes. Unit-dose forms can be administered in fractions or multiples thereof. A multiple-dose form is a plurality of identical unit-dosage forms packaged in a single container to be administered in segregated unit-dose form. Examples of multiple-dose forms include vials or bottles of pints or gallons. Hence, multiple dose form is a multiple of unit-doses which are not segregated in packaging.

In one embodiment, one or more antibody or functional fragment of the invention is in a liquid pharmaceutical formulation. Liquid pharmaceutically administrable compositions can, for example, be prepared by dissolving, dispersing, or otherwise mixing an antibody or functional fragment as provided herein and optional pharmaceutical adjuvants in a carrier, such as, for example, water, saline, aqueous dextrose, glycerol, glycols, ethanol, and the like, to thereby form a solution. If desired, the pharmaceutical composition to be administered can also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see *Remington's Pharmaceutical Sciences* (1990) Mack Publishing Co., Easton, Pa.

Methods for administering a pharmaceutical composition of the invention are well known in the art. It is understood that the appropriate route of administration of a pharmaceutical composition can be readily determined by a skilled clinician. Exemplary routes of administration include intravenous injection, intramuscular injection, intradermal injection or subcutaneous injection. Moreover, it is understood that the formulation of the pharmaceutical composition can be readily adjusted to accommodate the route of administration. The invention also provides that following administration of a pharmaceutical composition of the invention, delayed, successive and/or repeated dosages of one or more pharmaceutical composition as provided herein may be administered to the subject.

The methods of the invention for treating a disease is intended to include (1) preventing the disease, i.e., causing the clinical symptoms of the disease not to develop in a subject that may be predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms. The methods of the invention for preventing a disease is intended to include forestalling of a clinical symptom indicative of cancer or tumor formation. Such forestalling includes, for example, the maintenance of normal physiological indicators in a subject. Therefore, preventing can include the prophylactic treatment of a subject to guard them from the occurrence of tumor metastasis.

The therapeutically effective amount of the pharmaceutical composition used in the methods of the invention will vary depending on the pharmaceutical composition used, the disease and its severity and the age, weight, etc., of the subject to be treated, all of which is within the skill of the attending clinician. A subject that that can be treated by the methods of the invention include a vertebrate, preferably a mammal, more preferably a human.

It is understood that modifications which do not substantially affect the activity of the various embodiments of this invention are also provided within the definition of the invention provided herein. Accordingly, the following examples are intended to illustrate but not limit the present invention.

Example I

Human Monoclonal Antibodies to sLe$^a$ have Potent Antitumor Activity

The carbohydrate antigen sLe$^a$ is widely expressed on epithelial tumors of the gastrointestinal tract, breast, and pancreas and on small-cell lung cancers. Since over-expression of sLe$^a$ appears to be a key event in invasion and metastasis of many tumors and results in susceptibility to antibody-mediated lysis, sLe$^a$ is an attractive molecular target for tumor therapy. Accordingly, as described herein, fully human monoclonal antibodies (mAb) from blood lymphocytes from individuals immunized with a sLe$^a$-KLH vaccine were generated and characterized. Several mAbs were selected based on ELISA and FACS including two mAbs with high affinity for sLe$^a$ (5B1 and 7E3, binding affinities 0.14 and 0.04 nmol/L, respectively) and further characterized. Both antibodies were specific for Neu5Ac$\alpha$2-3Gal$\beta$1-3(Fuc$\alpha$1-4)GlcNAc$\beta$ and Neu5Gc$\alpha$2-3Gal$\beta$1-3(Fuc$\alpha$1-4)GlcNAc$\beta$ as determined by glycan array analysis. Complement-dependent cytotoxicity against DMS-79 cells was higher (EC50 0.1 μg/mL vs. 1.7 μg/mL) for r7E3 (IgM) than for r5B1 (IgG1). In addition, r5B1 antibodies showed high level of antibody-dependent cell-mediated cytotoxicity activity on DMS-79 cells with human NK cells or peripheral blood mononuclear cells. To evaluate in vivo efficacy, the antibodies were tested in a xenograft model with Colo205 tumor cells or DMS-79 tumor cells engrafted into severe combined immunodeficient (SCID) mice. In the Colo205 xenograft model, treatment during the first 21 days with four doses of r5B1 (100 μg per dose) doubled the median survival time to 207 days, and three of five animals survived with six doses. In the DSM-79 xenograft model, growth of established DMS-79 tumors was suppressed or regressed in animals treated with r5B1 antibody. On the basis of the potential of sLe$^a$ as a target for immune attack and their affinity, specificity, and effector functions, 5B1 and 7E3 have clinical utility in the treatment of cancer.

Materials, Cells, and Antibodies

DMS-79 (Pettengill et al., *Cancer*, 45:906-18 (1980)), SW626, EL4, HT29, BxPC3, SK-MEL28, and P3×63Ag8.653 cell lines were purchased from American Type Culture Collection (ATCC). Colo205-luc cells (Bioware ultra) were obtained from Caliper Life Sciences. The murine control mAb 121SLE (IgM) was purchased from GeneTex. sLe$^a$ tetrasaccharide (Cat # S2279) was purchased from Sigma-Aldrich. sLe$^a$-HSA (human serum albumin) conjugate (Cat #07-011), monovalent biotinylated sLe$^a$ (sLe$^a$-sp-biotin; Cat #02-044), polyvalent biotinylated sLe$^a$-PAA (Cat #01-044), biotin-labeled Le$^a$-PAA (Cat #01-035), and sLe$^a$-PAA-biotin (Cat #01-045) were purchased from GlycoTech. In the polyvalent presentation, the tetrasaccharide is incorporated into a polyacrylamide matrix (PAA), thereby creating a 30-kDa multivalent polymer with approximately every fifth amide group of the polymer chain N-substituted with biotin in a 4:1 ratio and approximately 20% carbohydrate content. Other HSA or BSA glycoconjugates used in this study were prepared in-house using sLe$^a$ pentenyl glycoside as described. Ragupathi et al., *Cancer Immunol Immunother*, 58:1397-405 (2009). GD3, fucosyl-GM1, GM2, and GM3 were purchased from Matreya, and GD2 was purchased from Advanced ImmunoChemical.

Generation of Anti-sLe$^a$ mAb-Producing Hybridomas

Blood samples were obtained from 3 patients in an ongoing trial with sLe$^a$-KLH conjugate vaccine in patients with breast cancer initiated at MSKCC under an MSKCC- and FDA-approved IRB protocol and IND. Blood specimens were selected from 2 patients after 3 or 4 vaccinations, which showed antibody titers of 1/160 and 1/320, respectively, against sLe$^a$. These sera (and murine mAb 19.9) react well with sLe$^a$-positive cell lines in FACS assays and mediate potent CDC. Ragupathi et al., *Cancer Immunol Immunother*, 58:1397-405 (2009). Peripheral blood mononuclear cells (PBMC) were isolated from approximately 80 to 90 mL of blood by gradient centrifugation on Histopaque-1077 (Sigma-Aldrich).

PBMCs were cultured in RPMI-1640 medium supplemented with L-glutamine, nonessential amino acids, sodium pyruvate, vitamin, penicillin/streptomycin, 10% FBS (Omega Scientific), 10 ng/mL IL-21 (Biosource), and 1 μg/mL anti-CD40 mAb (G28-5 hybridoma supernatant; ATCC). Cells were fused by electrofusion to P3×63Ag8.653 myeloma cells.

sLe$^a$ ELISA

For the sLe$^a$ ELISA, plates were coated either with 1 µg/mL of sLe$^a$-HSA conjugate, monovalent biotinylated sLe$^a$, or with polyvalent biotinylated sLe$^a$-PAA captured on Neutr-Avidin-coated plates. Uncoated wells (PBS) and HSA-coated wells were used as controls. Bound antibodies were initially detected with horseradish peroxidase (HRP)-labeled goat anti-human IgA+G+M (Jackson ImmunoResearch), and positive wells were subsequently probed with IgG-Fc- or IgM-specific secondary antibodies to determine isotypes.

Carbohydrate Specificity Analysis

Cross-reactivity against the closely related antigens, Le$^a$ and sLe$^x$, was evaluated by surface plasmon resonance (SPR) and confirmed by ELISA using biotin-labeled Le$^a$-PAA and biotin-sLe$^x$-PAA. Binding to gangliosides GD2, GD3, fucosyl-GM1, GM2, and GM3 was tested by ELISA. A competition ELISA was used to evaluate the specificity of the mAbs against several other related carbohydrate moieties. In brief, 2 µg/mL sLe$^a$-HSA conjugate was coated onto plates followed by blocking with 3% BSA in PBS. Next, 30 µL of different carbohydrate moieties (40 µg/mL in PBS prepared from 1 mg/mL stock solutions) either unconjugated or conjugated to HSA or BSA was mixed separately with 30 µL of test antibody and incubated at room temperature in a sample plate. After 30 minutes 50 µL of the mixture was transferred to the coated assay plate and incubated for 1 hour, followed by incubation with HRP-labeled goat anti-human IgA+G+M, washing and colorimetric detection of bound antibody using a Versamax spectrofluorometer (all steps were carried out at room temperature). The tested carbohydrate moieties included globo H, Lewis Y, Lewis X, sialyl-Thomson-nouveaux (sTn), clustered sTn, Thomson Friedenreich (TF), Tighe Le$^b$/Le$^Y$ mucin, porcine submaxillary mucin (PSM), and sLe$^a$ tetrasaccharide and sLe$^a$-HSA conjugate. To determine the fine specificity of the antibodies, glycan array analysis was done by the Consortium for Functional Glycomics Core H group. 5B1 and 7E3 antibodies were tested at 10 µg/mL using version 4.1 of the printed array consisting of 465 glycans in replicates of 6.

Immunoglobulin cDNA Cloning and Recombinant Antibody Expression

Variable region of human mAb heavy and light chain cDNA was recovered by RT-PCR from the individual hybridoma cell line and subcloned into IgG1 or IgM heavy chain or IgK or IgL light chain expression vector as described before. Sawada-Hirai et al., *J. Immune Based Ther. Vaccines*, 2:5 (2004). Ig heavy chain or light chain expression vector was double-digested with Not I and Sal I, and then both fragments were ligated to form a dual-gene expression vector. CHO cells in 6-well plates were transfected with the dual-gene expression vector using Lipofectamine 2000 (Invitrogen). After 24 hours, transfected cells were transferred to a 10-cm dish with selection medium [DMEM supplemented with 10% dialyzed FBS (Invitrogen), 50 mmol/L L-methionine sulfoximine (MSX), GS supplement (Sigma-Aldrich), and penicillin/streptomycin (Omega Scientific)]. Two weeks later MSX-resistant transfectants were isolated and expanded. High anti-sLe$^a$ antibody-producing clones were selected by measuring the antibody levels in supernatants in a sLe$^a$-specific ELISA assay and expanded for large-scale mAb production.

Human mAb Purification

Antibodies were purified using the Äkta Explorer (GE Healthcare) system running Unicorn 5.0 software. In brief, stable clones of 5B1 or 7E3 were grown in serum-free culture medium in a Wave bioreactor, and the harvested supernatant was clarified by centrifugation and filtration and stored refrigerated until used. Human IgG antibodies were purified on appropriate-sized protein A columns using 10 mmol/L PBS and 150 mmol/L NaCl running buffer. Human IgM antibodies were purified on a hydroxyapatite column, and IgM was eluted with a gradient of 500 mmol/L phosphate. The antibody concentrations were determined by $OD_{280}$ using an $E^{1\%}$ of 1.4 and 1.18 for IgG and IgM, respectively, to calculate the concentration. The purity of each preparation was evaluated by SDS-PAGE analysis (1-5 µg per lane) under reducing conditions, and the purity was more than 90% based on the sum of heavy and light chains.

Flow Cytometry sLe$^a$-positive or -negative tumor cell lines ($0.5 \times 10^6$ cells per condition) were washed in PBS/2% FBS (PBSF). Test or control human mAb was then added (1-2 µg/mL in complete medium) and incubated on ice for 30 minutes. Gilewski et al., *Clin Cancer Res*, 6:1693-701 (2000); Gilewski et al. *Proc. Natl. Acad. Sci. U.S.A.*, 98:3270-5 (2001). After washing in PBSF, the cells were incubated with Alexa-488 anti-human IgG-Fcγ or anti-human IgM-µ (Invitrogen) for 30 minutes on ice. Cells were washed twice in PBSF and analyzed by flow cytometry using the Guava Personal Cell Analysis-96 (PCA-96) System (Millipore). Colo205-luc cells were incubated with 2 µg/mL of primary antibody, followed by staining with secondary antibodies from SouthernBiotech, and analyzed on a Becton Dickinson FACS Advantage IV instrument using FlowJo 7.2.4 software.

Affinity Determination

Affinity constants were determined using the principle of SPR with a Biacore 3000 (GE Healthcare). Biotin-labeled univalent sLe$^a$ (Cat #02-044) or polyvalent sLe$^a$-PAA-biotin (Cat #01-044) were coupled to separate flow cells of an SPA biosensor chip according to the manufacturer's instructions. A flow cell blocked with HSA and culture medium containing free biotin was used as a reference cell. The binding kinetic parameters were determined from several known concentrations of antibody diluted in HBS-EP buffer (10 mmol/L HEPES, pH 7.4, 150 mmol/L NaCl, 3.4 mmol/L EDTA, 0.005% surfactant P20) using the sLe$^a$-PAA-biotin-coated flow cell. The curve-fitting software provided by the Biacore instrument was used to generate estimates of the association and dissociation rates from which affinities are calculated.

CDC Assay sLe$^a$ antigen-positive and -negative cell lines were used for a 90-minute cytotoxicity assay (Guava PCA-96 Cell-Toxicity kit; Millipore; Cat #4500-0200) using human complement (Quidel; Cat #A113) and purified human mAbs at various dilutions (0.1-25 µg/mL) or with positive control mAbs as previously described (Ragupathi et al. *Clin Cancer Res* 2003, 9:5214; Ragupathi et al. *Int J Cancer* 2000, 85:659; Dickler et al. *Cancer Res* 1999, 5:2773). In brief, $2.5 \times 10^6$ target cells were painted with carboxyfluorescein diacetate succinymyl ester (CSFE) to yield green/yellow fluorescent target cells. The painted cells ($1 \times 10^5/50$ µL sample) were incubated for 40 minutes with 100 µL of antibodies on ice. Next, 50 µL of human complement diluted 1:2 in complete medium (RPMI-1640, 10% FCS) or medium alone was added to triplicate samples and incubated for 90 minutes at 37° C. Thus, the final complement dilution in the assay was 1:8. Cells that were killed during this incubation time were labeled by adding the membrane impermeable dye 7-amino-actinomycin D (7-AAD), and samples were analyzed by dual-color immunofluorescence utilizing the Guava CellToxicity software module. Control samples that received NP40 were used to determine maximal killing and samples receiving complement alone served as baseline. The percentage of killed cells was determined by appropriate gating and calculated according to the following formula: % killed=[(% sample−% complement alone)/(% NP40−complement alone)]×100.

Antibody-Dependent Cell-Mediated Cytotoxicity Assay

Figure 13:
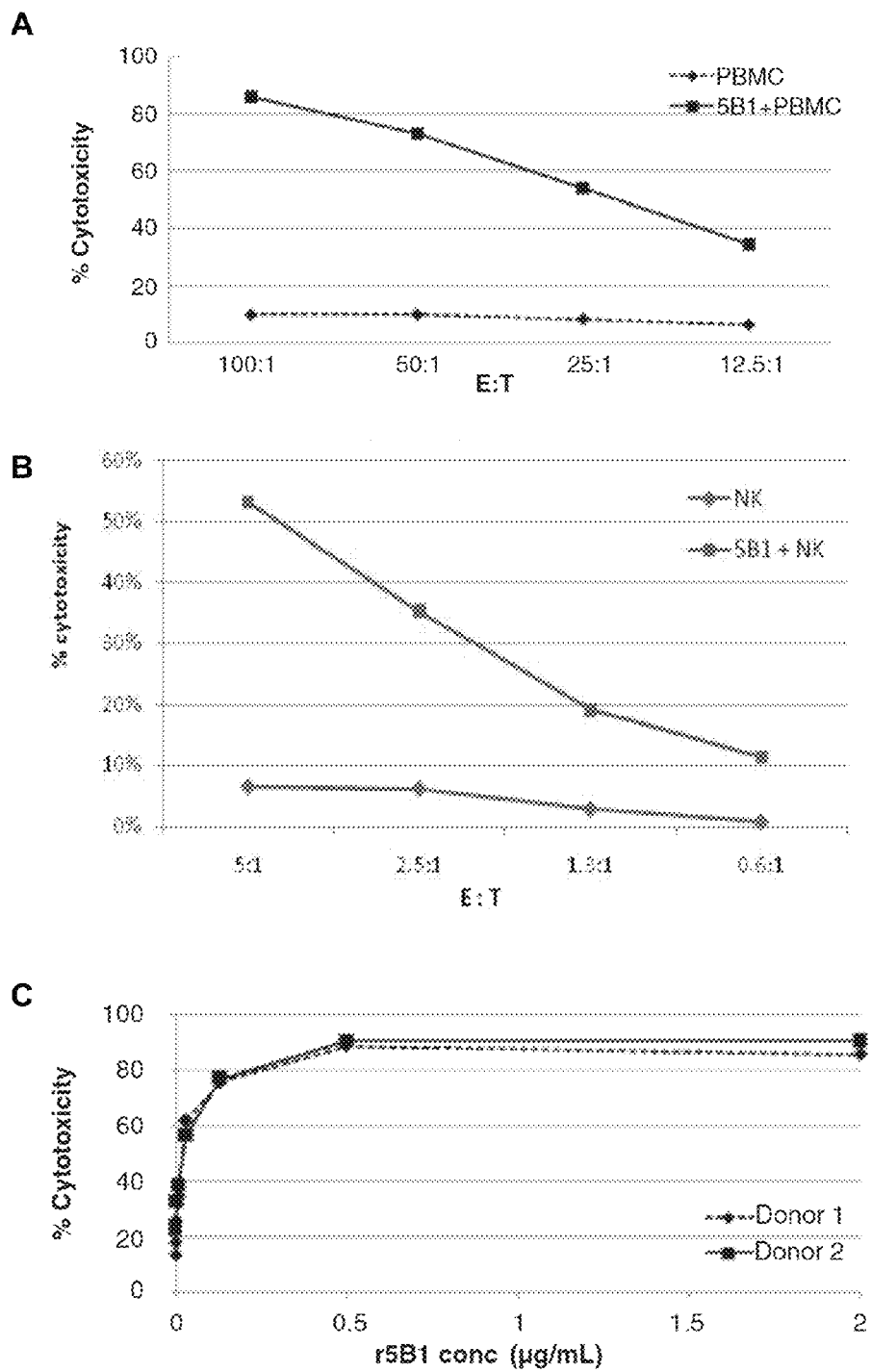
FIG. 13, panels A-C, show antibody-dependent cell-mediated cytotoxicity (ADCC) of r5B1 antibodies. Panel A shows r5B1-mediated ADCC with human PBMC against DMS-79 cells. PBMC were tested at E:T ratios from 100:1 to 12.5:1 with DMS-79 tumor cells in the presence or absence of 2 μg/mL r5B1. Panel B shows r5B1-mediated ADCC with primary human NK cells against DMS-79 cells. NK cells were tested at lower E:T ratios from 5:1 to 0.6:1 with DMS-79 tumor cells in the presence or absence of 2 μg/mL r5B1. Panel C shows ADCC of r5B1 at various concentrations with PBMCs from 2 donors at an E:T ratio of 1:100 with DMS-79 tumor cells in the presence of the indicated concentrations of r5B1.

PBMC effector cells were isolated by Ficoll-Hypaque density centrifugation from blood samples obtained under an MSKCC IRB-approved protocol. The target cells were incubated at $5 \times 10^6$ cells/mL in complete growth media with 15 µL of 0.1% calcein-AM solution (Sigma-Aldrich) for 30 minutes at 37° C., in the presence of 5% $CO_2$. The cells were washed twice with 15 mL of PBS-0.02% EDTA and resuspended in 1 mL complete growth medium. Fifty microliters (10,000 cells) of labeled target cells was plated into a 96-well plate in the presence or absence of antibodies at the concentrations described in FIG. 13, and incubated with 50 µL of freshly isolated peripheral blood mononuclear cells (effector cells, at 100:1 E/T ratio) accordingly. After 2 hours of incubation, the plate was centrifuged at 300×g for 10 minutes, and 75 µL of supernatant was transferred into a new flat-bottomed 96-well plate. The fluorescence in the supernatant was measured at 485-nm excitation and 535-nm emission in Fluoroskan Ascent (Thermo Scientific). Spontaneous release was determined from target cells in RPMI-1640 medium with 30% FBS without effector cells and maximum release was determined from target cells in RPMI-1640 medium with 30% FBS and 6% Triton X-100 without effector cells. Percent cytotoxicity was calculated as [(counts in sample−spontaneous release)/(maximum counts−spontaneous release)]×100.

mAb Internalization Assay

Internalization of 5B1 antibody was evaluated by measuring the cytotoxic activity of r5B1 and Hum-ZAP secondary conjugate (Advanced Targeting Systems) complex against $sLe^a$ expressing BxPC3 cells, which were plated into a 96-well plate (2,000 cells/90 µL/well) and incubated overnight in duplicates. Various concentrations of 5B1 antibody were incubated with Hum-ZAP secondary conjugates at RT according to the manufacturer's instruction. Next, 10 µL/well of r5B1 and Hum-ZAP complex was added to the cells and incubated for 3 days. Twenty-five microliters of Thiazolyl Blue Tetrazolium Bromide (Sigma-Aldrich) solution (5 mg/mL in PBS) was added to each well and incubated at 37° C. After 2 hours of incubation, 100 µL/well of solubilization solution (20% SDS/50% N,N-dimethylformamide) was added to each well and incubated for another 16 hours at 37° C. The OD was measured at 570/690 nm, and values obtained with medium alone were used for plate background subtraction. Eight parallel cultures without antibody were used to normalize the sample values (sample/mean untreated×100).

Xenograft Transplantation Model

Female CB17 SCID mice (5-8 weeks old) were purchased from Taconic. For the Colo205 xenograft model, Colo205-luc cells ($0.5 \times 10^6$) in 0.1 mL complete growth media were injected via the tail vein on day 0 using a BD insulin syringe with 28G needle (Becton Dickinson & Co). For the first study, one hundred micrograms of mAb 5B1 was injected intraperitoneally on days 1, 7, 14, and 21 (experiment 1) or on days 1, 4, 7, 10, 14, and 21 (experiment 2). For the second study, 100 µg, 300 µg or 1 mg of mAb 5B1 was injected intraperitoneally on Day 4 after tumor cell injection, then twice a week for the first two weeks and once a week for the next 7 weeks. Mice were monitored for tumor development. For the DMS-79 xenograft model, DMS-79 cells ($1 \times 10^6$) were injected subcutaneously into Female CB17 SCID mice, and the mice began treatment on Day 19 after the tumor length reached 5 mm (~20 mm$^2$). The animals were then treated with human IgG or 5B1 antibodies given by intraperitoneal injection at 200 µg per dose, plus cRGD by intravenous injection to increase vascular permeability initially at 80 µg, then 5 days per week, 40 µg per dose until day 37.

All procedures were done under a protocol approved by the Memorial Sloan Kettering Cancer Center Institutional Animal Care and Use Committee. Kaplan-Meier survival curves were generated using GraphPad Prism 5.1 (GraphPad Software) and analyzed using the Mantel-Haenszel log-rank test.

Results

Identification of Human Monoclonal Antibodies by ELISA and Generation of Recombinant Antibodies Blood samples from 3 vaccinated patients were used for hybridoma generation efforts and many positive wells were detected in the antigen-specific ELISA assays (Table 3). Extensive screening was used to eliminate antibodies that showed inferior or nonspecific binding. Eight human antibody-expressing hybridoma cells (1 IgM and 7 IgG) with strong reactivity against $sLe^a$ were initially selected, expanded, and subcloned for further characterization. Two antibodies (9H1 and 9H3) showed strong binding to $sLe^a$-HSA conjugates but not to $sLe^a$-PAA-coated plates. Three antibodies (5B1, 5H11, and 7E3) showed strong binding to monovalent and polyvalent $sLe^a$ and $sLe^a$-HSA conjugates when measured by ELISA assays (Table 4).

TABLE 3

Binding of candidate hybridoma supernatants containing IgG or IgM monoclonal antibodies to $sLe^a$-acetylphenylenediamine(APD)-human serum albumin(HSA) conjugate ($sLe^a$-HuSA).

| | | OD (490 nm)* | | |
| --- | --- | --- | --- | --- |
| Supernatant | Isotype | HuSA | $sLe^a$-HuSA | PBS |
| EF41-5B1 | G | 0.000 | 2.240 | 0.020 |
| EF41-5H11 | G | 0.020 | 2.180 | −0.010 |
| EF41-6F7 | G | 0.010 | 0.480 | −0.010 |
| EF41-9H1 | G | 0.010 | 0.730 | −0.020 |
| EF41-9H3 | G | 0.010 | 1.100 | −0.020 |
| EF41-9A10 | G | 0.010 | 2.140 | −0.010 |
| EF41-10C1 | G | 0.000 | 0.040 | −0.020 |
| EF40-3C4 | G | 0.000 | 0.500 | 0.000 |
| EF40-10H3 | G | 0.000 | 0.130 | 0.000 |
| EF41-7E3 | M | −0.020 | 2.130 | 0.010 |
| EF41-9A7 | M | 2.700 | 2.540 | 2.610 |
| EF40-5B7 | M | 0.070 | 0.070 | 0.080 |

*isotype control blank subtracted.
HuSA indicates human serum albumin control.
PBS indicates phosphate buffered saline control.

TABLE 4

Binding of the select antibodies to $sLe^a$ presented as univalent (mono-) $sLe^a$, multivalent (poly-) $sLe^a$, or $sLe^a$-HSA form.

| | OD (490 nm) | | | | |
| --- | --- | --- | --- | --- | --- |
| Supernatant | PBS | NAV | NAV + mono-$sLe^a$ | NAV + poly-$sLe^a$ | SLeA-HSA* |
| EF41-5B1(G) | 0.050 | 0.050 | 0.900 | 2.280 | 1.740 |
| EF41-5H11(G) | 0.040 | 0.050 | 1.280 | 2.130 | 1.900 |
| EF41-6F7(G) | 0.050 | 0.050 | 0.050 | 0.080 | 0.100 |
| EF41-9H1(G) | 0.050 | 0.050 | 0.050 | 0.060 | 0.300 |
| EF41-9H3 (G) | 0.050 | 0.050 | 0.050 | 0.050 | 0.750 |
| EF41-9A10 (G) | 0.040 | 0.040 | 0.170 | 0.870 | 1.330 |
| EF40-3C4 (G) | 0.040 | 0.050 | 0.040 | 0.050 | 0.070 |
| EF41-7E3 (M) | 0.050 | 0.050 | 0.970 | 0.920 | 1.310 |

HuSA indicates human serum albumin control.
PBS indicates phosphate buffered saline control.
NAV indicates Neutral Avidin control.

The heavy and light chain variable regions from 4 selected antibodies were recovered by RT-PCR and cloned into our full-length IgG1 or IgM expression vectors. Molecular sequence analysis using IMGT/V-Quest (Brochet et al., *Nucleic Acids Res.*, 36:W503-8 (2008)) revealed that the 3 selected IgG antibodies 5B1 (IgG/λ), 9H3 (IgG/λ), and 5H11 (IgG/λ) were derived from the same VH family and all used lambda light chains. These IgG1 antibodies showed different CDR sequences with 16, 5, or 3 mutations deviating from the germ line, respectively (FIGS. 1-6; Table 5). The IgM antibody (7E3) utilizes the kappa light chain and has 6 heavy chain mutations (FIGS. 7-8; Table 5). The increased mutations in 5B1 are indicative of affinity maturation. Recombinant antibodies were produced in CHO cell lines in a wave bioreactor system and purified using protein A or hydroxyapatite chromatography for IgG and IgM, respectively. The purified recombinant antibodies retained the properties of the original hybridoma-derived antibodies with respect to ELISA binding and specificity.

TABLE 5 cDNA Classification of selected human anti-sLe$^a$ antibodies derived from vaccinated blood donors.

| Antibo. Clone ID | VH | Muta. from germline | DH (RF) | JH | CDR length | VL | Muta. from germline | JL | CDR length |
|---|---|---|---|---|---|---|---|---|---|
| 5B1 | 3-9*01 | 16 | 6-25*01 (1) | 4*02 | 8, 8, 16 | L1-47*01 | 4 | JL1*01 | 8, 3, 12 |
| 9H3 | 3-9*01 | 5 | 2-8*01 (2) | 4*02 | 8, 8, 16 | L1-47*01 | 2 | JL2*01 | 8, 3, 11 |
| 5H11 | 3-9*01 | 3 | 6-25*01(1) | 4*02 | 8, 8, 16 | L1-47*01 | 1 | JL1*01 | 8, 3, 12 |
| 7E3 | 3-30*03 | 6 | 2-15*01 (2) | 4*02 | 8, 8, 19 | K3-15*01 | 3 | JK2*01 | 6, 3, 10 |

Analysis of Tumor Cell Binding

Figures 11A, 11B, 11C:
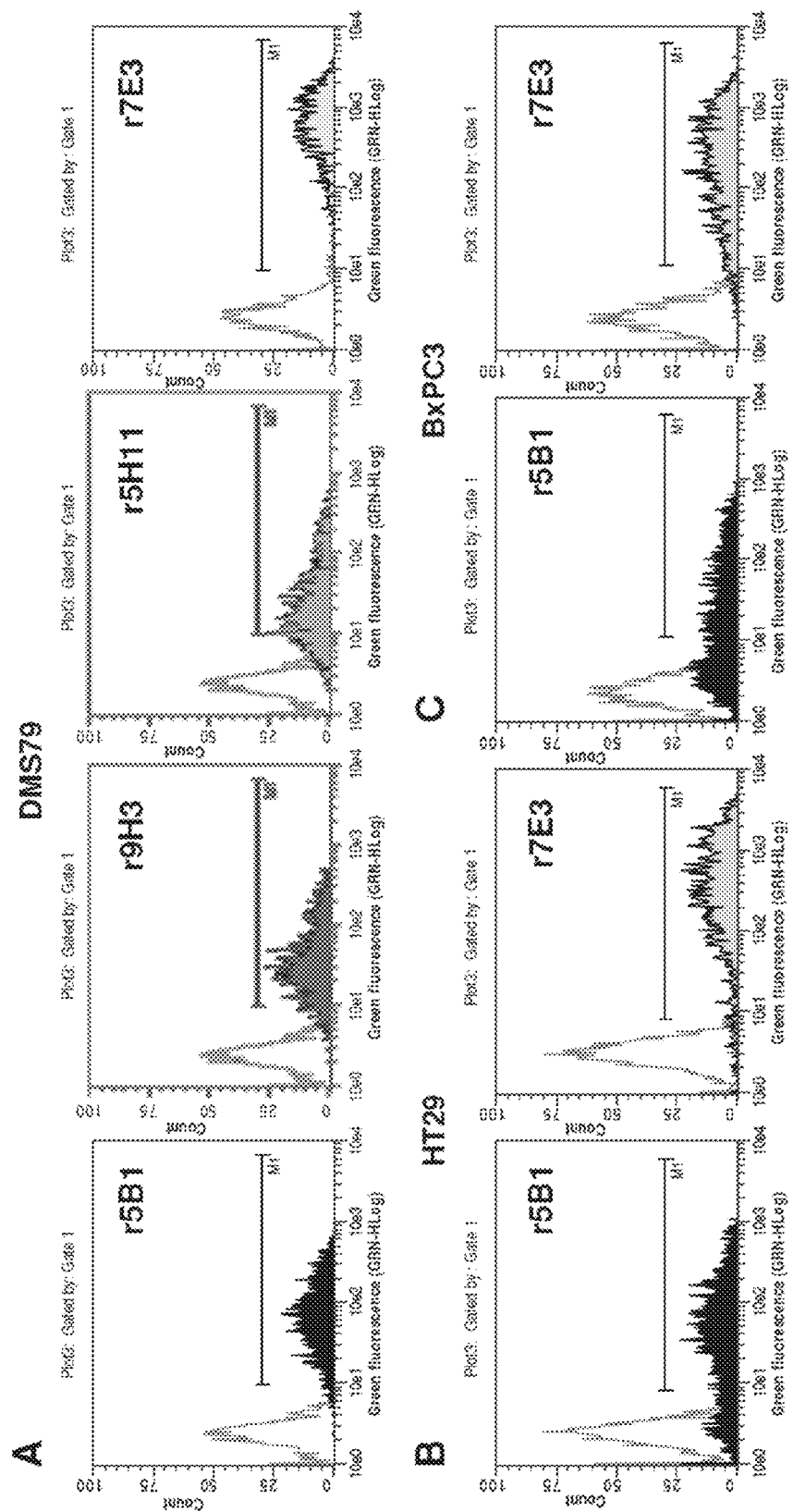
Figures 11D, 11E, 11F:
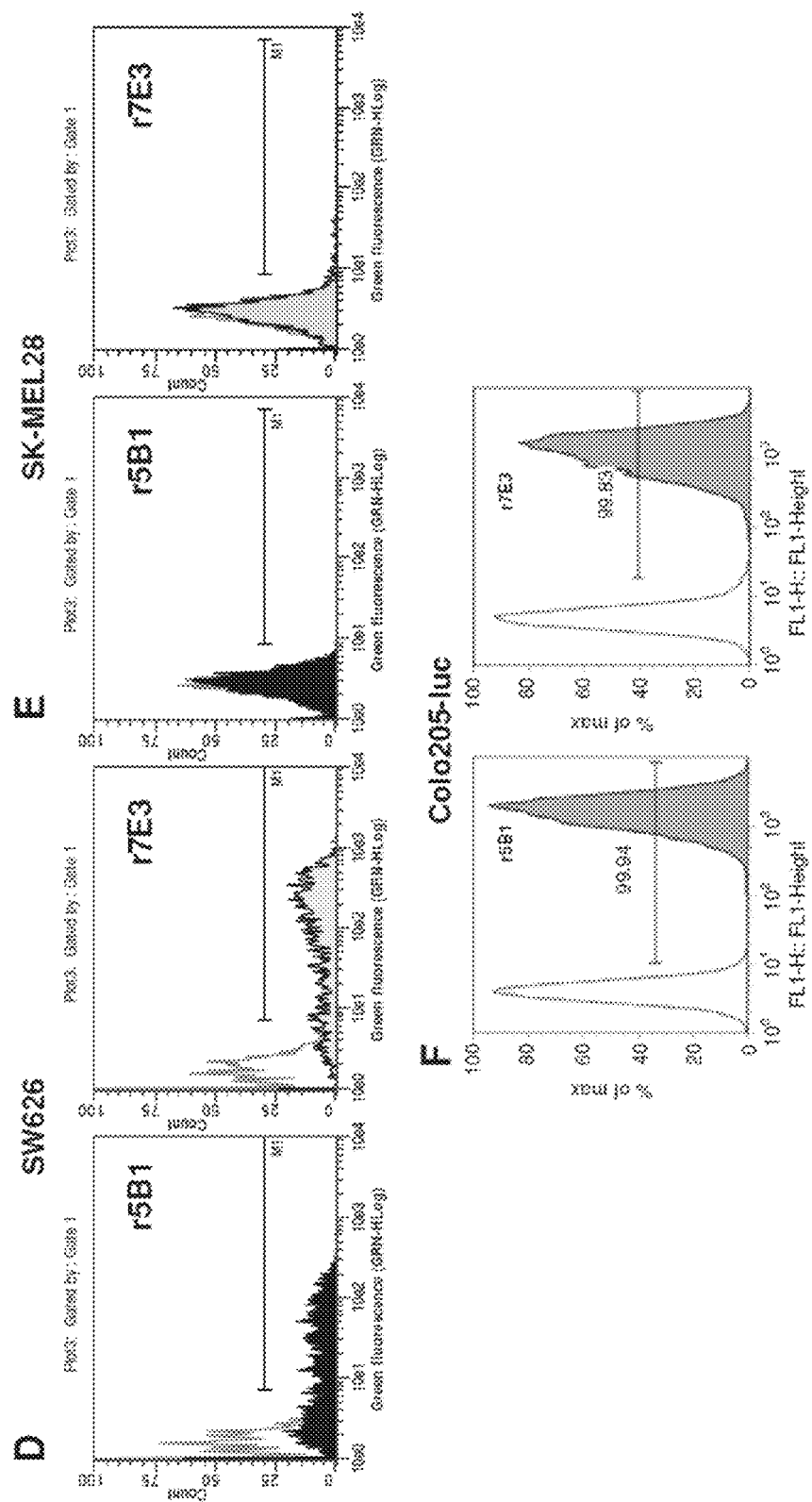

Cell surface binding is crucial for cytotoxic activity and was therefore tested next. Flow cytometry showed strong binding of 5B1, 9H3, 5H11, and 7E3 recombinant antibodies to DMS-79 cells, a small-cell lung cancer suspension cell line (FIG. 11A). Binding of r5B1 and r7E3 was also confirmed on HT29 colon cancer cells (FIG. 11B), BxPC3 pancreatic cancer cells (FIG. 11C), SW626 ovarian cancer cells (FIG. 11D), and Colo205-luc colon cancer cells (FIG. 11F). These antibodies failed to bind to sLe$^a$-negative (SLE121-negative) SK-MEL28 melanoma cells (FIG. 11E) or EL4 mouse lymphoma cells (data not shown).

Affinity Measurements

The relative affinity/avidity of the binding to sLe$^a$ was probed by SPR using a streptavidin-coated biosensor chip to capture biotinylated sLe$^a$-PPA. As shown in Table 6, r5B1 and r7E3 bind rapidly to sLe$^a$-PPA and show a significantly slower off-rate compared with 121SLE, a commercially available murine IgM anti-sLe$^a$ antibody that was used for comparison. The affinity of 5B1 was measured at 0.14 nmol/L, and the apparent affinity/avidity of 7E3 was approximately 4 times higher (Table 6). Determination of 9H3 affinity was hampered since 9H3 antibodies (native and recombinant) failed to bind to the sLe$^a$-PAA-coated biosensor chip.

TABLE 6

Determination of kinetic parameters of anti-sLe$^a$ antibodies by SPR.

| mAb | Affinity, nmol/L | $K_d$, mol/L | $K_a$, 1/mol/L | Association $k_a$, 1/mol/L s | Dissociation kd, 1/s | Isotype |
|---|---|---|---|---|---|---|
| r5B1 | 0.14 | 1.4 × 10$^{-10}$ | 7.0 × 10$^9$ | 1.1 × 10$^6$ | 1.6 × 10$^{-4}$ | IgG1/λ |
| r7E3 | 0.04 | 3.6 × 10$^{-11}$ | 2.8 × 10$^{10}$ | 8.8 × 10$^5$ | 3.2 × 10$^{-5}$ | IgM/κ |
| 121SLE | 0.35 | 3.5 × 10$^{-10}$ | 2.8 × 10$^9$ | 2.7 × 10$^6$ | 9.4 × 10$^{-4}$ | m-IgM |

Specificity Analysis

Preliminary assays to probe carbohydrate specificity showed that 5B1, 9H3, and 7E3 did not bind to the closely related sLe$^X$, Le$^a$, or Le$^Y$ antigens or the gangliosides GD2, GD3, fucosyl-GM1, GM2, and GM3 as measured by ELISA or SPR. Additional analysis of 7E3, 5B1 and 121SLE binding to sLe$^a$-PAA-biotin or sLe$^a$-sp-biotin captured on a Biacore avidin chip showed that all three antibodies bound to the polyvalent form of sLe$^a$, whereas 7E3 and 5B1 were found to bind the monovalent form. The binding of 5B1 to sLe$^a$-PAA was also inhibited by sLe$^a$ tetrasaccharide in a dose-dependent manner in a Biacore concentration analysis series (data not shown). These results are consistent with previous observations that sera with high anti-sLe$^a$ antibody titers were found to be specific for sLe$^a$, that is, not reactive with gangliosides GM2, GD2, GD3, fucosyl GM1, or the neutral glycolipids globo H and Le$^y$ by ELISA. Ragupathi et al., *Cancer Immunol Immunother* 58:1397-405 (2009). In a competition assay with 9 distinct related carbohydrate moieties in various presentations (e.g., as ceramide, or conjugated to BSA or HSA), only sLe$^a$ tetrasaccharide and sLe$^a$-HSA conjugate were able to inhibit binding to sLe$^a$-HSA conjugate (Table 7).

TABLE 7

Binding to sLeA-PAA-HSA in the presence of various related glycoconjugates.

| Antigens | r5B1 Exp 1 | r5B1 Exp 2 | r9H3 Exp 1 | r9H3 Exp 2 | r7E3 Exp 1 | r7E3 Exp 2 |
|---|---|---|---|---|---|---|
| Sialyl Tn-HSA | 1.866 | 1.981 | 1.882 | 1.970 | 2.218 | 2.259 |
| GloboH-ceramide | 1.866 | 1.852 | 1.906 | 1.821 | 2.098 | 2.201 |
| sTn(c)-HSA (direct) | 1.896 | 1.864 | 1.947 | 1.883 | 2.131 | 2.136 |
| sTn-M2-HSA (mono) | 1.937 | 1.857 | 1.843 | 1.826 | 2.040 | 2.066 |
| LeX-gal-cer | 1.893 | 1.863 | 1.791 | 1.810 | 2.173 | 2.175 |
| dPSM | 1.897 | 1.890 | 1.757 | 1.700 | 2.218 | 2.110 |
| Tn-mono allyl M2-HSA | 1.837 | 1.905 | 2.041 | 1.991 | 2.083 | 2.107 |

TABLE 7-continued

Binding to sLeA-PAA-HSA in the presence of various related glycoconjugates.

| | r5B1 | | r9H3 | | r7E3 | |
|---|---|---|---|---|---|---|
| Antigens | Exp 1 | Exp 2 | Exp 1 | Exp 2 | Exp 1 | Exp 2 |
| Tighe Leb/LeY mucin | 1.808 | 1.837 | 1.951 | 1.964 | 2.106 | 2.065 |
| LeX-PAA | 1.830 | 1.873 | 2.053 | 2.036 | 2.099 | 2.108 |
| LeY-ceramide | 1.824 | 1.821 | 1.940 | 1.980 | 2.143 | 2.085 |
| Lewis Y ceramide | 1.833 | 1.844 | 1.941 | 1.874 | 2.090 | 2.111 |
| Tn(c)-HSA | 1.881 | 1.711 | 1.893 | 1.917 | 2.146 | 2.030 |
| T-serine-BSA | 1.809 | 1.830 | 2.128 | 2.089 | 2.137 | 2.039 |
| TF(c) HSA | 1.874 | 1.909 | 2.031 | 2.032 | 2.119 | 2.094 |
| Tn LY-BSA | 1.901 | 1.863 | 1.944 | 1.959 | 2.084 | 2.118 |
| NPrGBMP-HSA | 1.892 | 1.797 | 1.944 | 1.964 | 2.090 | 2.111 |
| sLeA-HSA | 1.329 | 1.298 | 1.373 | 1.266 | 1.542 | 1.621 |
| sLeA tetrasaccharide | 0.371 | 0.312 | 0.797 | 0.814 | 2.114 | 2.041 |
| None | 1.809 | 1.809 | 1.993 | 1.993 | 2.096 | 2.096 |
| Blank | 0.101 | 0.093 | 0.093 | 0.092 | 0.108 | 0.100 |

To examine the carbohydrate specificity in further detail, 5B1 and 7E3 antibodies were also tested by glycan array analysis done by the Consortium for Functional Glycomics Core H group. Both antibodies were tested at 10 µg/mL on printed arrays consisting of 465 glycans in 6 replicates. The results confirmed the high specificity of both antibodies with selective recognition of the sLe$^a$ tetrasaccharide, Neu5Acα2-3Galβ1-3(Fucα1-4)GlcNAcβ and Neu5Gcα2-3Galβ1-3(Fucα1-4)GlcNAcβ and virtual absence of binding to closely related antigens that were present in the array, including sLe$^x$, Le$^a$, Le$^x$, and Le$^y$. The results are summarized in Table 8, which shows the top 5 of 465 glycan structures that were recognized by the respective antibodies.

TABLE 8

Analysis of carbohydrate specificity by glycan array screening.

| Chart Number | Common Name | Glycan Structure | Average | StDev | % CV |
|---|---|---|---|---|---|
| A. 5B1 | | | | | |
| 237 | sLe$^a$ | Neu5Acα2-3Galβ1-3(Fucα1-4)GlcNAcβ-Sp8 | 851 | 2,797 | 7 |
| 278 | sLe$^a$ | Neu5Gcα2-3Galβ1-3(Fucα1-4)GlcNAcβ-Sp0 | 32,714 | 2,624 | 8 |
| 329 | sLe$^a$Le$^a$ | Neu5Acα2-3Galβ1-3(Fucα1-4)GlcNAcβ1-3Galβ1-3(Fucα1-4)GlcNAcβ-Sp0 | 6,477 | 399 | 9 |
| 238 | sLe$^a$Le$^x$ | Neu5Acα2-3Galβ1-3(Fucα1-4)GlcNAcβ1-3Galβ1-4(Fucα1-3)GlcNAcβ-Sp0 | 1,344 | 131 | 10 |
| 349 | | Galβ1-4GlcNAcβ1-2Manα1-3(Manα1-6)Manβ1-4GlcNAcβ1-4GlcNAcβ-Sp12 | 129 | 62 | 48 |
| B. 7E3 | | | | | |
| 237 | sLe$^a$ | Neu5Acα2-3Galβ1-3(Fucα1-4)GlcNAcβ-Sp8 | 40,920 | 4,676 | 11 |
| 329 | sLe$^a$Le$^a$ | Neu5Acα2-3Galβ1-3(Fucα1-4)GlcNAcβ1-3Galβ1-3(Fucα1-4)GlcNAcβ-Sp0 | 40,210 | 2,095 | 5 |
| 238 | sLe$^a$Le$^x$ | Neu5Acα2-3Galβ1-3(Fucα1-4)GlcNAcβ1-3Galβ1-4(Fucα1-3)GlcNAcβ-Sp0 | 39,848 | 3,621 | 9 |
| 278 | sLe$^a$ | Neu5Gcα2-3Galβ1-3(Fucα1-4)GlcNAcβ-Sp0 | 36,707 | 2,733 | 7 |
| 349 | | Galβ1-4GlcNAcβ1-2Manα1-3(Manα1-6)Manβ1-4GlcNAcβ1-4GlcNAcβ-Sp12 | 692 | 52 | 8 |

CDC Activity

Figure 12:
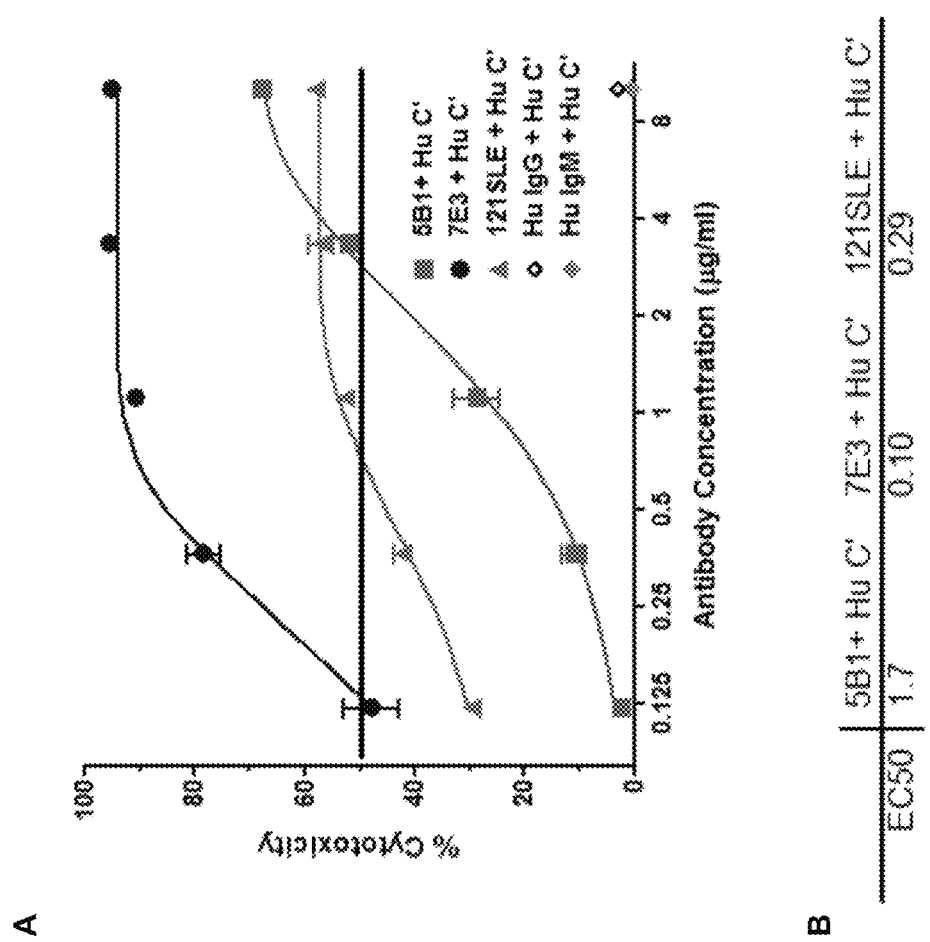
FIG. 12, panels A and B, show CDC activity of r5B1 and r7E3 antibodies in comparison to murine 121SLE (IgM) in the presence of human complement (Hu C') as measured against DMS-79 cells. Human isotype control antibodies, Hu IgG (◇) and Hu IgM (◆) showed <4% cytotoxicity. A dose response for r5B1 IgG (■), r7E3 IgM (●) and 121SLE mIgM (▲) antibodies is shown in panel A. The calculated EC50 (μg/ml) for r5B1 (IgG), r7E3 (IgM) and 121SLE (mIgM) antibodies is shown in panel B.

To evaluate the functional activity of 5B1 and 7E3, we tested the cytotoxic activity with DMS-79 cells in the presence of human serum as a source of complement. Both antibodies showed in some assays close to 100% killing activity at 10 µg/mL, while a control antibody with different specificity (1B7, anti-GD2 IgG1 mAb) had no effect at the same concentrations (data not shown). The CDC activity is concentration dependent, and 7E3 was significantly more active than 5B1 in this assay (FIG. 12), which is expected since IgM antibodies are known to be more effective in complement-mediated cytotoxicity assays. The EC$_{50}$ (50% cytotoxicity) was 1.7 µg/mL for 5B1 and 0.1 µg/mL for 7E3, which translates to roughly 85-fold higher potency for 7E3 on a molar basis (FIG. 12).

ADCC Activity

While 7E3 is significantly more potent in the CDC assay, IgG antibodies are known to have antibody-dependent cell-mediated cytotoxicity (ADCC) activity, which is thought to be important for tumor killing in vivo. High levels of cytotoxicity were measured using 5B1 antibody with human PBMC and DMS-79 target cells at various E:T ratios (FIG. 13A). Similar levels of cytotoxicity were observed at lower E:T ratios with primary NK cells (FIG. 13B). A dose-response experiment with PBMC from 2 donors measured at an E/T ratio of 100:1 showed similar efficacy, and more than 85% cytotoxicity was reached at concentrations of 0.5 µg/mL or more of 5B1 (FIG. 13C). The cytotoxicity mediated by 5B1 requires FcγRIII receptors since it can be blocked with 3G8 anti-CD16 antibodies. High levels of cytotoxicity were also measured using 5B1 antibody with human PBMC against Colo205-luc cells at an E:T ratio of 100:1. The ADCC activity achieved with 1 µg/mL of 5B1 antibodies was superior to the activity observed with antibodies to GM2, fucosyl-GM1, globo H, or polysialic acid. As expected, 7E3 and murine 121SLE (both are IgM) were inactive in this assay.

5B1 Internalization Assay

Figure 14:
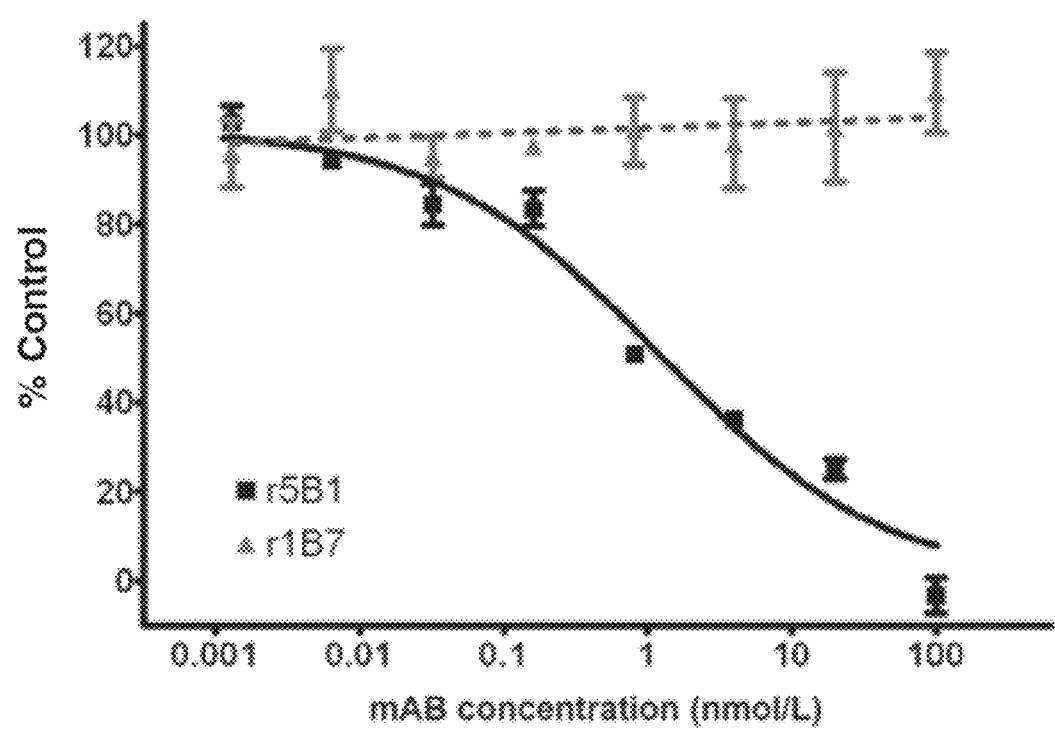
FIG. 14 shows internalization of sLe$^a$ into BxPC3 cells. BxPC3 pancreatic tumor cells were grown in the presence of r5B1 (anti-sLe$^a$) or r1B7 (anti-GD2) antibodies complexed with Hum-ZAP, a saporin-conjugated anti-human IgG. After 3 days, the viability of the cells was measured using an 3-(4,5-Dimethylthiazol-2-yl)-2,5-diphenyltetrazolium bromide (MTT) assay and the sample values were normalized to the values of untreated cultures.

Antibody conjugates directed at antigen "closely related to" Lewis Y were previously shown to be rapidly internalized and very effective in animal models. Hellstrom et al., Cancer Res 50:2183-90 (1990); Trail et al., Science 261:212-5 (1993). To examine whether sLe$^a$ is internalized, we incubated the pancreatic cell line, BxPC3 with 5B1, and then added Hum-ZAP, an anti-human IgG conjugated to the ribosome-inactivation protein saporin. Kohls et al., Biotechniques 28:162-5 (2000). Cells that internalize the saporin-containing complex die, while noninternalized saporin leaves the cells unharmed. As shown in FIG. 14, BxPC3 cells are effectively killed in the presence of increasing doses of 5B1 while the presence of an isotype-matched IgG1 antibody directed against GD2, which is not expressed on these cells, does not kill the cells.

Activity in Xenograft Animal Model for Metastasis

Figure 15:
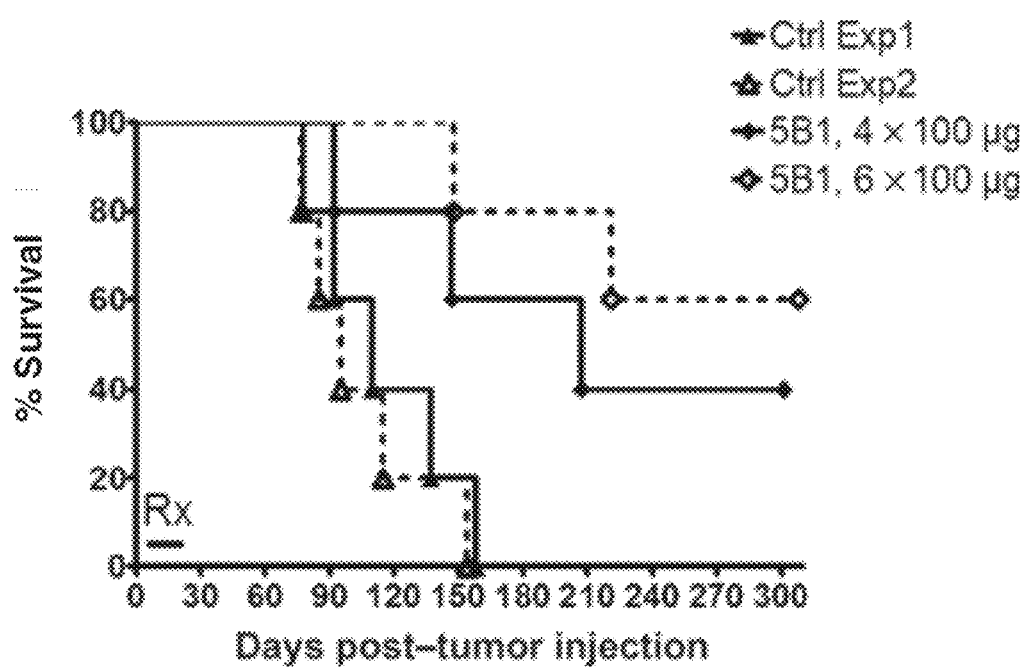
FIG. 15 shows activity of r5B1 antibody in a xenograft model using Colo205-luc cells. Severe combined immuno-deficient (SCID) mice (5 per group) received 0.5 million Colo205-luc cells by tail vein injection on day 0. Mice received 100 μg r5B1 by intraperitoneal injection on days 1, 7, 14, and 21 (experiment 1, Exp1) or on days 1, 4, 7, 10, 14, and 21 (experiment 2, Exp2) for a total dose of 600 μg. Control (Ctrl) animals received PBS mock injections.

To evaluate the activity of 5B1 in vivo, the antibodies were tested in two xenograft models using either Colo205-luc tumor cells or DMS-79 tumor cells in SCID mice. For the xenograft model using Colo205-luc tumor cells, five mice per group were injected with $0.5 \times 10^6$ cells into the tail vein on day 0, and successful injection of the cells was verified by imaging the animals using the IVIS 200 in vivo imaging system (Caliper Life Sciences). One day later, animals were treated with 5B1 antibodies given intraperitoneal or PBS mock injection. In experiment 1, 100 μg of 5B1 was given on days 1, 7, 14, and 21 (400 μg total dose), and in experiment 2 the animals received 100 μg 5B1 on days 1, 4, 7, 10, 14, and 21 (600 μg total dose). The average median survival of untreated animals was 102 days in the 2 experiments, and all untreated animals died within 155 days (FIG. 15). Treatment of animals improved survival significantly: the median survival was doubled to 207 days in the group that received 4 doses of 5B1 and 2 of 5 animals survived until termination of the experiment after 301 days (log-rank test, P=0.0499; HR=3.46). The proportion of survivors further increased to 3 of 5 mice when 6 doses were administered (log-rank test, P=0.0064; HR=6.375). The second experiment was terminated after 308 days, and the surviving animals failed to reveal Colo205-luc tumors at the highest sensitivity of the imaging system (data not shown).

In a second study, mice similarly injected with Colo205-luc tumor cells as described above, were treated with increasing doses of 5B1 or 7E3 antibodies (100 μg, 300 μg or 1 mg). All animals initially received interperitoneal or PBS mock injection (control) of the 5B1 or 7E3 antibody on Day 4 after tumor cell injection, then twice a week for the first two weeks and once a week for the next 7 weeks. The delayed treatment with various doses of 5B1 showed a dose dependent protection up to complete cure in SCID mice engrafted with Colo205-luc tumor cells (FIGS. 16 and 17). Treatment with 7E3 antibodies did not show higher protection despite increased apparent affinity (data not shown).

In a xenograft model using DMS-79 cells, five mice per group were injected subcutaneously with $1 \times 10^6$ cells on day 0, and began treatment on day 19 after the tumor length reached 5 mm (~20 mm$^2$). The animals were then treated with human IgG or 5B1 antibodies given by intraperitoneal injection at 200 μg per dose, plus cRGD by intravenous injection initially at 80 μg, then 5 days per week, 40 μg per dose until day 37. The growth of established DMS-79 tumors was suppressed or regressed in animals treated with 5B1 or a combination of 5B1 plus cRGD (FIGS. 18A and 18B). Treatment of animals with 5B1 on the day of engraftment with DMS-79 cells in a subcutaneous model completely prevented tumor growth (data not shown).

The above data demonstrates a significant ability to suppress or regress established tumors and provide a survival benefit using 5B1 antibody treatment.

Example II

Immuno-PET Detection and Diagnosis of Pancreatic Cancer and Other sLe$^a$ Positive Adenocarcinomas Using Radiolabeled Monoclonal Antibody 5B1

Adenocarcinomas are a leading cause of death from cancer. Detection of pancreatic cancer remains especially difficult with diagnosis often made at a late stage. Approaches for earlier detection of primary and metastatic pancreatic cancers could have significant clinical impact. In clinical practice, elevated levels of sLe$^a$ antigen are monitored to identify suspected occult malignancy in patients with pancreatic cancer. As described herein, the potential of a novel immunoPET imaging probe targeting sLe$^a$ in preclinical models of pancreatic cancer and other sLe$^a$ positive adenocarcinomas was investigated. The human anti-sLe$^a$ monoclonal antibody 5B1 showed positive staining on human adenocarcinomas known to be sLe$^a$ positive but not on sLe$^a$ negative malignancies or most normal tissues. $^{89}$Zr-radiolabeled 5B1 ($^{89}$Zr-5B1) displayed high labeling (>80%) and purification yields (>95%). Imaging with $^{89}$Zr-5B1 was investigated in subcutaneous, orthotopic and metastatic pancreatic cancer xenografts in female SCID mice. Acquired PET images and biodistribution studies demonstrated exceptional specificity and localization of $^{89}$Zr-5B1 for the sLe$^a$ overexpressing BxPC3 xenografts with minimal non-specific binding to healthy tissues. Further analysis in colon and small cell lung cancer subcutaneous xenograft models resulted in excellent tumor delineation by $^{89}$Zr-5B1 as well. Accordingly, these results show that $^{89}$Zr-5B1 can be used as a molecular probe for early detection of sLe$^a$ expressing malignancies in the clinic.

Cell Lines and Tissue Culture

All tissue culture manipulations were performed following sterile techniques. The small cell lung cancer DMS79 and BxPC3 pancreas cancer cells were obtained from the American Type Culture Collection (ATCC, Manassas, Va.). Colo205-luc colorectal cancer cells (Bioware Ultra) were purchased from Caliper Life Sciences (CLS, Hopkinton, Mass.). All cells were grown according to the recommendations of ATCC and CLS under 37° C. with 5% $CO_2$ humidified atmosphere.

In Vitro Evaluation of sLe$^a$ Expression Levels Through FACS

Flow cytometry with the indicated cultured cancer cell lines was performed as described herein in Example I. In brief, single cell suspensions of $1 \times 10^6$ culture tumor cells per tube were washed in PBS with 3% fetal bovine serum (FBS). Human monoclonal antibodies r5B1 (IgG against sLe$^a$) was then added at 20 ug/ml per tube, and incubated on ice for 30 min. After wash in PBS with 3% FBS, 20 μl of 1:25 diluted goat anti-human IgG labeled with fluorescein-isothiocyanate (FITC, Southern Biotechnology, Birmingham, Ala.) was added, and the mixture incubated for another 30 minutes on ice. After a final wash, the positive population and median fluorescence intensity of stained cells were differentiated using FACS Scan (Becton & Dickinson, San Jose, Calif.). Cells stained only with goat antihuman IgG labeled with fluorescein-isothiocyanate were used to set the FACScan result at 1% as background for comparison to percent positive cells stained with primary mAb.

Preparation of $^{89}$Zr-Labeled Antibodies

Recombinant 5B1 antibodies was prepared and purified as described herein. The 5B1 antibodies and a non-specific human IgG were functionalized with p-isothiocyanatobenzyl-desferrioxamine (DFO-Bz-NCS, Macrocyclics, Inc., Dallas, Tex.) with a 1:4 mAb:DFO-Bz-NCS ratio. For example, to 300 μL of 5B1 (1.23 mg in PBS, pH~9), a volume of 7.2 μL DFO-Bz-NCS (4.25 mM in DMSO) was added. The reaction was incubated at 37° C. for 1-1.5 h. The functionalized antibodies were purified via either PD10 desalting column (GE Healthcare) or a 10 kDa centrifugal filter (Amicon).

Zr-89 was produced through proton beam bombardment of yttrium foil and isolated in high purity as Zr-89 oxalate at MSKCC according to previously established procedure. Holland et al., *Nuclear Medicine and Biology* 36:729-39 (2009). Labeling of the antibodies proceeded via methods as described by Holland et al., *Journal of Nuclear Medicine official publication, Society of Nuclear Medicine* 51:1293-300 (2010). In general, Zr-89 oxalate was neutralized to pH 7.0-7.2 with 1 M $Na_2CO_3$. The DFO-antibodies were then added. The reaction was incubated at room temperature for 1-2 hours. Subsequent purification was conducted using either a PD10 desalting column with 0.9% saline.

In Vitro Experiments $^{89}$Zr-5B1 was investigated for stability in vitro in 0.9% saline and in 1% bovine serum albumin for 5 days at 37° C. Changes in radiochemical purity were monitored at t=0-5 days via radio iTLC with 50 mM DTPA as mobile phase. In vitro immunoreactivity assays were performed according to the protocol described by Lindmo et al., *Journal of Immunological Methods* 72:77-89 (1984), to demonstrate the integrity of the Zr-89 radiolabeled antibodies.

Animal Models

All animal studies were conducted in accordance with the guidelines set by the Institutional Animal Care and Use Committee. Female CB17SC-F SCID mice (Jackson Laboratories, 6-8 weeks, 20-22 g) or nude athymic (nu/nu) mice were induced with tumors on hind legs. All cell lines were inoculated subcutaneously in 200 μL of 1:1 media:Matrigel (BD Biosciences) solution and grown to a maximum tumor volume of 250 mm$^3$ before use.

Biodistribution Studies

Biodistribution studies were performed on several cohorts of mice bearing separate Colo205-luc colorectal, BxPC3 pancreas and DMS79 small cell lung xenografts (n=3-5). Zr-89 mAbs (10-20 μCi, 1-2 μg) in 100 μL 0.9% saline were administered intravenously in the lateral vein. Additional unlabeled mAb (10-50 μg) was co-injected along with the tracer. A blocking study with 250 μg excess of unlabeled mAb was performed to address specificity of the antibody to sLe$^a$ in a cohort of mice. After each time point (t=24, 48, 120 h p.i.), the mice were euthanized by asphyxiation with $CO_2$. Blood was collected immediately via cardiac puncture while the tumor along with chosen organs was harvested. The wet weight of each tissue was measured, and the radioactivity bound to each organ was counted using a Wizard$^2$ 2480 gamma counter (Perkin Elmer). The percentage of tracer uptake expressed as % injected dose per gram (% ID/g) was calculated as the activity bound to the tissue per organ weight per actual injected dose decay-corrected to the time of counting.

Small Animal Immuno-PET

Imaging experiments were accomplished with a micro-PET Focus 120 or R4 scanner (Concorde Microsystems). Mice (n=3-5) were administered Zr-89 labeled antibodies (200-300 μCi, 15-25 μg) in 100-200 μL 0.9% saline formulations via lateral tail vein injections. PET whole body acquisitions were recorded on mice at 24-96 h p.i. while anesthesized with 1.5-2.0% isofluorane (Baxter Healthcare) in oxygen. The images were analyzed using ASIPro VM™ software (Concorde Microsystems). Regions-of-interest (ROI) were drawn and plotted vs. time.

Immunohistochemistry

Biotinylated 5B1 was prepared by incubating 20× molar excess Sulfo-NHS-LC-biotin (Thermo Scientific/Pierce cat#21327) for 30 minutes at room temperature. Free biotin was removed with Zebra™ desalt spin columns (Thermo Scientific/Pierce, cat #89889) according to the manufacturer's instructions. The antibodies were buffer exchanged to PBS containing 0.01% sodium azide at a concentration of 1.1 mg/ml. The binding on DMS79 cells was confirmed by FACS and was comparable to the parent 5B1 antibody.

Preliminary immunohistochemistry staining conditions were determined using Colo205 cells as positive control and SK-MEL28 cells as negative control. Cell pellets were prepared, formalin fixed and paraffin embedded. The slides were incubated with biotinylated 5B1 diluted in 10% (v/v) normal human serum in PBS (Jackson ImmunoResearch Labs; cat#009-000-121). The staining was performed by Ventana automation (Discovery XT platform-Ventana Medical Systems, Inc, Tucson, Ariz.) with standard streptavidin-biotin immunoperoxidase method and DAB detection system as a staining method. Antigen recovery was conducted using heat and Ventana's CC1 conditioning solution. CA 19.9 mouse monoclonal (clone 116-NS-19-9) from Signet (Covance) gave comparable results in the pilot study. Colo205 cells are strongly positive with biotinylated 5B1 used at 10 μg/ml while SKMEL28 cells were completely negative. Histo-Array™ tissue microarrays were purchased from Imgenex (San Diego, Calif.). The following slides containing tumor biopsy cores as well as some normal tissue cores were used: IMH-327 (Common Cancers, 59 samples), IMH-359 (colorectal: cancer-metastasis-normal; 59 samples), and IMH-324 (Metastatic cancer to ovary). Pancreatic tumor tissue cores were present on IMH-327.

sLe$^a$ Serum Concentration In Vivo

Mice bearing xenografts of Colo205, BxPC3 and DMS79 were exsanguinated for sLe$^a$ antigen assays. A group of mice with no tumor served as a control. The sLe$^a$ levels in the sera of mice were measured using the ST AIA-PACK CA19.9 kit (Cat#025271, TOSOH Bioscience Inc, South San Francisco, Calif.). The principle of the assay is based on the two site immunoenzyme-metric assay. The analysis was performed as described in the manufacturer's instruction manual. The optical density of immunoassay plates were measured by TOSOH AIA2000 Automated immunoassay analyzer (TOSOH Bioscience, Inc, San Francisco, Calif.).

Statistical Analysis

Data values were expressed as the mean±SD unless otherwise stated. Statistical analysis was performed using GraphPad Prism version 5.03 software using one-way ANOVA followed by Dunnett test. A P value of <0.05 is considered statistically significant.

Results

The binding specificity of 5B1 was probed by staining selected malignant and normal tissue microarrays. 5B1 reactivity was restricted to malignancies and occasional normal tissues previously known to overexpress sLe$^a$ (FIG. 19; Table 9). Most normal tissues were completely negative (Table 9). In contrast, strong positive staining was found in 21/34 colon adenocarcinomas (62%), 33/57 adenocarcinoma metastases to the ovary (58%), and 7/9 pancreatic ductal cancers (66%) at various stages (Table 10). As shown in FIG. 19, typical reactivity was diffuse cytoplasmic staining with some tumor cells clearly showing distinct staining of the cell membrane. In addition, some signet ring ovarian cancers, and some cancers of the lung and breast were also found to be strongly positive. In contrast, only 4/43 prostate cancer samples and 0/51 GIST cases were positive (data not shown).

TABLE 9

Survey of 5B1 binding to normal tissues.

| Normal Tissue | Stain |
|---|---|
| Brain | negative |
| Breast | positive |
| Colon | positive |
| Kidney | negative |
| Liver | negative |
| Lung | negative |
| Lymph node | negative |
| Muscle | negative |
| Pancreas | positive |
| Placenta | negative |
| Skin | negative |
| Spleen | negative |
| Stomach | negative |

TABLE 10

Staining of Pancreatic Ductal Adenocarcinomas with 5B1.

| IHC 5B1 | Stage | Age | Sex | Histology |
|---|---|---|---|---|
| neg | II | 71 | M | moderately differentiated |
| pos++ | III | 68 | M | moderately differentiated |
| neg | III | 64 | F | moderately differentiated |
| pos++ | III | 46 | M | moderately differentiated |
| pos++ | III | 54 | M | moderately differentiated |
| pos++ | III | 40 | M | moderately differentiated |
| pos+/− | IVA | 66 | M | moderately differentiated |
| pos++ | IVA | 45 | M | moderately differentiated |
| poor tissue | IVA | 64 | F | moderately differentiated |
| pos++ | IVA | 69 | M | poorly differentiated |

The high specificity of 5B1 immunostaining for cancer tissues expressing sLe$^a$ was the basis for using this mAb as a PET probe. Modification of 5B1 with the benzyl-isothiocyanate analog of desferrioxamine (DFO-Bz-NCS) was made at a ratio of 4:1 (chelate:mAb) with subsequent purification via centrifugal filtration using saline as the washing buffer. Facile radiolabeling with Zr-89 proceeded at room temperature after pH adjustment to 7.0-7.2. A narrower pH range closer to neutral is necessary to achieve optimum radiolabeling yields of >80%. Free, unbound Zr-89 was removed via PD10 desalting column. Concentration of the product was made using a centrifugal filter (MWCO: 10 kDa). A relatively high specific activity of 12.1±1.1 mCi/mg was established. Radiochemical purities of more than 95% were ensured prior to use. Immunoreactivity assays displayed retention of activity for sLe$^a$ (72.4±1.1%, n=3). Stability in bovine serum albumin at 37° C. was maintained at >95% over 5 days (data not shown). In saline, de-metallation was observed as early as 24 h (>85% complexed) with about >75% radiometal bound after 120 h at 37° C.

Small animal PET imaging and biodistribution studies were conducted using female SCID mice subcutaneously implanted with BxPC3 pancreas cancer xenografts on the left hind leg. Acquired PET images confirmed substantial delineation of the tumor-associated sLe$^a$ by $^{89}$Zr-5B1. From the maximum intensity projections (MIP) in FIG. 20, the BxPC3 xenografts (n=3) showed exceptional accretion of the radiotracer administered intravenously. Regions-of-interest (ROI) drawn on the tumor from the PET images displayed an uptake of 5.0±0.4% ID/g (2 h), 16.2±2.5% ID/g (24 h), 23.8±4.7% ID/g (48 h), 36.8±6.1% ID/g (96 h) and 49.5±7.7% ID/g (120 h). Blood pool and normal tissue binding activity appeared to clear after 24 h p.i. Results from the biodistribution experiments are consistent with the PET data. High tumor localization of $^{89}$Zr-5B1 at 24 h (84.7±12.3% ID/g, n=4) was observed; increased uptake was exhibited further at 120 h p.i. (114.1±23.1% ID/g, n=4) (FIG. 21). The tumor uptake exceeds 100% due to the small weight (62.4±0.03 mg). The % ID at 24 h p.i. was found to be ten-fold higher than that of the non-specific IgG at similar time points (FIG. 21 Inset). Competitive inhibition with 250 μg of non-radiolabeled 5B1 at 24 h p.i. blocked the tracer accumulation defining the specificity of uptake. Minimal binding of the $^{89}$Zr-5B1 to normal pancreas and the rest of the harvested normal tissues was observed, providing a high tumor-to-tissue contrast at all time points.

Following the above results, $^{89}$Zr-5B1 was assayed in an orthotopic BxPC3 pancreas tumor model. Orthotopic models are clinically relevant and offer an clinically accepted test of the efficacy of the PET probe. After inoculation in the pancreas, the tumor growth was monitored weekly via bioluminescent optical imaging. PET imaging experiments were conducted once the tumors are palpable. A comparison of probe tumor delineation properties were made between FDG-PET and $^{89}$Zr-5B1 (FIG. 25). Computed tomography (CT) in tandem with PET afforded an enhanced visualization of the anatomic region of interest.

To evaluate $^{89}$Zr-5B1 as a PET probe in other sLe$^a$ expressing adenocarcinomas, $^{89}$Zr-5B1 was assayed in lung and colon cancer models. Small animal experiments were conducted using DMS79 small cell lung cancer cells and Colo205-luc colon cancer cells injected subcutaneously on the right hind leg of female SCID mice. PET MIP images were acquired after 24-120 h p.i. of 200-300 μCi (16-25 μg) injected intravenously. Heterogeneous DMS79 tumor uptake was demonstrated with 38.15±2.12% ID/g as early as 24 h p.i with excellent signal against background (FIG. 22, panel A). An increase in tracer tumor accumulation resulted after 48 h p.i. (44.60±6.47% ID/g) with retention at 120 h p.i. (41.97±12.23% ID/g). Non-specific bound $^{89}$Zr-5B1 cleared rapidly from normal tissues with minimal to no background uptake at 48 h p.i. In addition, tumor delineation was observed in the Colo205-luc xenografts as shown in FIG. 22, panel B at 24-120 h p.i. The ROIs displayed tumor accumulation with 10.5±0.76, 23.5±2.7, 24.8±4.0, 18.4±4.7, 16.5±2.3% ID/g at 2, 24, 48, 96 and 120 h respectively. An observable increase in liver accumulation resulted over time with consequent decrease in tumor uptake as shown in the regions-of-interest drawn from the PET images (FIG. 22, panel C). Data generated from the biodistribution studies correlate well with the observed PET results (data not shown).

The sLe$^a$ level in mouse serum as tumors progressed was quantified. Exsanguination of SCID mice bearing Colo205, DMS79 and BxPC3 xenografts with a non-tumor bearing group serving as control was performed. sLe$^a$ values showed high levels of sLe$^a$ in mice challenged with Colo205 in comparison to the pancreatic BxPC3 and DSM79 implanted mice (Table 11).

TABLE 11 sLe$^a$ serum values from mice bearing colorectal (Colo205), pancreas (BxPC3) and small cell lung (DMS79) tumor xenografts compared to control.

| Tumor type | Animal # | Tumor volume, mm$^3$ | sLe$^a$, U/ml |
|---|---|---|---|
| Colo205-luc | M1 | 269.5 | 3227 |
|  | M2 | 257.3 | 2957 |
|  | M3 | 281.3 | 1318 |

TABLE 11-continued sLe$^a$ serum values from mice bearing colorectal (Colo205), pancreas (BxPC3) and small cell lung (DMS79) tumor xenografts compared to control.

| Tumor type | Animal # | Tumor volume, mm$^3$ | sLe$^a$, U/ml |
|---|---|---|---|
| BxPC3 | M1 | 232.38 | N.D. |
| | M2 | 320.00 | N.D. |
| | M3 | 220.50 | N.D. |
| DMS79 | M1 | 288.0 | N.D. |
| | M2 | 245.0 | N.D. |
| | M3 | 232.4 | N.D. |
| Control | M1 | — | 3 |
| | M2 | — | 3 |
| | M3 | — | 3 |

N.D. = Not detected.

These results demonstrate that a radiolabeled anti-sLe$^a$ antibody ($^{89}$Zr-5B1) is specific for the detection and diagnosis of pancreatic adenocarcinoma and other sLe$^a$ positive adenocarcinomas. $^{89}$Zr-5B1 was produced with excellent yields and purity, along with high specific activity and retained immunoreactivity. Evaluation of $^{89}$Zr-5B1 in subcutaneous, orthotopic and metastatic pancreas tumor models afforded excellent tumor delineation and diagnosis. Preclinical evaluation of this radiotracer in colon and small cell lung tumor-bearing small animals demonstrated the universal utility of this tracer for malignancies expressing sLe$^a$.

Example III

Anti-sLe$^a$ Diabodies Bind to Various Cancer Cell Lines

Two diabodies were generated using the VH and VL domains of 5B1 and 7E3 clonal isolates described herein, designated 5B1CysDb and 7E3CysDb, respectively (FIGS. 9 and 10). Both diabodies contained a five amino acid linker region between the VL and VH domains. A poly histidine tag on the C-terminal, which was utilized for purification and detection, was also included for both diabodies.

The binding of 5B1CysDb and 7E3CysDb to three cancer cell lines: (1) DMS-79 cells, a small-cell lung cancer suspension cell line; (2) Capan-2 cells, pancreatic adenocarcinoma cells; and (3) BxPC3 cells, pancreatic cancer cells, was assayed by incubating 0.25 million cells in 0.2 ml with 10 µg/ml 5B1CysDb or 7E3CysDb, respectively. The cell and diabody combinations were incubated for 40 minutes on ice in PBS/2% FBS.

After washing, the cells were incubated for 40 minutes with 0.2 ml ALEXA-488-labeled anti-His antibody diluted 1:1000 (Life Technology, Cat # A21215). Following a second wash, the cells were analyzed with a Guava Flow Cytometer. Both 5B1 CysDb and 7E3CysDb demonstrated significant binding to DMS-79, Capan-2 and BxPC3 cells (Table 12).

TABLE 12

Binding of 5B1CysDb and 7E3CysDb to Cell Lines

| | 5B1CysDb | | 7E3CysDb | |
|---|---|---|---|---|
| Cell line | Percent (+) | MFI | Percent (+) | MFI |
| DMS-79 | 98.1 | 113.0 | 93.8 | 124.6 |
| Capan-2 | 63.8 | 98.5 | 65.9 | 235.3 |
| BxPC3 | 51.3 | 39.9 | 50.2 | 49.7 |

MFI—mean fluorescent intensity

Example IV

Administration of 5B1 and Taxol Inhibits Tumor Growth

The anti-tumor activity of co-administrating an anti-sLe$^a$ antibody (5B1) and the chemotherapeutic agent Taxol (Paclitaxel) was assessed in xenograft models of pancreatic cancer and small cell lung cancer. As described previously herein, 1 million BxPc3 cells (pancreatic tumor cells) or 5 million DMS-79 cells (small cell lung cancer cells) were injected into the hind flank of 6 weeks old female CB17 SCID mice (Day 0; N=5). DMS79 tumors were allowed to grow for 21 days until the average tumor size was 193±64 mm3. Human IgG or 5B1 (0.5 or 1 mg) was given ip twice a week (strating on Day 21), and Taxol (0.2 mg/dose) was administered iv on days 23, 30, 37 and 44. In the DMS-79 xenograft model, co-administration of 5B1 antibody and Taxol significantly limited tumor growth and resulted in tumor regression in comparison to control human IgG or 5B1 antibody and Taxol administered individually (FIG. 23).

In the BxPc3 xenograft model, tumors were grown for 14 days, at which they reached an average of 126±30 mm3. Taxol was administered iv on days 14, 21, 28 and 34 (weekly) and 5B1 was given twice per week starting on day 14. Co-administration of 5B1 antibody and Taxol significantly limited tumor growth in comparison to controls or 5B1 antibody and Taxol administered individually (FIG. 24). These results demonstrate a synergistic effect of an anti-sLe$^a$ antibody and a chemotherapeutic agent in preventing tumor growth and/or reducing tumor size for pancreatic and small cell lung cancers.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. An isolated antibody or antigen binding fragment thereof that binds to Sialyl-Lewis$^a$, said antibody or antigen binding fragment thereof comprising a variable heavy chain (VH) domain and a variable light chain (VL) domain, where said VH domain and said VL domain respectively comprise an amino acid sequence selected from the group consisting of residues 20-142 of SEQ ID NO: 2 and residues 20-130 of SEQ ID NO: 4; residues 20-142 of SEQ ID NO: 6 and residues 20-129 of SEQ ID NO: 8; residues 20-142 of SEQ ID NO: 10 and residues 20-130 of SEQ ID NO: 12; and residues 20-145 of SEQ ID NO: 14 and residues 23-130 of SEQ ID NO: 16.

2. The isolated antibody or antigen binding fragment thereof of claim 1, wherein said antibody is a human antibody.

3. The isolated antibody or antigen binding fragment thereof of claim 1, wherein said antibody antigen binding fragment is selected from the group consisting of a Fab, a Fab', a F(ab')$_2$, a scFV, a diabody, a triabody, a minibody and a single-domain antibody (sdAB).

4. The antibody or antigen binding fragment thereof of claim 3, wherein said antibody antigen binding fragment is a diabody.

5. The antibody or antigen binding fragment of claim 4, wherein said diabody comprises the amino acid sequence of SEQ ID NO: 18 or 20.

6. The isolated antibody or antigen binding fragment thereof of claim 1, wherein said antibody is a monoclonal antibody.

7. The isolated antibody or antigen binding fragment thereof of claim 1, wherein said antibody is an IgG or IgM isotype.

8. The isolated antibody or antigen binding fragment thereof of claim 7, wherein said IgG antibody is an IgG1 subclass.

9. An conjugate comprising an isolated antibody or antigen binding fragment of claim 1 conjugated or recombinantly fused to a diagnostic agent, detectable agent or therapeutic agent.

10. The conjugate of claim 9, wherein said conjugate comprises a detectable agent.

11. The conjugate of claim 10, wherein said detectable agent is zirconium ($^{89}$Zr).

12. A pharmaceutical composition comprising the antibody or antigen binding fragment of claim 1 and a pharmaceutically acceptable carrier.

13. A method for treating or preventing a disease comprising administering a therapeutically effective amount of the pharmaceutical composition of claim 12 to a subject in need thereof, wherein said disease is cancer or a tumor formation having cells expressing sLe$^a$, and wherein preventing is the forestalling of a clinical symptom indicative of cancer or tumor formation or guarding against tumor metastasis.

14. The method of claim 13, wherein said cancer or tumor is selected from the group consisting of a tumor of the gastrointestinal tract, colon cancer, colorectal adenocarcinoma, metastatic colon cancer, colorectal cancer, pancreatic cancer, pancreatic adenocarcinoma, small cell carcinoma of the lung, bladder adenocarcinoma, signet ring ovarian cancer, ovarian cancer, metastatic carcinoma, adenocarcinoma of the stomach, adenocarcinoma of the esophagus, adenocarcinoma of the throat, adenocarcinoma of the urogenital tract, and adenocarcinoma of the breast.

15. The method of claim 13, wherein said method further comprises administering concurrently or successively a second therapeutic agent.

16. The method of claim 15, wherein said second therapeutic agent is a chemotherapeutic agent or an immunotherapeutic agent.

17. A method for detecting a tumor in a subject comprising administering an effective amount of the conjugate of claim 10 to a subject in need thereof, wherein the tumor expresses $sLe^a$.

18. An isolated polynucleotide encoding the VH domain of claim 1.

19. An isolated polynucleotide encoding the VL domain of claim 1.

20. An isolated polynucleotide encoding the VH and the VL domain of claim 1.

* * * * *

SEQUENCE LISTING

<160> NUMBER OF SEQ ID NOS: 20

<210> SEQ ID NO 1
<211> LENGTH: 426
<212> TYPE: DNA
<213> ORGANISM: Artificial Sequence
<220> FEATURE:
<223> OTHER INFORMATION: VH chain domain of clone 5B1

<400> SEQUENCE: 1

```
atggagtttg gctgagctg gcttttctt gtggctattt taaaaggcgt acagtgccag    60
gtgcagctgg tggagtctgg gggaggctcg gtgcagcctg gcaggtccct gagactctcc   120
tgtgaagcct ctggattcac ctttgaggcc tatgccatgc actgggtccg gcaacctcca   180
gggaagggcc tggagtgggt ctcaagtatt aattggaata gtggtcgcat agcctatgcg   240
gactctgtga aggccgatt caccatctcc agagacaacg ccaggaattc cctgtatctg    300
caaatgaaca gtctgagact tgaggacacg gccttctatt actgtgcaaa agatatacgg   360
aggtttagta ccgggggggc ggagtttgag tactggggcc agggaaccct ggtcaccgtc   420
tcctca                                                              426
```

<210> SEQ ID NO 2
<211> LENGTH: 142
<212> TYPE: PRT
<213> ORGANISM: Artificial Sequence
<220> FEATURE:
<223> OTHER INFORMATION: VH chain domain of clone 5B1

<400> SEQUENCE: 2

```
Met Glu Phe Gly Leu Ser Trp Leu Phe Leu Val Ala Ile Leu Lys Gly
  1               5                  10                  15
Val Gln Cys Gln Val Gln Leu Val Glu Ser Gly Gly Gly Ser Val Gln
                 20                  25                  30
Pro Gly Arg Ser Leu Arg Leu Ser Cys Glu Ala Ser Gly Phe Thr Phe
             35                  40                  45
Glu Ala Tyr Ala Met His Trp Val Arg Gln Pro Pro Gly Lys Gly Leu
         50                  55                  60
Glu Trp Val Ser Ser Ile Asn Trp Asn Ser Gly Arg Ile Ala Tyr Ala
 65                  70                  75                  80
Asp Ser Val Lys Gly Arg Phe Thr Ile Ser Arg Asp Asn Ala Arg Asn
                 85                  90                  95
Ser Leu Tyr Leu Gln Met Asn Ser Leu Arg Leu Glu Asp Thr Ala Phe
            100                 105                 110
Tyr Tyr Cys Ala Lys Asp Ile Arg Arg Phe Ser Thr Gly Gly Ala Glu
            115                 120                 125
Phe Glu Tyr Trp Gly Gln Gly Thr Leu Val Thr Val Ser Ser
            130                 135                 140
```

<210> SEQ ID NO 3
<211> LENGTH: 390
<212> TYPE: DNA
<213> ORGANISM: Artificial Sequence
<220> FEATURE:
<223> OTHER INFORMATION: VL chain domain of clone 5B1

<400> SEQUENCE: 3

```
atggccggct ccctctcct cctcaccctc ctcactcact gtgcagggtc ttgggcccag    60
tctgtgctga ctcagccgcc ctcagcgtct gggaccccg gcagagggt caccatctct    120
tgttctggaa gcagctccaa catcggaagt aattttgtat actggtacca gcagctccca   180
ggaacggccc ccaaactcct catatatagg aataatcagc ggccctcagg ggtccctgac   240
cgattctctg gctccaggtc tgcacctca gcctccctgg ccatcagtgg actccggtcc    300
gaggatgagg ctgattatta ctgtgcagca tgggatgaca gctgggagg ccattatgtc    360
ttcggaactg ggaccaaggt caccgtcctt                                    390
```

<210> SEQ ID NO 4
<211> LENGTH: 130
<212> TYPE: PRT
<213> ORGANISM: Artificial Sequence
<220> FEATURE:
<223> OTHER INFORMATION: VL chain domain of clone 5B1

<400> SEQUENCE: 4

```
Met Ala Gly Phe Pro Leu Leu Leu Thr Leu Leu Thr His Cys Ala Gly
1               5                   10                  15

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Ser Ser Ser Asn Ile
        35                  40                  45

Gly Ser Asn Phe Val Tyr Trp Tyr Gln Gln Leu Pro Gly Thr Ala Pro
    50                  55                  60

Lys Leu Leu Ile Tyr Arg Asn Asn Gln Arg Pro Ser Gly Val Pro Asp
65                  70                  75                  80

Arg Phe Ser Gly Ser Arg Ser Gly Thr Ser Ala Ser Leu Ala Ile Ser
                85                  90                  95

Gly Leu Arg Ser Glu Asp Glu Ala Asp Tyr Tyr Cys Ala Ala Trp Asp
            100                 105                 110

Asp Ser Leu Gly Gly His Tyr Val Phe Gly Thr Gly Thr Lys Val Thr
        115                 120                 125

Val Leu
    130
```

<210> SEQ ID NO 5
<211> LENGTH: 426
<212> TYPE: DNA
<213> ORGANISM: Artificial Sequence
<220> FEATURE:
<223> OTHER INFORMATION: VH chain domain of clone 9H3

<400> SEQUENCE: 5

```
atggagtttg gctgagctg gcttttctt gtggctattt taaaaggcgt acagtgcgaa      60
gtgcagctgt tggagtctgg gggaggcttg gtacagcctg gcaggtccct gagactctcc   120
tgtgcggcct ctggatttac ctttgatgat tatgtcatgc actgggtccg gcaagctcca   180
gggaagggcc tggagtgggt ctcaagtatt agttggaata gtggtagcat aggctatgcg   240
gactctgtga agggccgatt catcatctcc agagacaacg ccaagaactc cctgtatctg   300
caaatgaaca gtctgagagc tgaggacacg gccttgtatt actgtgcaaa agatcgtcgt   360
attaggggtg actcgggggtt cgagggtgac tactggggcc agggaaccct ggtcaccgtc   420
tcctca                                                              426
```

<210> SEQ ID NO 6
<211> LENGTH: 142
<212> TYPE: PRT
<213> ORGANISM: Artificial Sequence
<220> FEATURE:
<223> OTHER INFORMATION: VH chain domain of clone 9H3

<400> SEQUENCE: 6

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30
```

```
Pro Gly Arg Ser Leu Arg Leu Ser Cys Ala Ala Ser Gly Phe Thr Phe
            35                  40                  45

Asp Asp Tyr Val Met His Trp Val Arg Gln Ala Pro Gly Lys Gly Leu
 50                  55                  60

Glu Trp Val Ser Ser Ile Ser Trp Asn Ser Gly Ser Ile Gly Tyr Ala
 65                  70                  75                  80

Asp Ser Val Lys Gly Arg Phe Ile Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Lys Asp Arg Arg Ile Arg Gly Asp Ser Gly Phe Glu
            115                 120                 125

Gly Asp Tyr Trp Gly Gln Gly Thr Leu Val Thr Val Ser Ser
130                 135                 140
```

<210> SEQ ID NO 7
<211> LENGTH: 387
<212> TYPE: DNA
<213> ORGANISM: Artificial Sequence
<220> FEATURE:
<223> OTHER INFORMATION: VL chain domain of clone 9H3

<400> SEQUENCE: 7

```
atggccggct tccctctcct cctcaccctc ctcactcact gtgcagggtc ttgggcccag    60
tctgtgttga cgcagccgcc ctcagcgtct ggaccccg gcagagggt caccatctct     120 tgttctggaa gcagctccaa catcggaagt aattatgtat actggtacca gcagctccca   180
ggaacggccc ccaaactcct catctatagg aataatcagc ggccctcagg ggtccctgac   240
cgattctctg gctccaagtc tggcacctca gcctccctgg ccatcagtgg ctccggtcc    300 gaggatgagg ctgattatta ctgtgcagca tgggatgcca gcctgagtgg tgtggtattc   360
ggcggaggga ccaagctgac cgtccta                                       387
```

<210> SEQ ID NO 8
<211> LENGTH: 129
<212> TYPE: PRT
<213> ORGANISM: Artificial Sequence
<220> FEATURE:
<223> OTHER INFORMATION: VL chain domain of clone 9H3

<400> SEQUENCE: 8

```
Met Ala Gly Phe Pro Leu Leu Leu Thr Leu Leu Thr His Cys Ala Gly
 1               5                  10                  15

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Ser Ser Ser Asn Ile
            35                  40                  45

Gly Ser Asn Tyr Val Tyr Trp Tyr Gln Gln Leu Pro Gly Thr Ala Pro
 50                  55                  60

Lys Leu Leu Ile Tyr Arg Asn Asn Gln Arg Pro Ser Gly Val Pro Asp
 65                  70                  75                  80

Arg Phe Ser Gly Ser Lys Ser Gly Thr Ser Ala Ser Leu Ala Ile Ser
                85                  90                  95

Gly Leu Arg Ser Glu Asp Glu Ala Asp Tyr Tyr Cys Ala Ala Trp Asp
            100                 105                 110

Ala Ser Leu Ser Gly Val Val Phe Gly Gly Gly Thr Lys Leu Thr Val
            115                 120                 125
```

Leu

<210> SEQ ID NO 9
<211> LENGTH: 426
<212> TYPE: DNA
<213> ORGANISM: Artificial Sequence
<220> FEATURE:
<223> OTHER INFORMATION: VH chain domain of clone 5H11

<400> SEQUENCE: 9

```
atggagtttg ggctgagctg gcttttcctt gtggctattt taaaaggcgt acagtgccag      60
gtgcagctgt tggagtctgg gggaggcttg gtacagcctg gcaggtccct gagactctcc    120
tgtgcagcct ctggattcac ctttgatgaa tatgccatgc actgggtccg gcaagctcca    180
gggaagggcc tggagtgggt ctcaagtgtt agttggaata gtggtagcat aggctatgcg    240
gactctgtga agggccgatt caccatctcc agagacaacg ccaagaactc cctgtatcta    300
caaatgaaca gtctgagagc tgaggacacg gccttgtatt actgtgcaaa agatatacgg    360
acctatagca ccgggggggc ggagtttgcc tcctggggcc agggaaccct ggtcaccgcc    420
tcctca                                                              426
```

<210> SEQ ID NO 10
<211> LENGTH: 142
<212> TYPE: PRT
<213> ORGANISM: Artificial Sequence
<220> FEATURE:
<223> OTHER INFORMATION: VH chain domain of clone 5H11

<400> SEQUENCE: 10

```
Met Glu Phe Gly Leu Ser Trp Leu Phe Leu Val Ala Ile Leu Lys Gly
1               5                   10                  15

Val Gln Cys Gln Val Gln Leu Leu Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Glu Tyr Ala Met His Trp Val Arg Gln Ala Pro Gly Lys Gly Leu
    50                  55                  60

Glu Trp Val Ser Ser Val Ser Trp Asn Ser Gly Ser Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Lys Asp Ile Arg Thr Tyr Ser Thr Gly Gly Ala Glu
        115                 120                 125

Phe Ala Ser Trp Gly Gln Gly Thr Leu Val Thr Ala Ser Ser
    130                 135                 140
```

<210> SEQ ID NO 11
<211> LENGTH: 390
<212> TYPE: DNA
<213> ORGANISM: Artificial Sequence
<220> FEATURE:
<223> OTHER INFORMATION: VL chain domain of clone 5H11

<400> SEQUENCE: 11

```
atggccggct cccctctcct cctcaccctc ctcactcact gtgcagggtc ttgggcccag     60
tctgtgttga cgcagccgcc ctcagcgtct gggaccccccg ggcagagggt caccatctct    120
```

```
tgttctggaa gcagctccaa catcggaagt aattatgtat actggtacca gcaggtccca    180
ggaacggccc ccaaactcct catctatagg aataatcagc ggccctcagg ggtccctgac    240
cgattctctg gctccaagtc tggcacctca gcctccctgg ccatcagtgg gctccggtcc    300
gaggatgagg ctgattatta ctgtgcagca tgggatgaca gcctgagtgg ccattatgtc    360
ttcggaactg ggaccaaggt caccgtccta                                     390
```

<210> SEQ ID NO 12
<211> LENGTH: 130
<212> TYPE: PRT
<213> ORGANISM: Artificial Sequence
<220> FEATURE:
<223> OTHER INFORMATION: VL chain domain of clone 5H11

<400> SEQUENCE: 12

```
Met Ala Gly Phe Pro Leu Leu Thr Leu Leu Thr His Cys Ala Gly
1               5                   10                  15

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Ser Ser Ser Asn Ile
        35                  40                  45

Gly Ser Asn Tyr Val Tyr Trp Tyr Gln Gln Val Pro Gly Thr Ala Pro
    50                  55                  60

Lys Leu Leu Ile Tyr Arg Asn Asn Gln Arg Pro Ser Gly Val Pro Asp
65                  70                  75                  80

Arg Phe Ser Gly Ser Lys Ser Gly Thr Ser Ala Ser Leu Ala Ile Ser
                85                  90                  95

Gly Leu Arg Ser Glu Asp Glu Ala Asp Tyr Tyr Cys Ala Ala Trp Asp
            100                 105                 110

Asp Ser Leu Ser Gly His Tyr Val Phe Gly Thr Gly Thr Lys Val Thr
        115                 120                 125

Val Leu
    130
```

<210> SEQ ID NO 13
<211> LENGTH: 435
<212> TYPE: DNA
<213> ORGANISM: Artificial Sequence
<220> FEATURE:
<223> OTHER INFORMATION: VH chain domain of clone 7E3

<400> SEQUENCE: 13

```
atggagtttg ggctgagctg gcttttcttt gtggctattt taaaaggcgt acagtgccaa    60
gtgcagctgt tggagtctgg gggaggcgtg gtccagcctg gaggtccct gagactctcc    120 tgtgcagcct ctggattcac cttcagtttc tatggcatgc actgggtccg ccaggctcca    180
ggcaaggggc tggagtgggt ggcagctata tcatatgatg gaagtaataa atactatgca    240
gactccgtga agggccgatt caccatctcc agagacaatt ccaagaacac gctgtatctg    300
caaatgaaca gcctgagagc tgaggacacg gctgtgtatt actgtgcgaa aggcccaac    360 caatttttatt gtagtgatgg tagatgctac tccattgact actggggcca gggaaccctg    420
gtcaccgtct cctca                                                     435
```

<210> SEQ ID NO 14
<211> LENGTH: 145
<212> TYPE: PRT
<213> ORGANISM: Artificial Sequence
<220> FEATURE:
<223> OTHER INFORMATION: VH chain domain of clone 7E3

<400> SEQUENCE: 14

```
Met Glu Phe Gly Leu Ser Trp Leu Phe Leu Val Ala Ile Leu Lys Gly
1               5                   10                  15

Val Gln Cys Gln Val Gln Leu Leu Glu Ser Gly Gly Val Val Gln
            20                  25                  30

Pro Gly Arg Ser Leu Arg Leu Ser Cys Ala Ala Ser Gly Phe Thr Phe
            35                  40                  45

Ser Phe Tyr Gly Met His Trp Val Arg Gln Ala Pro Gly Lys Gly Leu
        50                  55                  60

Glu Trp Val Ala Ala Ile Ser Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Arg Pro Asn Gln Phe Tyr Cys Ser Asp Gly Arg
        115                 120                 125

Cys Tyr Ser Ile Asp Tyr Trp Gly Gln Gly Thr Leu Val Thr Val Ser
    130                 135                 140

Ser
145
```

<210> SEQ ID NO 15
<211> LENGTH: 390
<212> TYPE: DNA
<213> ORGANISM: Artificial Sequence
<220> FEATURE:
<223> OTHER INFORMATION: VL chain domain of clone 7E3

<400> SEQUENCE: 15

```
atggacatga gggtcccegc tcagctcctg gggctcctgc tactctggct ccgaggtgcc    60
cggtgtgaaa ttgtaatgac gcagtctcca gccaccctgt ctgtgtctcc aggggagaga   120
gccaccctct cctgcagggc cagtcagagt gttagcagca acttagcctg gtaccagcag   180
aaacctggcc aggctcccag gctcctcatc tatggtgcat ccaccagggc cactggtatc   240
ccagccaggt tcagtggcag tgggtctggg acagacttca ctctcaccat cagcagcctg   300
cagtctgtag attctgcagt ttattactgt cagcagtata taaactggcc tccgtacact   360
tttggccagg ggaccaagct ggagatcaaa                                    390
```

<210> SEQ ID NO 16
<211> LENGTH: 130
<212> TYPE: PRT
<213> ORGANISM: Artificial Sequence
<220> FEATURE:
<223> OTHER INFORMATION: VL chain domain of clone 7E3

<400> SEQUENCE: 16

```
Met Asp Met Arg Val Pro Ala Gln Leu Leu Gly Leu Leu Leu Leu Trp
1               5                   10                  15

Leu Arg Gly Ala Arg Cys Glu Ile Val Met Thr Gln Ser Pro Ala Thr
            20                  25                  30

Leu Ser Val Ser Pro Gly Glu Arg Ala Thr Leu Ser Cys Arg Ala Ser
        35                  40                  45

Gln Ser Val Ser Ser Asn Leu Ala Trp Tyr Gln Gln Lys Pro Gly Gln
```

Ala Pro Arg Leu Leu Ile Tyr Gly Ala Ser Thr Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Gln Ser Val Asp Ser Ala Val Tyr Tyr Cys Gln Gln
            100                 105                 110

Tyr Asn Asn Trp Pro Pro Tyr Thr Phe Gly Gln Gly Thr Lys Leu Glu
        115                 120                 125

Ile Lys
    130

<210> SEQ ID NO 17
<211> LENGTH: 750
<212> TYPE: DNA
<213> ORGANISM: Artificial Sequence
<220> FEATURE:
<223> OTHER INFORMATION: Diabody 5B1CysDb sequence

<400> SEQUENCE: 17
cagtctgtgc tgacgcagcc gccctcagcg tctgggaccc ccggggcagag ggtcaccatc        60 tcttgttctg gaagcagctc caacatcgga agtaattttg tatactggta ccagcagctc       120
ccaggaacgg cccccaaact cctcatatat aggaataatc agcggccctc aggggtccct       180
gaccgattct ctggctccag gtctggcacc tcagcctccc tggccatcag tggactccgg       240
tccgaggatg aggctgatta ttactgtgca gcatgggatg acagcctggg aggccattat       300
gtcttcggaa ctgggaccaa ggtcaccgtc ctttctggtg gtggtggtca ggtgcagctg       360
gtggagtctg ggggaggctc ggtgcagcct ggcaggtccc tgagactctc ctgtgaagcc       420
tctggattca cctttgaggc ctatgccatg cactgggtcg gcaacctcc agggaagggc        480 ctggagtggg tctcaagtat taattggaat agtggtcgca tagcctatgc ggactctgtg       540
aagggccgat tcaccatctc cagagacaac gccaggaatt ccctgtatct gcaaatgaac       600
agtctgagac ttgaggacac ggccttctat tactgtgcaa agatatacg gaggtttagt       660 accggggggg cggagtttga gtactggggc cagggaaccc tggtcaccgt ctcctcaggt       720
tctcaccatc accatcacca tggcggttgc                                       750

<210> SEQ ID NO 18
<211> LENGTH: 250
<212> TYPE: PRT
<213> ORGANISM: Artificial Sequence
<220> FEATURE:
<223> OTHER INFORMATION: Diabody 5B1CysDb sequence

<400> SEQUENCE: 18

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Phe Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Arg Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu

```
            85                  90                  95
Gly Gly His Tyr Val Phe Gly Thr Gly Thr Lys Val Thr Val Leu Ser
            100                 105                 110
Gly Gly Gly Gly Gln Val Gln Leu Val Glu Ser Gly Gly Gly Ser Val
            115                 120                 125
Gln Pro Gly Arg Ser Leu Arg Leu Ser Cys Glu Ala Ser Gly Phe Thr
            130                 135                 140
Phe Glu Ala Tyr Ala Met His Trp Val Arg Gln Pro Pro Gly Lys Gly
145                 150                 155                 160
Leu Glu Trp Val Ser Ser Ile Asn Trp Asn Ser Gly Arg Ile Ala Tyr
                165                 170                 175
Ala Asp Ser Val Lys Gly Arg Phe Thr Ile Ser Arg Asp Asn Ala Arg
            180                 185                 190
Asn Ser Leu Tyr Leu Gln Met Asn Ser Leu Arg Leu Glu Asp Thr Ala
            195                 200                 205
Phe Tyr Tyr Cys Ala Lys Asp Ile Arg Arg Phe Ser Thr Gly Gly Ala
            210                 215                 220
Glu Phe Glu Tyr Trp Gly Gln Gly Thr Leu Val Thr Val Ser Ser Gly
225                 230                 235                 240

Ser His His His His His Gly Gly Cys
                245                 250

<210> SEQ ID NO 19
<211> LENGTH: 750
<212> TYPE: DNA
<213> ORGANISM: Artificial Sequence
<220> FEATURE:
<223> OTHER INFORMATION: Diabody 7E3CysDb sequence

<400> SEQUENCE: 19
gatgttgtgc tgacgcagtc tccagccacc ctgtctgtgt ctccagggga gagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagac ttcactctca ccatcagcag cctgcagtct   240
gaagattctg cagttttatta ctgtcagcag tataataact ggcctccgta cacttttggc   300
caggggacca aggtggatat caaatctggt ggtggtggtg aagtgcagct ggtggagtct   360
gggggaggcg tggtccagcc tgggaggtcc ctgagactct cctgtgcagc ctctggattc   420
accttcagtt tctatggcat gcactgggtc cgccaggctc aggcaaggg gctggagtgg   480
gtggcagcta tcatatga tggaagtaat aaatactatg cagactccgt gaagggccga   540
ttcaccatct ccagagacaa ttccaagaac acgctgtatc tgcaaatgaa cagcctgaga   600
gctgaggaca cggctgtgta ttactgtgcg aaaaggccca accaatttta ttgtagtgat   660
ggtagatgct actccattga ctactggggc cagggaaccc tggtcaccgt ctcctcaggt   720
tctcaccatc accatcacca tggcggttgc                                    750

<210> SEQ ID NO 20
<211> LENGTH: 249
<212> TYPE: PRT
<213> ORGANISM: Artificial Sequence
<220> FEATURE:
<223> OTHER INFORMATION: Diabody 7E3CysDb sequence

<400> SEQUENCE: 20

Asp Val Val Leu Thr Gln Ser Pro Ala Thr Leu Ser Val Ser Pro Gly
```

-continued

```
1               5                   10                  15
Glu Arg Ala Thr Leu Ser Cys Arg Ala Ser Gln Ser Val Ser Ser Asn
            20                  25                  30

Leu Ala Trp Tyr Gln Gln Lys Pro Gln Ala Pro Arg Leu Leu Ile Tyr
        35                  40                  45

Gly Ala Ser Thr Arg Ala Thr Gly Ile Pro Ala Arg Phe Ser Gly Ser
        50                  55                  60

Gly Ser Gly Thr Asp Phe Thr Leu Thr Ile Ser Ser Leu Gln Ser Glu
65                  70                  75                  80

Asp Ser Ala Val Tyr Tyr Cys Gln Gln Tyr Asn Asn Trp Pro Pro Tyr
                85                  90                  95

Thr Phe Gly Gln Gly Thr Lys Val Asp Ile Lys Ser Gly Gly Gly Gly
            100                 105                 110

Glu Val Gln Leu Val Glu Ser Gly Gly Val Val Gln Pro Gly Arg
            115                 120                 125

Ser Leu Arg Leu Ser Cys Ala Ala Ser Gly Phe Thr Phe Ser Phe Tyr
        130                 135                 140

Gly Met His Trp Val Arg Gln Ala Pro Gly Lys Gly Leu Glu Trp Val
145                 150                 155                 160

Ala Ala Ile Ser Tyr Asp Gly Ser Asn Lys Tyr Tyr Ala Asp Ser Val
                165                 170                 175

Lys Gly Arg Phe Thr Ile Ser Arg Asp Asn Ser Lys Asn Thr Leu Tyr
            180                 185                 190

Leu Gln Met Asn Ser Leu Arg Ala Glu Asp Thr Ala Val Tyr Tyr Cys
        195                 200                 205

Ala Lys Arg Pro Asn Gln Phe Tyr Cys Ser Asp Gly Arg Cys Tyr Ser
        210                 215                 220

Ile Asp Tyr Trp Gly Gln Gly Thr Leu Val Thr Val Ser Ser Gly Ser
225                 230                 235                 240

His His His His His His Gly Gly Cys
                245
```